US007083922B2

(12) United States Patent
Kacian et al.

(10) Patent No.: US 7,083,922 B2
(45) Date of Patent: *Aug. 1, 2006

(54) DETECTION OF HIV

(75) Inventors: Daniel L. Kacian, San Diego, CA (US); Timothy J. Fultz, Pleasant Hill, CA (US); Sherrol H. McDonough, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 667 days.

This patent is subject to a terminal disclaimer.

(21) Appl. No.: 10/244,490

(22) Filed: Sep. 16, 2002

(65) Prior Publication Data

US 2003/0152916 A1    Aug. 14, 2003

Related U.S. Application Data

(63) Continuation of application No. 09/168,947, filed on Oct. 8, 1998, now Pat. No. 6,589,734, which is a continuation-in-part of application No. 08/469,067, filed on Jun. 6, 1995, now Pat. No. 5,824,518, which is a continuation of application No. 07/550,837, filed on Jul. 10, 1990, now Pat. No. 5,480,784, which is a continuation-in-part of application No. 07/379,501, filed on Jul. 11, 1989, now abandoned.

(51) Int. Cl.
*C07H 21/04* (2006.01)
*C12Q 1/68* (2006.01)

(52) U.S. Cl. ............... 435/6; 435/91.2; 435/91.21; 536/23.1; 536/24.32

(58) Field of Classification Search .............. 435/6, 435/91.1, 91.2; 536/23.1, 24.3
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,754,065 A | 6/1988 | Levenson et al. | |
| 4,786,600 A | 11/1988 | Kramer et al. | |
| 4,800,159 A | 1/1989 | Mullis et al. | |
| 4,851,330 A | 7/1989 | Kohne | 435/6 |
| 5,008,182 A | 4/1991 | Sninsky et al. | 435/5 |
| 5,030,557 A | 7/1991 | Hogan et al. | 435/6 |
| 5,079,351 A | 1/1992 | Sninsky et al. | 536/27 |
| 5,156,949 A | 10/1992 | Luciw et al. | 435/5 |
| 5,166,195 A | 11/1992 | Ecker | 514/44 |
| 5,210,015 A | 5/1993 | Gelfand et al. | |
| 5,283,174 A | 2/1994 | Arnold et al. | |
| 5,399,491 A | 3/1995 | Kacian et al. | |
| 5,409,818 A | 4/1995 | Davey et al. | |
| 5,437,990 A | 8/1995 | Burg et al. | |
| 5,480,784 A | 1/1996 | Kacian et al. | |
| 5,712,385 A | 1/1998 | McDonough et al. | |
| 5,824,518 A | 10/1998 | Kacian et al. | |
| 5,856,088 A | 1/1999 | McDonough et al. | |
| 5,888,779 A | 3/1999 | Kacian et al. | |
| 6,252,059 B1 | 6/2001 | McDonough et al. | |
| 6,589,734 B1 * | 7/2003 | Kacian et al. | 435/6 |

FOREIGN PATENT DOCUMENTS

| | | |
|---|---|---|
| CA | 559709 | 10/1988 |
| CA | 2117884 A1 | 10/1993 |
| CA | 2135646 A1 | 11/1993 |
| EP | 0 185 444 | 6/1986 |
| EP | 0 229 701 | 7/1987 |
| EP | 0 258 017 A2 | 3/1988 |
| EP | 0 267 802 A2 | 5/1988 |
| EP | 0 272 483 A1 | 6/1988 |
| EP | 0 300 796 | 1/1989 |
| EP | 0 329 822 | 8/1989 |
| EP | 0 370 694 | 11/1989 |
| EP | 0 373 960 | 7/1990 |
| EP | 0 403 333 | 12/1990 |
| EP | 0 408 295 | 1/1991 |
| EP | 0 435 150 | 7/1991 |
| EP | 0 469 610 | 2/1992 |
| EP | 0 511 712 | 11/1992 |
| EP | 0 516 540 | 12/1992 |
| EP | 0 519 338 | 12/1992 |
| EP | 0 525 882 | 2/1993 |
| EP | 0 591 914 | 4/1994 |
| EP | 0617132 A2 | 9/1994 |
| EP | 0731175 A2 | 9/1996 |
| WO | 87/06270 | 10/1987 |
| WO | 88/01302 | 2/1988 |
| WO | 88/10315 | 12/1988 |
| WO | 89/01050 | 2/1989 |
| WO | 89/02476 | 3/1989 |
| WO | 89/04375 | 5/1989 |
| WO | WO90/06995 A1 | 6/1990 |
| WO | 90/08440 | 8/1990 |
| WO | WO90/08840 A1 | 8/1990 |
| WO | 90/14439 | 11/1990 |

(Continued)

OTHER PUBLICATIONS

Laure et al., "Detection of HIV1 DNA in Infants and Children by Means of the Polymerase Chain Reaction", Lancet, Sep. 1988, 2(8610):538-41.
Bethesda Research Laboratorie, Life Technology, 1988, p. 30.
Stratagene Catalog, 1988, p. 39.
Agius et al., "Variable Stringency Hybridization of Polymerase Chain Reaction Amplified HIV-1 DNA Fragments," *Journal of Virological Methods* 30:141 (1990).

(Continued)

*Primary Examiner*—Jeanine A. Goldberg
(74) *Attorney, Agent, or Firm*—Charles B. Cappellari

(57) ABSTRACT

The present invention relates to oligonucleotides for use in amplifying and detecting HIV nucleic acid in a sample.

80 Claims, 26 Drawing Sheets

FOREIGN PATENT DOCUMENTS

| | | |
|---|---|---|
| WO | 91/08308 | 6/1991 |
| WO | 91/10746 | 7/1991 |
| WO | 92/00384 | 1/1992 |
| WO | 92/01814 | 2/1992 |
| WO | 92/02638 | 2/1992 |
| WO | 92/16659 | 10/1992 |
| WO | 92/22641 | 12/1992 |
| WO | 93/00447 | 1/1993 |
| WO | 93/02215 | 4/1993 |
| WO | 93/07259 | 4/1993 |
| WO | 93/13223 | 8/1993 |
| WO | 93/25707 | 12/1993 |
| WO | 94/03635 | 2/1994 |

OTHER PUBLICATIONS

Albert and Fenyo, "Simple, Sensitive, and Specific Detection of Human Immunodeficiency Virus Type 1 in Clinical Specimens by Polymerase Chain Reaction with Nested Primers," *Journal of Clinical Microbiology* 28:1560 (1990).

Bell and Ratner, "Specificity of Polymerase Chain Amplification Reactions for Human Immunodeficiency Virus Type 1 DNA Sequences," *AIDS Research and Human Retroviruses* 5:87 (1989).

Bethesda Research Laboratories Catalogue & Reference Guide (1988), Bethesda Research Laboratories, Bethesda, Md. p. 37.

Both et al., "A general strategy for cloning double-stranded RNA: nucleotide sequence of the Simian-11 rotavirus gene 8," *Nucleic Acids Research* 10:7075 (1982).

Bruisten et al., "Enhanced Detection of HIV-1 Sequences Using Polymerase Chain Reaction and a Liquid Hybridization Technique," *Vox Sang* 61:24 (1991).

Cashdollar et al., "Cloning the Double-stranded RNA Genes of a Reovirus: Sequence of the cloned S2 gene," *Proc. Natl. Acad. Sci. USA* 79:7644-7648 (1982).

Clarke et al., "Detection of HIV-1 in Human Lung Macrophages Using the Polymerase Chain Reaction," *AIDS* 4:1133-1136 (1990).

Clarke et al., "Homology of human T-cell leukaemia virus envelope gene with class I HLA gene," *Nature* 305-60-62 (1983).

Coutlee et al., "Immunodetection of DNA with Biotinylated RNA Probes: A Study of Reactivity of a Monoclonal Antibody to DNA-RNA Hybrids," *Analytical Biochemistry* 181:96 (1989).

Dahlen et al., "Detection of Human Immunodeficiency Virus Type 1 by Using the Polymerase Chain Reaction and a Time-Resolved Fluorescence-Based Hybridization Assay," *Journal of Clinical Microbiology* 29:798-804 (1991).

Dudding et al., "Endoribonucleolytic Cleavage of RNA: Oligodeoxynucleotide Hybrids by the Ribonuclease H Activity of HIV-1 Reverse Transcriptase," *Biochemical and Biophysical Research Communications* 167:244-250 (1990).

European Search Report for Appln. No. 90307503.4 dated Jul. 12, 1991.

Ferrer-Le-Coeur et al., "No Evidence of HIV-1 Infection in Seronegative Hemophiliacs and in Seronegative Partners of Seropositive Hemophiliacs through Polymerase Chain Reaction (PCR) and Anti-NEF Serology," *Thrombosis and Haemostasis* 65:478-482 (1991).

Gingeras et al., U.S. Appl. No. 07/202,978, filed Jun. 6, 1988, "Transcription-Based Nucleic Acid Amplification/Detection Systems".

Goswami et al., "Expression of HIV-1 in the Cerebrospinal Fluid Detected by the Polymerase Chain Reaction and its Correlation with Central Nervous System Disease," *AIDS* 5:797-803 (1991).

Grachev et al., "Oligonucleotides complementary to a promoter over the region -8 . . . +2 as transcription primers for *E. coli* RNA polymerase," *Nucleic Acids Research* 12:8509 (1984).

Grankvist et al., "Selection of Primers of Optimal Sensitivity for the Detection of HIV-1 from Africa and Europe by Polymerase Chain Reaction," *AIDS* 5:575-578 (1991).

Guatelli et al., "Alternative Splice Acceptor Utilization during Human Immunodeficiency Virus Type 1 Infection of Cultured Cells," *Journal of Virology* 64:4093-4098 (1990).

Guatelli et al., "Isothermal, *in vitro* amplification of nucleic acids by a multienzyme reaction modeled after retroviral replication," *Proc. Natl. Acad. Sci. USA* 87:1874-1878 (1990) (93).

Gubler *Guide to Molecular Cloning Techniques*; Academic Press, New York, NY pp. 330-335 (1987).

Hart et al., "Direct Detection of HIV RNA Expression in Seropositive Subjects," *The Lancet* 10:596-599 (1988).

Hayes, "The Genetics of Bacteria and their Viruses," John Wiley & Sons Inc., 2nd ed. pp. 239-257, New York (1964).

Holland et al., "Detection of Specific Polymerase Chain Reaction Product by Utilizing the 5'-3' Exonuclease Activity of *Thermus Aquaticus* DNA Polymerase," *Proc. Natl. Acad. Sci. USA* 88:7276-7280 (1991).

Joyce, "Amplification, Mutation and Selection of Catalytic RNA," *Gene* 82:83-87 (1989).

Keller et al., "A Sensitive Nonisotopic Hybridization Assay for HIV-1 DNA," *Analytical Biochemistry* 177:27-32 (1989).

Khorana, "Total Synthesis of a Gene," *Science*, 203:614-25 (1979).

Krug and Berger, "First-Strand cDNA Synthesis Primed with Oligo(dT)," (Methods in Enzymology) *Guide to Molecular Cloning Techniques*, Berger and Kimmel, eds., (Academic Press:NY) 152:316-325 (1987).

Krug and Berger, "Ribonuclease H activities associated with viral reverse transcriptases are endocucleases," *Proc. Natl. Acad. Sci. USA* 86:3539-3543 (1989).

Kumar et al., "A Method for the Rapid Screening of Human Blood Samples for the Presence of HIV-1 Sequences: The Probe-Shift Assay," *AIDS Research and Human Retroviruses* 5:345-354 (1989).

Kupper et al., "Promoter-dependent transcription of TRNA$^{1Tyr}$ genes using DNA fragments produced by restriction enzymes," *Proc. Natl. Acad. Sci. USA* 72:4754 (1975).

Kwoh et al., "Transcription-based amplification system and detection of amplified human immunodeficiency virus type 1 with a bead-based sandwich hybridization format," *Proc. Natl. Acad. Sci. USA* 86:1173-1177 (1989).

Kwok et al., "Identification of Human Immunodeficiency Virus Sequences by Using *In Vitro* Enzymatic Amplification and Oligomer Cleavage Detection," *Journal of Virology* 61:1690-1694 (1987).

Linz et al., "Systematic Studies on Parameters Influencing the Performance of the Polymerase Chain Reaction," *J. Clin. Chem. Clin. Biochem.* 28:5-13 (1990).

Lomonossoff, et al., "The Location of the First AUG Condons in Cowpea Mosaic Virus RNAs," *Nucleic Acids Research*, 10, 16:4861-72 (1982).

Lowary et al., "A Better Way to Make RNA for Physical Studies," *Structure & Dynamics of RNA*, Nato ASI Series Knippenberg, eds. (New York: Plenum Press, 1986) vol. 110.

Mano and Chermann, "Replication of Human Immunodeficiency Virus Type 1 in Primary Cultured Placental Cells," *Res. Virol*. 142:95-104 (1991).

Mariotti et al., "DNA Amplification of HIV-1 in Seropositive Individuals and in Seronegative At-risk Individuals," *AIDS* 4:633-637 (1990).

Mariotti et al., "Failure to Detect Evidence of Human Immunodeficiency Virus type 1 (HIV-1) Infection by Polymerase Chain Reaction Assay in Blood Donors with Isolated Core Antibodies (Anti-p24 or -p17) to HIV-1," *Transfusion* 30:704-706 (1990).

Masukota et al., "Effects of Point Mutations on Formation and Structure of the RNA Primer for Coiei DNA Replication," *Cell* 36:513-522 (1984).

Meyerhans et al., "Temporal Fluctuations in HIV Quasispecies *In Vivo* Are Not Reflected by Sequential HIV Isolations," *Cell* 58:901-910 (1989).

Milligan et al., "Oligoribonucleotide synthesis using T7 RNA polymerase and synthetic DNA templates," *Nucleic Acids Research* 15:8783-98 (1987).

Mousset et al., "Isolation of HIV-1 from Seropositive People Living in Cotonou, Benin," *AIDS* 4:1225-1230 (1990).

Mullis and Faloona, "Specific Synthesis of DNA *in Vitro* via a Polymerase-Catalyzed Chain Reaction," *Methods in Enzymology* 155:335-349 (1987).

Murakawa et al., "Direct Detection of HIV-1 RNA from AIDS and ARC Patient Samples," *DNA* 7:287-295 (1988) (parent).

Okayama and Berg, "High-Efficiency Cloning of Full-Length cDNA," *Molecular and Cellular Biology* 2:161-170 (1982).

Ou et al., "DNA Amplification for Direct Detection of HIV-1 in DNA of Peripheral Blood Mononuclear Cells," *Science* 239:295-297 (1988).

Oyama et al., "Intrinsic Properties of Reverse Transcriptase in Reverse Transcription," *J. Biol. Chem*. 264:18808-18817 (1989).

Pang et al., "High Levels of Unintegrated HIV-1 DNA in Brain Tissue of AIDS Dementia Patients," *Nature* 343:85-89 (1990).

Paterlini et al., "Polymerase Chain Reaction for Studies of Mother to Child Transmission of HIV1 in Africa," *Journal of Medical Virology* 30:53-57 (1990).

Perrin et al., "Human Immunodeficiency Virus DNA Amplification and Serology in Blood Donors," *Blood* 76:641-645 (1990).

Preston et al., "Detection of Nucleic Acids Homologous to Human Immunodeficiency Virus in Wastewater," *Journal of Virological Methods* 33:383-390 (1991).

Pritchard and Stefano, "Amplified Detection of Viral Nucleic Acid at Subattomole Levels Using Q Beta Replicase," *Ann. Biol. Clin*. 48:492-497 (1990).

Ratner et al., "Complete Nucleotide Sequence of the AIDS Virus, HTLV-III," *Nature* 313:277 (1985).

Rossi et al., "An Alternate Method for Synthesis of Double-stranded DNA segments," *J. Biol. Chem*. 257:9226 (1982).

Rudin et al., "Repeated Polymerase Chain Reaction Complementary to Other Conventional Methods for Early Detection of HIV Infection in Infants Born to HIV-Infected Mothers," *Eur. J. Clin. Microbiol. Infect. Dis*. 10:146-156 (1991).

Shaw et al., "Molecular Characterization of Human T-Cell Leukemia (Lymphotropic) Virus Type III in the Acquired Immune Deficiency Syndrome," *Science* 226:1165 (1984).

Shimotohno et al., "Complete Nucleotide Sequence of an Infectious Clone of Human T-cell Leukemia Virus Type II: An Open Reading Frame for the Protease Gene," *Proc. Natl. Acad. Sci. USA* 82:3101 (1985).

Shoebridge et al., "Assessment of HIV Status Using the Polymerase Chain Reaction in Antibody-positive Patients and High-risk Antibody-negative Haemophiliacs," *AIDS* 5:221-224 (1991).

Stent, *Molecular Biology of Bacterial Viruses*, W.H. Freeman & Company, San Francisco pp. 157-163 (1963).

Stevenson et al., "Cloning and Characterization of Human Immunodeficiency Virus Type 1 Variants Diminished in the Ability to Induce Syncytium-Independent Cytolysis," *Journal of Virology* 64:3792-3803 (1990).

Truckenmiller et al., "Evidence for Dual Infection of Rabbits with the Human Retroviruses HTLV-I and HIV-1," *Res. Immunol*. 140:527-544 (1989).

Van de Perre et al., "Postnatal Transmission of Human Immunodeficiency Virus Type 1 From Mother to Infant," *The New England Journal of Medicine* 325:593-598 (1991).

Varas et al., "Influence to PCR Parameters on Amplifications of HIV-1 DNA: Establishment of Limiting Sensitivity," *BioTechniques* 11:384-391 (1991).

Velpandi et al., "Generation of Hybrid Human Immunodeficiency Virus Utilizing the Cotransfection Method and Analysis of Cellular Tropism, " *Journal of Virology* 65:4847-4852 (1991).

Watson and Crick, "Genetical Implications of the Structure of Deoxyribonucleic Acid," *Nature* 171:964-967 (1953).

Watson and Crick, "Molecular Structure of Nucleic Acids," *Nature* p. 737 (Apr. 25, 1953).

Williams et al., "The Polymerase Chain Reaction in the Diagnosis of Vertically Transmitted HIV Infection," *AIDS* 4:393-398 (1990).

Zachar et al., "Enhanced Chemiluminescence-based Hybridization Analysis for PCR-mediated HIV-1 DNA Detection Offers and Alternative to $^{32}$P-labelled Probes," *Journal of Virological Methods* 133:391-395 (1991).

Zack et al., "HIV-1 Entry into Quiescent Primary Lymphocytes: Molecular Analysis Reveals a Labile, Latent Viral Structure," *Cell* 61:213-222 (1990).

Zagury et al., "Genetic Variability Between Isolates of Human Immunodeficiency Virus (HIV) Type 2 is Comparable to the Variability Among HIV Type 1," *Proc. Natl. Acad. Sci. USA* 85:5941 (1988).

Zoller and Smith, "Oligonucleotide-Directed Mutagenesis of DNA Fragments Cloned into M13 Vectors," *Methods in Enzymology* 100:468-500 (1983).

Arya et al., "New human and simian HIV-related retroviruses possess functional transactivator (*taf*) gene," Nature, 1987, 328:548-550, Macmillan Journals Ltd., London, U.K.

Muesing et al., "Nucleic acid structure and expression of the human AIDS/lymphadenopathy retrovirus," Nature, 1985, 313:450-458, Macmillan Journals Ltd., London, U.K.

Ratner et al., "Polymorphism of the 3' open reading frame of the virus associated with the acquired immune deficiency syndrome, human T-lymphotropic virus type III," Nucl. Acids Res., 1985, 13(22):8219-8229, Oxford University Press, U.K.

Stoflet et al., "Genomic Amplification with Transcript Sequencing," Science, 1988, 239(4839):491-494, American Association for the Advancement of Science, Washington, DC, USA.

Teglbjaerg et al., "Sensitive non-radioactive detection of HIV-1: use of nested primers for the amplification of HIV DNA," Mol. Cell. Probes, 1992, 6(3):175-180, Academic Press, New York, USA.

Wain-Hobson et al., "Nucleotide Sequence of the Aids Virus, LAV," Cell, 1985, 40:9-17, MIT Press Cambridge, U.K.

Database Genbank, Accession No. X05821, Version No. X05821.1, "Human T-lymphotropic retrovirus HTLV-III(B) RNA with 3'-LTR with tar transactivator sequence," Jul. 6, 1989.

Database Genbank, Accession No. M11840, Version No. 11840.1, "Human immunodeficiency virus type 1, vif, tat, rev and nef mRNA (clone 12 cDNA)," Aug. 2, 1993.

Database Genbank, Accession No. X03188, Version No. X03188.1, "Human T-lymphotropic virus type III (HTLV III) 3' ORF HXB3 RNA," Apr. 18, 2005.

Database Genbank, Accession No. X03189, Version No. X03189.1, "Human T-lymphotropic virus type III (HTLV III) C15 RNA for 3'ORF," Apr. 18, 2005.

* cited by examiner

DETECTION OF HIV

This application is a continuation of application Ser. No. 09/168,947, filed Oct. 8, 1998, now U.S. Pat. No. 6,589,734, the contents of which are hereby incorporated by reference herein, which is a continuation-in-part of application Ser. No. 08/469,067, filed Jun. 6, 1995, now U.S. Pat. No. 5,824,518, which is a continuation of application Ser. No. 07/550,837, filed Jul. 10, 1990, now U.S. Pat. No. 5,480,784, which is a continuation-in-part of application Ser. No. 07/379,501, filed Jul. 11, 1989, now abandoned.

FIELD OF THE INVENTION

This invention relates to methods for increasing the number of copies of a specific nucleic acid sequence or "target sequence" which may be present either alone or as a component, large or small, of a homogeneous or heterogeneous mixture of nucleic acids. The mixture of nucleic acids may be that found in a sample taken for diagnostic testing, environmental testing, for research studies, for the preparation of reagents or materials for other processes such as cloning, or for other purposes.

The selective amplification of specific nucleic acid sequences is of value in increasing the sensitivity of diagnostic and environmental assays while maintaining specificity; increasing the sensitivity, convenience, accuracy and reliability of a variety of research procedures; and providing ample supplies of specific oligonucleotides for various purposes.

The present invention is particularly suitable for use in environmental and diagnostic testing due to the convenience with which it may be practiced.

BACKGROUND OF THE INVENTION

The detection and/or quantitation of specific nucleic acid sequences is an increasingly important technique for identifying and classifying microorganisms, diagnosing infectious diseases, detecting and characterizing genetic abnormalities, identifying genetic changes associated with cancer, studying genetic susceptibility to disease, and measuring response to various types of treatment. Such procedures have also found expanding uses in detecting and quantitating microorganisms in foodstuffs, environmental samples, seed stocks, and other types of material where the presence of specific microorganisms may need to be monitored. Other applications are found in the forensic sciences, anthropology, archaeology, and biology where measurement of the relatedness of nucleic acid sequences has been used to identify criminal suspects, resolve paternity disputes, construct genealogical and phylogenetic trees, and aid in classifying a variety of life forms.

A common method for detecting and quantitating specific nucleic acid sequences is nucleic acid hybridization. This method is based on the ability of two nucleic acid strands which contain complementary or essentially complementary sequences to specifically associate, under appropriate conditions, to form a double-stranded structure. To detect and/or quantitate a specific nucleic acid sequence (known as the "target sequence"), a labelled oligonucleotide (known as a "probe") is prepared which contains sequences complementary to those of the target sequence. The probe is mixed with a sample suspected of containing the target sequence, and conditions suitable for hybrid formation are created. The probe hybridizes to the target sequence if it is present in the sample. The probe-target hybrids are then separated from the single-stranded probe in one of a variety of ways. The amount of label associated with the hybrids is measured.

The sensitivity of nucleic acid hybridization assays is limited primarily by the specific activity of the probe, the rate and extent of the hybridization reaction, the performance of the method for separating hybridized and unhybridized probe, and the sensitivity with which the label can be detected. Under the best conditions, direct hybridization methods such as that described above can detect about $1\times10^5$ to $1\times10^6$ target molecules. The most sensitive procedures may lack many of the features required for routine clinical and environmental testing such as speed, convenience, and economy. Furthermore, their sensitivities may not be sufficient for many desired applications. Infectious diseases may be associated with as few as one pathogenic microorganism per 10 ml of blood or other specimen. Forensic investigators may have available only trace amounts of tissue available from a crime scene. Researchers may need to detect and/or quantitate a specific gene sequence that is present as only a tiny fraction of all the sequences present in an organism's genetic material or in the messenger RNA population of a group of cells.

As a result of the interactions among the various components and component steps of this type of assay, there is almost always an inverse relationship between sensitivity and specificity. Thus, steps taken to increase the sensitivity of the assay (such as increasing the specific activity of the probe) may result in a higher percentage of false positive test results. The linkage between sensitivity and specificity has been a significant barrier to improving the sensitivity of hybridization assays. One solution to this problem would be to specifically increase the amount of target sequence present using an amplification procedure. Amplification of a unique portion of the target sequence without requiring amplification of a significant portion of the information encoded in the remaining sequences of the sample could give an increase in sensitivity while at the same time not compromising specificity. For example, a nucleic acid sequence of 25 bases in length has a probability of occurring by chance of 1 in $4^{25}$ or 1 in $10^{15}$ since each of the 25 positions in the sequence may be occupied by one of four different nucleotides.

A method for specifically amplifying nucleic acid sequences termed the "polymerase chain reaction" or "PCR" has been described by Mullis et al. (See U.S. Pat. Nos. 4,683,195, 4,683,202 and 4,800,159 and European patent applications 86302298.4, 86302299.2, and 87300203.4 and *Methods in Enzymology*, Volume 155, 1987, pp. 335–350). The procedure uses repeated cycles of primer-dependent nucleic acid synthesis occurring simultaneously using each strand of a complementary sequence as a template. The sequence which is amplified is defined by the locations of the primer molecules that initiate synthesis. The primers are complementary to the 3'-terminal portion of the target sequence or its complement and must complex with those sites in order for nucleic acid synthesis to begin. After extension product synthesis, the strands are separated, generally by thermal denaturation, before the next synthesis step. In the PCR procedure, copies of both strands of a complementary sequence are synthesized.

The strand separation step used in PCR to separate the newly synthesized strands at the conclusion of each cycle of the PCR reaction is often thermal denaturation. As a result, either a thermostable enzyme is required or new enzyme must be added between thermal denaturation steps and the initiation of the next cycle of DNA synthesis. The requirement of repeated cycling of reaction temperature between several different and extreme temperatures is a disadvantage of the PCR procedure. In order to make the PCR convenient, expensive programmable thermal cycling instruments are required.

The PCR procedure has been coupled to RNA transcription by incorporating a promoter sequence into one of the primers used in the PCR reaction and then, after amplification by the PCR procedure for several cycles, using the double-stranded DNA as template for the transcription of single-stranded RNA. (See, e.g. Murakawa et al., DNA 7:287–295 (1988).

Other methods for amplification of a specific nucleic acid sequence comprise a series of primer hybridization, extending and denaturing steps to provide an intermediate double stranded DNA molecule containing a promoter sequence through the use of a primer. The double stranded DNA is used to produce multiple RNA copies of the target sequence. The resulting RNA copies can be used as target sequences to produce further copies and multiple cycles can be performed. (See, e.g., Burg, et al., WO 89/1050 and Gingeras, et al., WO 88/10315.)

Methods for chemically synthesizing relatively large amounts of DNA of a specified sequence in vitro are well known to those skilled in the art; production of DNA in this way is now commonplace. However, these procedures are time-consuming and cannot be easily used to synthesize oligonucleotides much greater in length than about 100 bases. Also, the entire base sequence of the DNA to be synthesized must be known. These methods require an expensive instrument capable of synthesizing only a single sequence at one time. Operation of this instrument requires considerable training and expertise. Methods for the chemical synthesis of RNA have been more difficult to develop.

Nucleic acids may be synthesized by techniques which involve cloning or insertion of specific nucleic acid sequences into the genetic material of microorganisms so that the inserted sequences are replicated when the organism replicates. If the sequences are inserted next to and downstream from a suitable promoter sequence, RNA copies of the sequence or protein products encoded by the sequence may be produced. Although cloning allows the production of virtually unlimited amounts of specific nucleic acid sequences, due to the number of manipulations involved it may not be suitable for use in diagnostic, environmental, or forensic testing. Use of cloning techniques requires considerable training and expertise. The cloning of a single sequence may consume several man-months of effort or more.

Relatively large amounts of certain RNAs may be made using a recombinant single-stranded-RNA molecule having a recognition sequence for the binding of an RNA-directed polymerase, preferably Qβ replicase. (See, e.g., U.S. Pat. No. 4,786,600 to Kramer, et al.) A number of steps are required to insert the specific sequence into a DNA copy of the variant molecule, clone it into an expression vector, transcribe it into RNA and then replicate it with Qβ replicase.

SUMMARY OF THE INVENTION

The present invention is directed to novel methods of synthesizing multiple copies of a target nucleic acid sequence which are autocatalytic (i.e., able to cycle automatically without the need to modify reaction conditions such as temperature, pH, or ionic strength and using the product of one cycle in the next one).

The present method includes (a) treating an RNA target sequence with a first oligonucleotide which comprises a first primer which has a complexing sequence sufficiently complementary to the 3'-terminal portion of the target to complex therewith and which optionally has a sequence 5' to the priming sequence which includes a promoter for an RNA polymerase under conditions whereby an oligonucleotide/target sequence complex is formed and DNA synthesis may be initiated, (b) extending the first primer in an extension reaction using the target as a template to give a first DNA primer extension product complementary to the RNA target, (c) separating the DNA extension product from the RNA target using an enzyme which selectively degrades the RNA target; (d) treating the DNA primer extension product with a second oligonucleotide which comprises a primer or a splice template and which has a complexing sequence sufficiently complementary to the 3'-terminal portion of the DNA primer extension product to complex therewith under conditions whereby an oligonucleotide/target sequence complex is formed and DNA synthesis may be initiated, provided that if the first oligonucleotide does not have a promoter, then the second oligonucleotide is a splice template which has a sequence 5' to the complexing sequence which includes a promoter for an RNA polymerase; (e) extending the 3'-terminus of either the second oligonucleotide or the first primer extension product, or both, in a DNA extension reaction to produce a template for the RNA polymerase; and (f) using the template to produce multiple RNA copies of the target sequence using an RNA polymerase which recognizes the promoter sequence. The oligonucleotide and RNA copies may be used to autocatalytically synthesize multiple copies of the target sequence.

In one aspect of the present invention, the general method includes (a) treating an RNA target sequence with a first oligonucleotide which comprises a first primer which has a complexing sequence sufficiently complementary to the 3'-terminal portion of the target to complex therewith and which has a sequence 5' to the complexing sequence which includes a promoter for an RNA polymerase under conditions whereby an oligonucleotide/target complex is formed and DNA synthesis may be initiated, (b) extending the first primer in an extension reaction using the target as a template to give a first DNA primer extension product complementary to the RNA target, (c) separating the first DNA primer extension product from the RNA target using an enzyme which selectively degrades the RNA target; (d) treating the DNA primer extension product with a second oligonucleotide which comprises a second primer which has a complexing sequence sufficiently complementary to the 3'-terminal portion of the DNA primer extension product to complex therewith under conditions whereby an oligonucleotide/target complex is formed and DNA synthesis may be initiated; (e) extending the 3'-terminus of the second primer in a DNA extension reaction to give a second DNA primer extension product, thereby producing a template for the RNA polymerase; and (f) using the template to produce multiple RNA copies of the target sequence using an RNA polymerase which recognizes the promoter sequence. The oligonucleotide and RNA copies may be used to autocatalytically synthesize multiple copies of the target sequence. This aspect further includes: (g) treating an RNA copy from step (f) with the second primer under conditions whereby an oligonucleotide/target sequence complex is formed and DNA synthesis may be initiated; (h) extending the 3' terminus of the second primer in a DNA extension reaction to give a second DNA primer extension product using the RNA copy as a template; (i) separating the second DNA primer extension product from the RNA copy using an enzyme which selectively degrades the RNA copy; (j) treating the second DNA primer extension product with the first primer under conditions whereby an oligonucleotide/target sequence complex is formed and DNA synthesis may be initiated; (k) extending the 3' terminus of the second primer extension product in a DNA extension reaction to produce a template for an RNA polymerase; and (l) using the template of step (k) to produce multiple copies of the target sequence using an RNA polymerase which recognizes the promoter. Using the RNA copies of step (l), steps (g) to (k) may be autocatalytically repeated to synthesize multiple copies of the target sequence. The first primer which in step (k) acts as a splice template may also be extended in the DNA extension reaction of step (k).

Another aspect of the general method of the present invention provides a method which comprises (a) treating an RNA target sequence with a first primer which has a complexing sequence sufficiently complementary to the 3' terminal portion of the target sequence to complex therewith under conditions whereby an oligonucleotide/target sequence complex is formed and DNA synthesis may be initiated; (b) extending the 3' terminus of the primer in an extension reaction using the target as a template to give a DNA primer extension product complementary to the RNA target; (c) separating the DNA extension product from the RNA target using an enzyme which selectively degrades the RNA target; (d) treating the DNA primer extension product with a second oligonucleotide which comprises a splice template which has a complexing sequence sufficiently complementary to the 3'-terminus of the primer extension product to complex therewith and a sequence 5' to the complexing sequence which includes a promoter for an RNA polymerase under conditions whereby an oligonucleotide/target sequence complex is formed and DNA synthesis may be initiated; (e) extending the 3' terminus of the DNA primer extension product to add thereto a sequence complementary to the promoter, thereby producing a template for an RNA polymerase; (f) using the template to produce multiple RNA copies of the target sequence using an RNA polymerase which recognizes the promoter sequence; and (g) using the RNA copies of step (f), autocatalytically repeating steps (a) to (f) to amplify the target sequence. Optionally, the splice template of step (d) may also function as a primer and in step (e) be extended to give a second primer extension product using the first primer extension product as a template.

In addition, in another aspect of the present invention, where the sequence sought to be amplified is present as DNA, use of an appropriate Preliminary Procedure generates RNA copies which may then be amplified according to the General Method of the present invention.

Accordingly, in another aspect, the present invention is directed to Preliminary Procedures for use in conjunction with the amplification method of the present invention which not only can increase the number of copies present to be amplified, but also can provide RNA copies of a DNA sequence for amplification.

The present invention is directed to methods for increasing the number of copies of a specific target nucleic acid sequence in a sample. In one aspect, the present invention involves cooperative action of a DNA polymerase (such as a reverse transcriptase) and a DNA-dependent RNA polymerase (transcriptase) with an enzymatic hybrid-separation step to produce products that may themselves be used to produce additional product, thus resulting in an autocatalytic reaction without requiring manipulation of reaction conditions such as thermal cycling. In some embodiments of the methods of the present invention which include a Preliminary Procedure, all but the initial step(s) of the preliminary procedure are carried out at one temperature.

The methods of the present invention may be used as a component of assays to detect and/or quantitate specific nucleic acid target sequences in clinical, environmental, forensic, and similar samples or to produce large numbers of copies of DNA and/or RNA of specific target sequence for a variety of uses. These methods may also be used to produce multiple DNA copies of a DNA target sequence for cloning or to generate probes or to produce RNA and DNA copies for sequencing.

In one example of a typical assay, a sample to be amplified is mixed with a buffer concentrate containing the buffer, salts, magnesium, nucleotide triphosphates, primers and/or splice templates, dithiothreitol, and spermidine. The reaction is then optionally incubated near 100° C. for two minutes to denature any secondary structure. After cooling to room temperature, if the target is a DNA target without a defined 3' terminus, reverse transcriptase is added and the reaction mixture is incubated for 12 minutes at 42° C. The reaction is again denatured near 100° C., this time to separate the primer extension product from the DNA template. After cooling, reverse transcriptase, RNA polymerase, and RNAse H are added and the reaction is incubated for two to four hours at 37° C. The reaction can then be assayed by denaturing the product, adding a probe solution, incubating 20 minutes at 60° C., adding a solution to selectively hydrolyze the unhybridized probe, incubating the reaction six minutes at 60° C., and measuring the remaining chemiluminescence in a luminometer. (See, e.g., Arnold, et al., International Publication No. WO 89/02476, published Mar. 23, 1989, International Application No. PCT/US88/03195, filed Sep. 21, 1988, the disclosure of which is incorporated herein by reference and is referred to as "HPA"). The products of the methods of the present invention may be used in many other assay systems known to those skilled in the art.

If the target has a defined 3' terminus or the target is RNA, a typical assay includes mixing the target with the buffer concentrate mentioned above and denaturing any secondary structure. After cooling, reverse transcriptase, RNA polymerase, and RNAse H are added and the mixture is incubated for two to four hours at 37° C. The reaction can then be assayed as described above.

The methods of the present invention and the materials used therein may be incorporated as part of diagnostic kits for use in diagnostic procedures.

DEFINITIONS

As used herein, the following terms have the following meanings unless expressly stated to the contrary.

1. Template

A "template" is a nucleic acid molecule that is being copied by a nucleic acid polymerase. A template may be either single-stranded, double-stranded or partially double-stranded, depending on the polymerase. The synthesized copy is complementary to the template or to at least one strand of a double-stranded or partially double-stranded template. Both RNA and DNA are always synthesized in the 5' to 3' direction and the two strands of a nucleic acid duplex always are aligned so that the 5' ends of the two strands are at opposite ends of the duplex (and, by necessity, so then are the 3' ends).

2. Primer, Splice Template

A "primer" is an oligonucleotide that is complementary to a template which complexes (by hydrogen bonding or hybridization) with the template to give a primer/template complex for initiation of synthesis by a DNA polymerase, and which is extended by the addition of covalently bonded bases linked at its 3' end which are complementary to the template in the process of DNA synthesis. The result is a primer extension product. Virtually all DNA polymerases (including reverse transcriptases) that are known require complexing of an oligonucleotide to a single-stranded template ("priming") to initiate DNA synthesis, whereas RNA replication and transcription (copying of RNA from DNA) generally do not require a primer. Under appropriate circumstances, a primer may act as a splice template as well (see definition of "splice template" that follows).

A "splice template" is an oligonucleotide that complexes with a single-stranded nucleic acid and is used as a template to extend the 3' terminus of a target nucleic acid to add a specific sequence. The splice template is sufficiently complementary to the 3' terminus of the target nucleic acid molecule, which is to be extended, to complex therewith. A DNA- or RNA-dependent DNA polymerase is then used to extend the target nucleic acid molecule using the sequence 5' to the complementary region of the splice template as a template. The extension product of the extended molecule has the specific sequence at its 3'-terminus which is complementary to the sequence at the 5'-terminus of the splice template.

If the 3' terminus of the splice template is not blocked and is complementary to the target nucleic acid, it may also act as a primer and be extended by the DNA polymerase using the target nucleic acid molecule as a template. The 3' terminus of the splice template can be blocked in a variety of ways, including having a 3'-terminal dideoxynucleotide or a 3'-terminal sequence non-complementary to the target, or in other ways well known to those skilled in the art.

Either a primer or a splice template may complex with a single-stranded nucleic acid and serve a priming function for a DNA polymerase.

3. Target Nucleic Acid, Target Sequence

A "target nucleic acid" has a "target sequence" to be amplified, and may be either single-stranded or double-stranded and may include other sequences besides the target sequence which may not be amplified.

The term "target sequence" refers to the particular nucleotide sequence of the target nucleic acid which is to be amplified. The "target sequence" includes the complexing sequences to which the oligonucleotides (primers and/or splice template) complex during the processes of the present invention. Where the target nucleic acid is originally single-stranded, the term "target sequence" will also refer to the sequence complementary to the "target sequence" as present in the target nucleic acid. Where the "target nucleic acid" is originally double-stranded, the term "target sequence" refers to both the (+) and (−) strands.

4. Promoter/Promoter Sequence

A "promoter sequence" is a specific nucleic acid sequence that is recognized by a DNA-dependent RNA polymerase ("transcriptase") as a signal to bind to the nucleic acid and begin the transcription of RNA at a specific site. For binding, such transcriptases generally require DNA which is double-stranded in the portion comprising the promoter sequence and its complement; the template portion (sequence to be transcribed) need not be double-stranded. Individual DNA-dependent RNA polymerases recognize a variety of different promoter sequences which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence.

5. DNA-dependent DNA Polymerase

A "DNA-dependent DNA polymerase" is an enzyme that synthesizes a complementary DNA copy from a DNA template. Examples are DNA polymerase I from *E. coli* and bacteriophage T7 DNA polymerase. All known DNA-dependent DNA polymerases require a complementary primer to initiate synthesis. It is known that under suitable conditions a DNA-dependent DNA polymerase may synthesize a complementary DNA copy from an RNA template.

6. DNA-dependent RNA Polymerase (Transcriptase)

A "DNA-dependent RNA polymerase" or "transcriptase" is an enzyme that synthesizes multiple RNA copies from a double-stranded or partially-double stranded DNA molecule having a (usually double-stranded) promoter sequence. The RNA molecules ("transcripts") are synthesized in the 5'→3' direction beginning at a specific position just downstream of the promoter. Examples of transcriptases are the DNA-dependent RNA polymerase from *E. coli* and bacteriophages T7, T3, and SP6.

7. RNA-dependent DNA Polymerase (Reverse Transcriptase)

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates.

8. RNAse H

An "RNAse H" is an enzyme that degrades the RNA portion of an RNA:DNA duplex. RNAse H's may be endonucleases or exonucleases. Most reverse transcriptase enzymes normally contain an RNAse H activity in addition to their polymerase activity. However, other sources of the RNAse H are available without an associated polymerase activity. The degradation may result in separation of RNA from a RNA:DNA complex. Alternatively, the RNAse H may simply cut the RNA at various locations such that portions of the RNA melt off or permit enzymes to unwind portions of the RNA.

9. Plus/Minus Strand(s)

Discussions of nucleic acid synthesis are greatly simplified and clarified by adopting terms to name the two complementary strands of a nucleic acid duplex. Traditionally, the strand encoding the sequences used to produce proteins or structural RNAs was designated as the "plus" strand and its complement the "minus" strand. It is now known that in many cases, both strands are functional, and the assignment of the designation "plus" to one and "minus" to the other must then be arbitrary. Nevertheless, the terms are very useful for designating the sequence orientation of nucleic acids and will be employed herein for that purpose.

10. Hybridize, Hybridization

The terms "hybridize" and "hybridization" refer to the formation of complexes between nucleotide sequences which are sufficiently complementary to form complexes via Watson-Crick base pairing. Where a primer (or splice template) "hybridizes" with target (template), such complexes (or hybrids) are sufficiently stable to serve the priming function required by the DNA polymerase to initiate DNA synthesis.

11. Primer Sequences

The sequences of the primers referred to herein are set forth below.

```
HBV region 2 primers
(+): 5'CACCAAATGCCCCTATCTTATCAACACTTCCGG3'
(-): 5'AATTTAATACGACTCACTATAGGGAGACCCGAGATTGAGATCTTCTGCGAC3'
Probe
(+): 5'GGTCCCCTAGAAGAAGAACTCCCTCG3'

HIV region 1 primers
(+): 5'AATTTAATACGACTCACTATAGGGAGACAAGGGACTTTCCGCTGGGGACTTTCC3'
(-): 5'GTCTAACCAGAGAGACCCAGTACAGGC3'
Probe
sequence:
5'GCAGCTGCTTATATGCAGGATCTGAGGG3'

HIV region 2 primers
(+): 5'AATTTAATACGACTCACTATAGGGAGACAAATGGCAGTATTCATCCACA3'
(-): 5'CCCTTCACCTTTCCAGAG3'
Probe
sequence:
(-): 5'CTACTATTCTTTCCCCTGCACTGTACCCC3'

HIV region 3 primers
(+): 5'CTCGACGCAGGACTCGGCTTGCTG3'
(-): 5'AATTTAATACGACTCACTATAGGGAGACTCCCCCGCTTAATACTGACGCT3'
Probe:
(+): 5'GACTAGCGGAGGCTAGAAGGAGAGAGATGGG3'

HIV region 4 primers
(+): 5'AATTTAATACGACTCACTATAGGGAGAGACCATCAATGAGGAAGCTGCAGAATG3'
(-): 5'CCATCCTATTTGTTCCTGAAGGGTAC3'
Probe:
(-): 5'CTTCCCCTTGGTTCTCTCATCTGGCC3'

HIV region 5 primers
(+): 5'GGCAAATGGTACATCAGGCCATATCACCTAG3'
(-): 5'AATTTAATACGACTCACTATAGGGAGAGGGGTGGCTCCTTCTGATAATGCTG3'
Probe:
5'GAAGGCTTTCAGCCCAGAAGTAATACCCATG3'

BCL-2 chromosomal translocation major breakpoint t(14;18)
primers
(-): 5'GAATTAATACGACTCACTATAGGGAGACCTGAGGAGACGGTGACC3'
(+): 5'TATGGTGGTTTGACCTTTAG3'
Probes:
5'GGCTTTCTCATGGCTGTCCTTCAG3'
5'GGTCTTCCTGAAATGCAGTGGTCG3'

CML chromosomal translocation t(9;22) primers
(-): 5'GAATTAATACGACTCACTATAGGGAGACTCAGACCCTGAGGCTCAAAGTC3'
(+): 5'GGAGCTGCAGATGCTGACCAAC3'
Probe:
5'GCAGAGTTCAAAAGCCCTTCAGCGG3'
```

12. Specificity

Characteristic of a nucleic acid sequence which describes its ability to distinguish between target and non-target sequences dependent on sequence and assay conditions.

DETAILED DESCRIPTION OF THE INVENTION

Figure 1A:
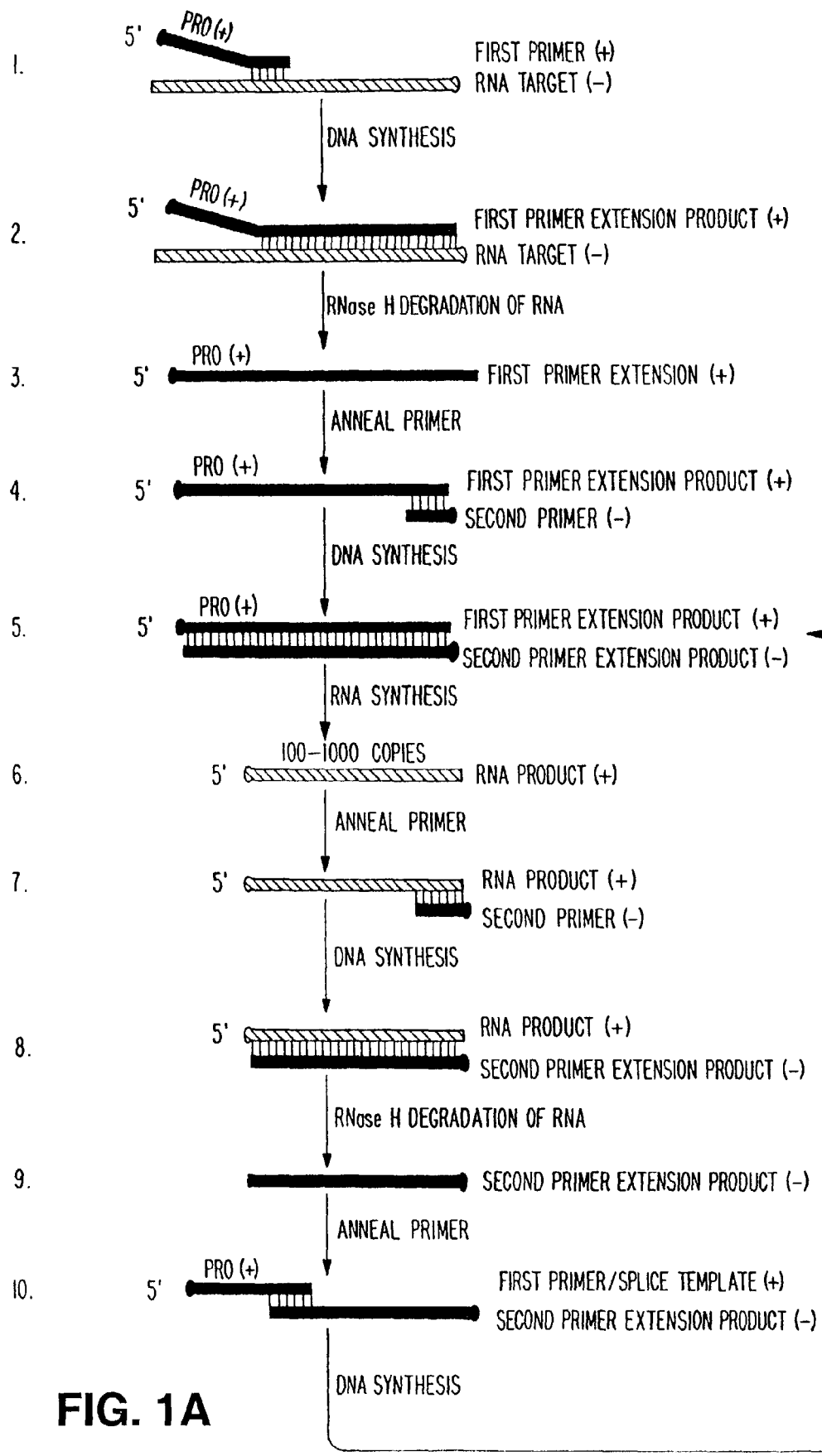
FIGS. 1A to 1O depict the General Methods of the present invention.

In accordance with the present invention, novel methods and compositions are provided for the amplification of specific nucleic acid target sequences for use in assays for the detection and/or quantitation of specific nucleic acid target sequences or for the production of large numbers of copies of DNA and/or RNA of specific target sequences for a variety of uses.

I. General Method

In a preferred aspect, the present invention provides an autocatalytic amplification method which synthesizes large numbers of DNA and RNA copies of an RNA target sequence. The target nucleic acid contains the target sequence to be amplified. The target sequence is that region of the target nucleic acid which is defined on either end by the primers, splice templates, and/or the natural target nucleic acid termini and includes both the (+) and (−) strands.

In one aspect, this method comprises treating a target nucleic acid comprising an RNA target sequence with a first oligonucleotide which comprises a first primer which has a complexing sequence sufficiently complementary to the 3'-terminal portion of the target sequence to complex therewith and which optionally has a sequence 5' to the complexing sequence which includes a promoter sequence for an RNA polymerase under conditions whereby an oligonucleotide/target sequence complex is formed and DNA synthesis may be initiated. The first oligonucleotide primer may also have other sequences 5' to the priming sequence. The 3'-end of the first primer is extended by an appropriate DNA polymerase in an extension reaction using the RNA as a template to give a first DNA primer extension product which is complementary to the RNA template. The first primer extension product is separated (at least partially) from the RNA template using an enzyme which selectively degrades the RNA template. Suitable enzymes are those which selectively act on the RNA strand of an RNA-DNA complex and include enzymes which comprise an RNAse H. Although some reverse transcriptases include an RNAse H activity, it may be preferable to add exogenous RNAse H, such as an E. coli RNAse H.

The single-stranded first primer extension product is treated with a second oligonucleotide which comprises a second primer or a splice template which has a complexing sequence sufficiently complementary to the 3'-terminal portion of target sequence contained in the first primer extension product to complex therewith, under conditions whereby an oligonucleotide/target sequence complex is formed and DNA synthesis may be initiated. If the first primer does not have a promoter then the second oligonucleotide is a splice template which has a sequence 5' to the complexing region which includes a promoter for an RNA polymerase. Optionally, the splice template may be blocked at its 3' terminus. The 3' terminus of the second oligonucleotide and/or the primer extension product is extended in a DNA extension reaction to produce a template for a RNA polymerase. The RNA copies or transcripts produced may autocatalytically multiply without further manipulation.

Where an oligonucleotide functions as a splice template, its primer function is not required. Thus, the 3' terminus of the splice template may be either blocked or unblocked. The components of the resulting reaction mixture (i.e., an RNA target which allows production of a first primer extension product with a defined 3' terminus, a first primer, and a splice template either blocked or unblocked) function to autocatalytically synthesize large quantities of RNA and DNA.

In one aspect of the present invention, the first and second oligomers both are primers. The first primer has a sequence 5' to the complexing sequence which includes a promoter for a RNA polymerase and may include other sequences. The second primer may also include a sequence 5' to the complexing sequence which may include a promoter for an RNA polymerase and optionally other sequences. Where both primers have a promoter sequence, it is preferred that both sequences are recognized by the same RNA polymerase unless it is intended to introduce the second promoter for other purposes, such as cloning. The 3'-end of the second primer is extended by an appropriate DNA polymerase in an extension reaction to produce a second DNA primer extension product complementary to the first primer extension product. Note that as the first primer defined one end of the target sequence, the second primer now defines the other end. The double-stranded product of the second extension reaction is a suitable template for the production of RNA by an RNA polymerase. If the second primer also has a promoter sequence, transcripts complementary to both strands of the double-stranded template will be produced during the autocatalytic reaction. The RNA transcripts may now have different termini than the target nucleic acid, but the sequence between the first primer and the second primer remains intact. The RNA transcripts so produced may automatically recycle in the above system without further manipulation. Thus, this reaction is autocatalytic.

If the complexing sequence of the second primer complexes with the 3' terminus of the first primer extension product, the second primer may act as a splice template and the first primer extension product may be extended to add any sequence of the second primer 5' to the priming sequence to the first primer extension product. (See, e.g., FIGS. 1E and 1G) If the second primer acts as a splice template and includes a promoter sequence 5' to the complexing sequence, extension of the first primer extension product to add the promoter sequence produces an additional template for an RNA polymerase which may be transcribed to produce RNA copies of either strand. (See FIGS. 1E and 1G) Inclusion of promoters in both primers may enhance the number of copies of the target sequence synthesized.

Another aspect of the general method of the present invention includes using a first oligonucleotide which comprises a primer and a second oligonucleotide which comprises a splice template and which may or may not be capable of acting as a primer per se (in that it is not itself extended in a primer extension reaction). This aspect of the general method comprises treating a target nucleic acid comprising an RNA target sequence with a first oligonucleotide primer which has a complexing sequence sufficiently complementary to the 3' terminal portion of the target sequence to complex therewith under conditions whereby an oligonucleotide/target sequence complex is formed and DNA synthesis may be initiated. The first primer may have other sequences 5' to the complexing sequence, including a promoter. The 3' end of the first primer is extended by an appropriate DNA polymerase in an extension reaction using the RNA as a template to give a first primer extension product which is complementary to the RNA template. The first primer extension product is separated from the RNA template using an enzyme which selectively degrades the RNA template. Suitable enzymes are those which selectively act on the RNA strand of an RNA-DNA complex and include enzymes which comprise an RNAse H activity. Although some reverse transcriptases include an RNase H activity, it may be preferable to add exogenous RNAse H, such as an E. coli RNAse H. The single stranded first primer extension product is treated with a splice template which has a complexing sequence sufficiently complementary to the 3'-terminus of the primer extension product to complex therewith and a sequence 5' to the complexing sequence which includes a promoter for an RNA polymerase under conditions whereby an oligonucleotide/target sequence complex is formed and DNA synthesis may be initiated. The 3' terminus of the splice template may be either blocked (such as by addition of a dideoxynucleotide) or uncomplementary to the target nucleic acid (so that it does not function as a primer) or alternatively unblocked. The 3' terminus of the first primer extension product is extended using an appropriate DNA polymerase in a DNA extension reaction to add to the 3' terminus of the first primer extension product a sequence complementary to the sequence of the splice template 5' to the complexing sequence which includes the promoter. If the 3' terminus is unblocked, the splice template may be extended to give a second primer extension product complementary to the first primer extension product. The product of the extension reaction with the splice template (whether blocked or unblocked) can function as a template for RNA synthesis using an RNA polymerase which recognizes the promoter. As noted above, RNA transcripts so produced may automatically recycle in the above system without further manipulation. Thus, the reaction is autocatalytic.

In some embodiments, the target sequence to be amplified is defined at both ends by the location of specific sequences complementary to the primers (or splice templates) employed. In other embodiments, the target sequence is defined at one location of a specific sequence, complementary to a primer molecule employed and, at the opposite end, by the location of a specific sequence that is cut by a specific restriction endonuclease, or by other suitable means, which may include a natural 3' terminus. In other embodiments, the target sequence is defined at both ends by the location of specific sequences that are cut by one or more specific restriction endonuclease(s).

In a preferred embodiment of the present invention, the RNA target sequence is determined and then analyzed to determine where RNAse H degradation will cause cuts or removal of sections of RNA from the duplex. Analyses can be conducted to determine the effect of the RNAse degradation of the target sequence by RNAse H present in AMV reverse transcriptase and MMLV reverse transcriptase, by *E. coli* RNAse H or other sources and by combinations thereof.

In selecting a primer set, it is preferable that one of the primers be selected so that it will hybridize to a section of RNA which is substantially nondegraded by the RNAse H present in the reaction mixture. If there is substantial degradation, the cuts in the RNA strand in the region of the primer may inhibit initiation of DNA synthesis and prevent extension of the primer. Thus, it is preferred to select a primer which will hybridize with a sequence of the RNA target, located so that when the RNA is subjected to RNAse H, there is no substantial degradation which would prevent formation of the primer extension product.

The site for hybridization of the promoter-primer is chosen so that sufficient degradation of the RNA strand occurs to permit removal of the portion of the RNA strand hybridized to the portion of the DNA strand to which the promoter-primer will hybridize. Typically, only portions of RNA are removed from the RNA:DNA duplex through RNAse H degradation and a substantial part of the RNA strand remains in the duplex.

Formation of the promoter-containing double stranded product for RNA synthesis is illustrated in FIG. 4. As illustrated in FIG. 4, the target RNA strand hybridizes to a primer which is selected to hybridize with a region of the RNA strand which is not substantially degraded by RNAse H present in the reaction mixture. The primer is then extended to form a DNA strand complementary to the RNA strand. Thereafter, the RNA strand is cut or degraded at various locations by the RNAse H present in the reaction mixture. It is to be understood that this cutting or degradation can occur at this point or at other times during the course of the reaction. Then the RNA fragments dissociate from the DNA strand in regions where significant cuts or degradation occur. The promoter-primer then hybridizes to the DNA strand at its 3' end, where the RNA strand has been substantially degraded and separated from the DNA strand. Next, the DNA strand is extended to form a double strand DNA promoter sequence, thus forming a template for RNA synthesis. It can be seen that this template contains a double-stranded DNA promoter sequence. When this template is treated with RNA polymerase, multiple strands of RNA are formed.

Although the exact nature of the RNA degradation resulting from the RNAse H is not known, it has been shown that the result of RNAse H degradation on the RNA strand of an RNA:DNA hybrid resulted in dissociation of small pieces of RNA from the hybrid. It has also been shown that promoter-primers can be selected which will bind to the DNA after RNAse H degradation at the area where the small fragments are removed.

FIGS. 1 and 2, as drawn, do not show the RNA which may remain after RNAse H degradation. It is to be understood that although these figures generally show complete removal of RNA from the DNA:RNA duplex, under the preferred conditions only partial removal occurs as illustrated in FIG. 3. By reference to FIG. 1A, it can be seen that the proposed mechanism may not occur if a substantial portion of the RNA strand of FIG. 1 remains undegraded thus preventing hybridization of the second primer or extension of the hybridized second primer to produce a DNA strand complementary to the promoter sequence. However, based upon the principles of synthesis discovered and disclosed in this application, routine modifications can be made by those skilled in the art according to the teachings of this invention to provide an effective and efficient procedure for amplification of RNA.

Figure 2A:
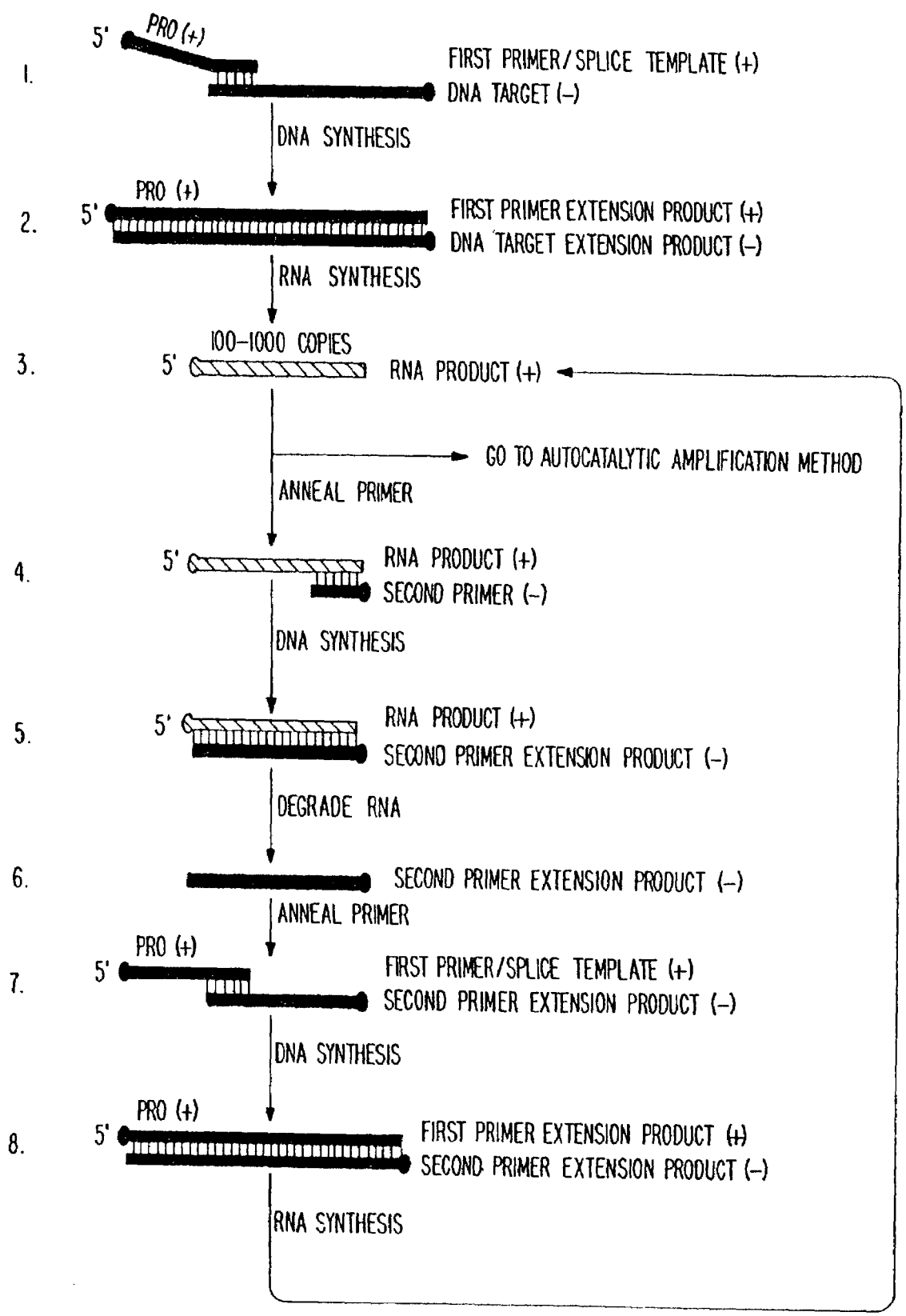
FIGS. 2A to 2E depict the embodiment of the present invention referred to as Preliminary Procedure I.

As may be seen from the descriptions herein and FIGS. 1A to 1O, the method of the present invention embraces optional variations.

FIG. 1A depicts a method according to the present invention wherein the target nucleic acid has additional sequences 3' to the target sequence. The first oligonucleotide comprises a first primer having a promoter 5' to its complexing sequence which complexes with the 3' terminal portion of the target sequence of a target nucleic acid (RNA) which has additional sequences 3' to the end of the target sequence. The second oligonucleotide comprises a second primer which complexes with the 3' terminal portion of the first primer extension product, coinciding with the 3' terminus of the first primer extension product. In step (1), the first primer does not act as a splice template due to the additional sequences 3' to the target sequence; however, in step (10), the first primer can act as a splice template, since the second primer extension product does not have additional sequences 3' to the target sequence.

Figure 1B:
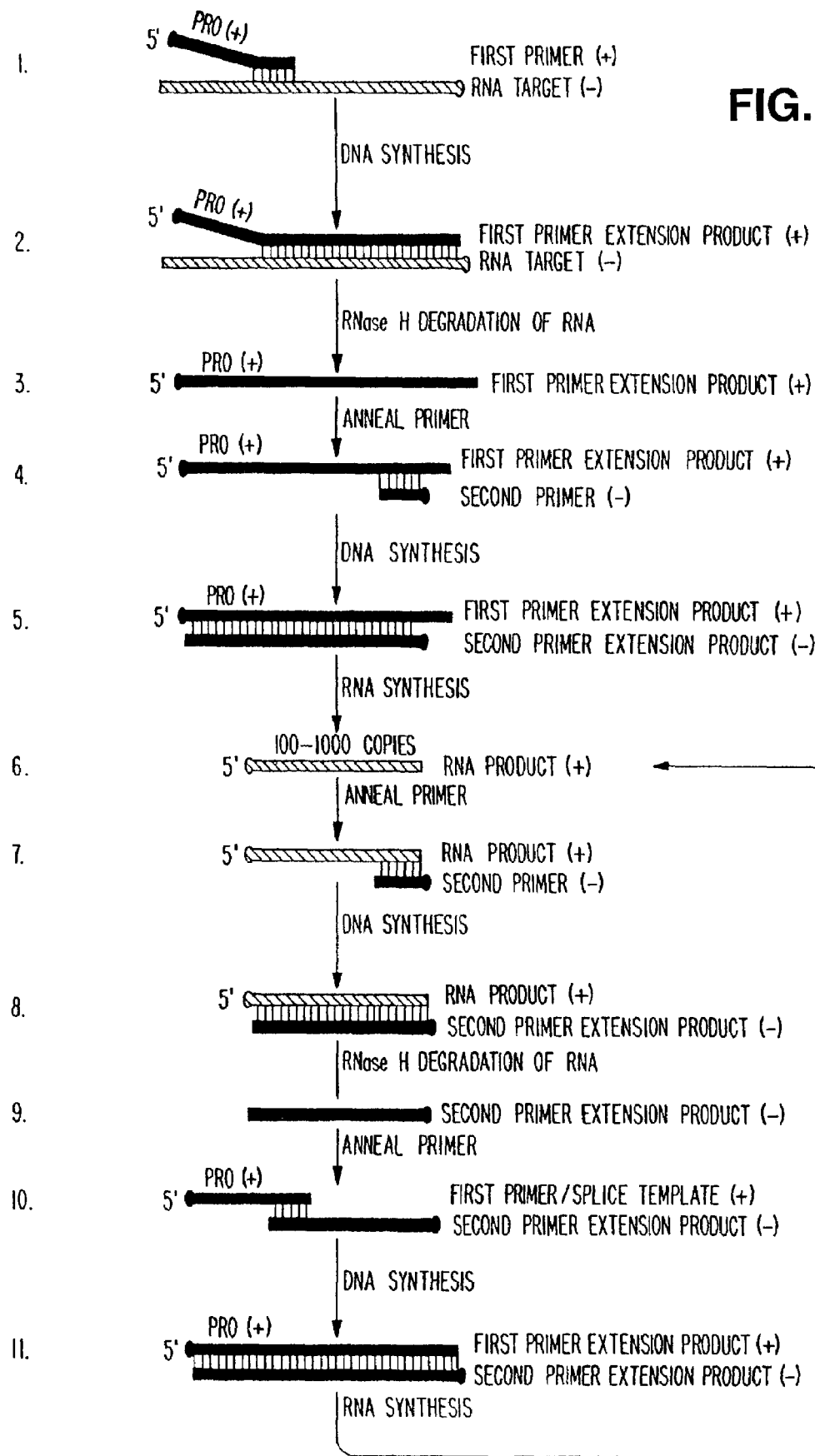

FIG. 1B depicts a method according to the present invention wherein the target nucleic acid (RNA) has additional sequences both 5' and 3' to the target sequence. The first oligonucleotide is as depicted in FIG. 1A. The second oligonucleotide comprises a primer which complexes to the 3' terminal portion of the target sequence of the first primer extension product which has additional sequences 3' to the target sequence.

Figure 1C:
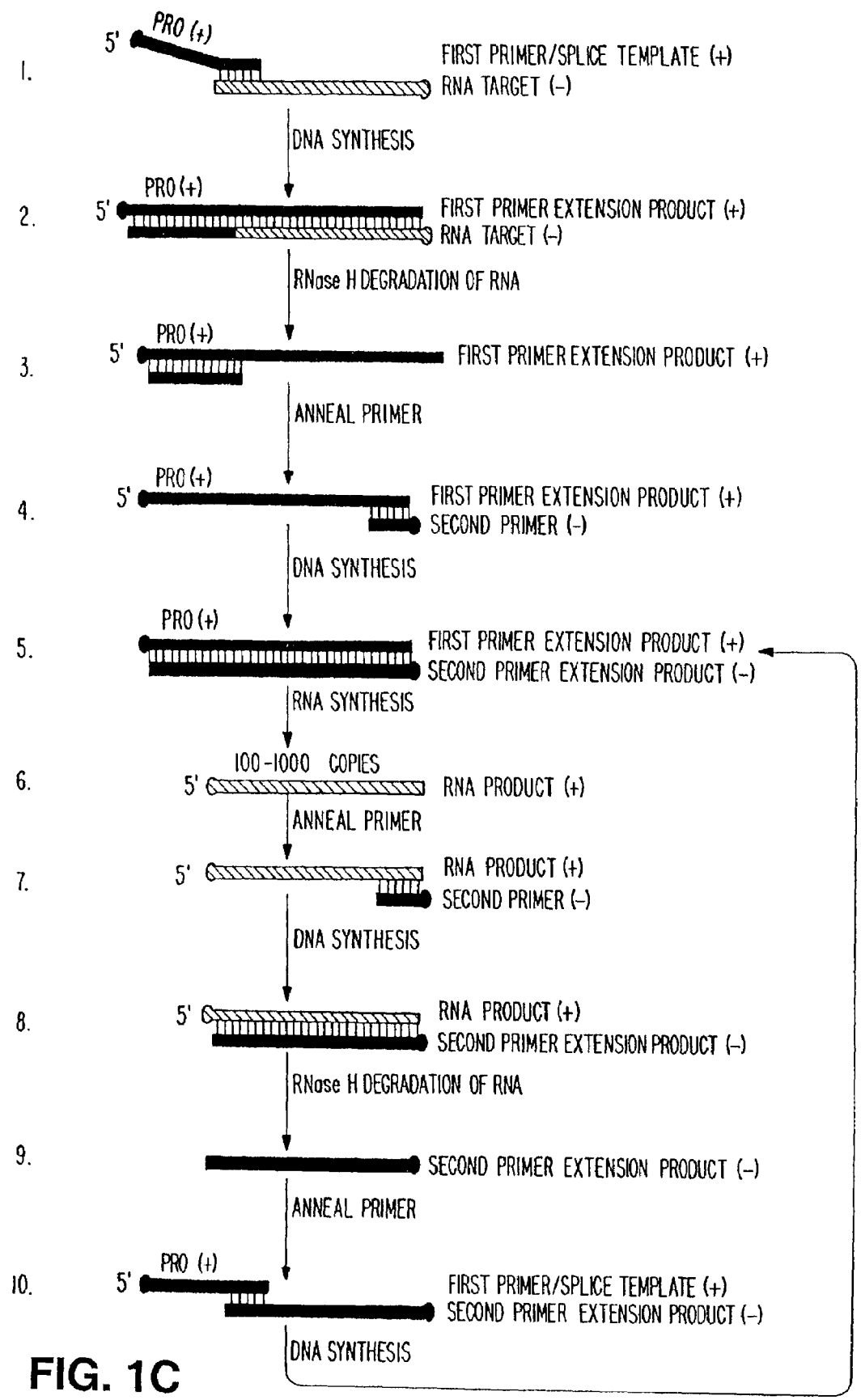

FIG. 1C depicts a target nucleic acid (RNA) which has defined 5' and 3' ends and, thus, has no additional sequences either 5' or 3' to the target sequence. The first oligonucleotide is as depicted in FIGS. 1A and 1B, but since it complexes with the 3' terminus of the target nucleic acid, it acts as both a primer and splice template in Step 1. The second-oligonucleotide is as depicted in FIG. 1A.

Figure 1D:
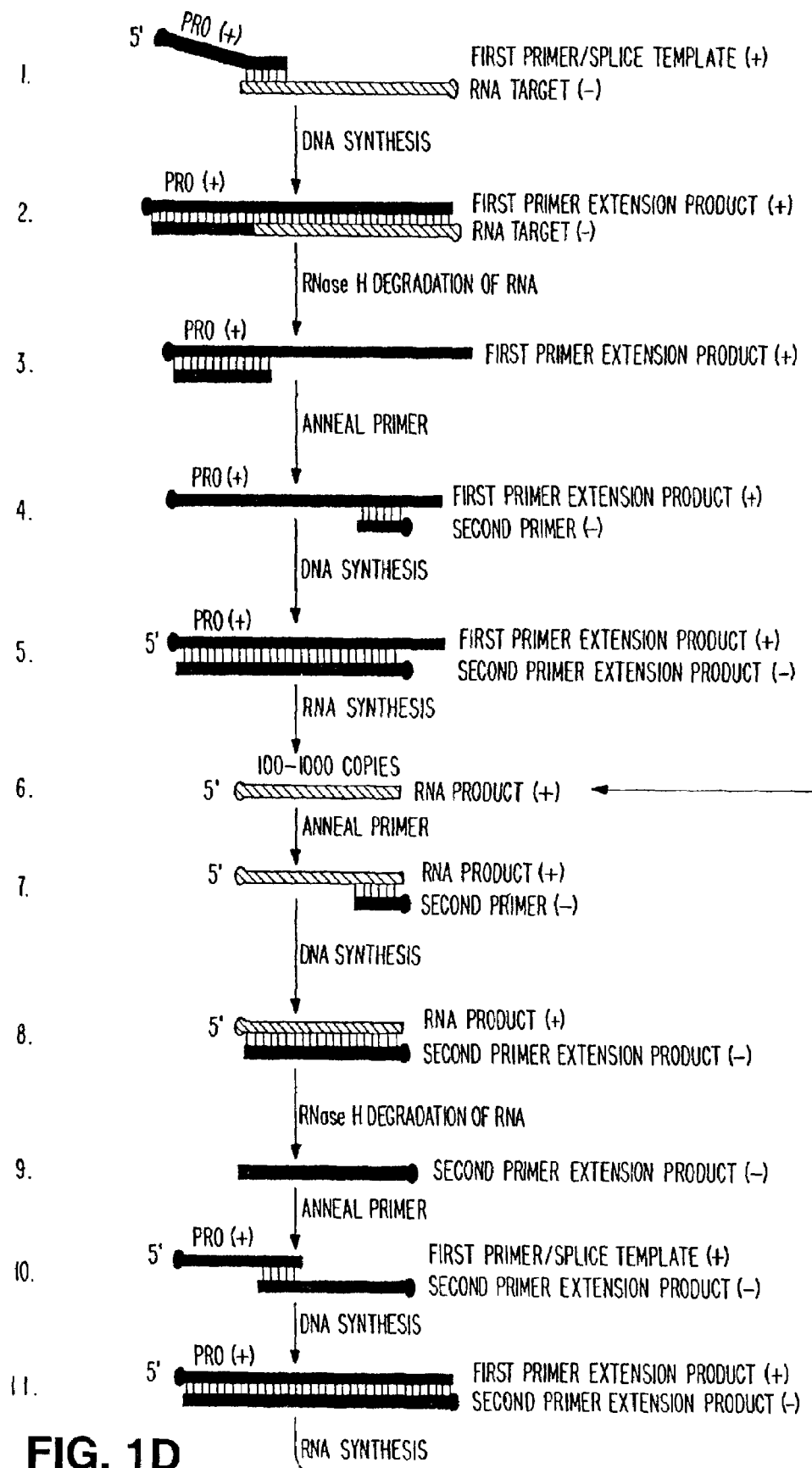

FIG. 1D depicts a target nucleic acid (RNA) having a defined 3' end and, thus, has no additional sequences 3' to the target sequence, but does have additional sequences 5' to the target sequence. The first oligonucleotide is as, depicted in FIG. 1C and functions as both a primer and a splice template. The second oligonucleotide is as depicted in FIG. 1B.

Figure 1E:
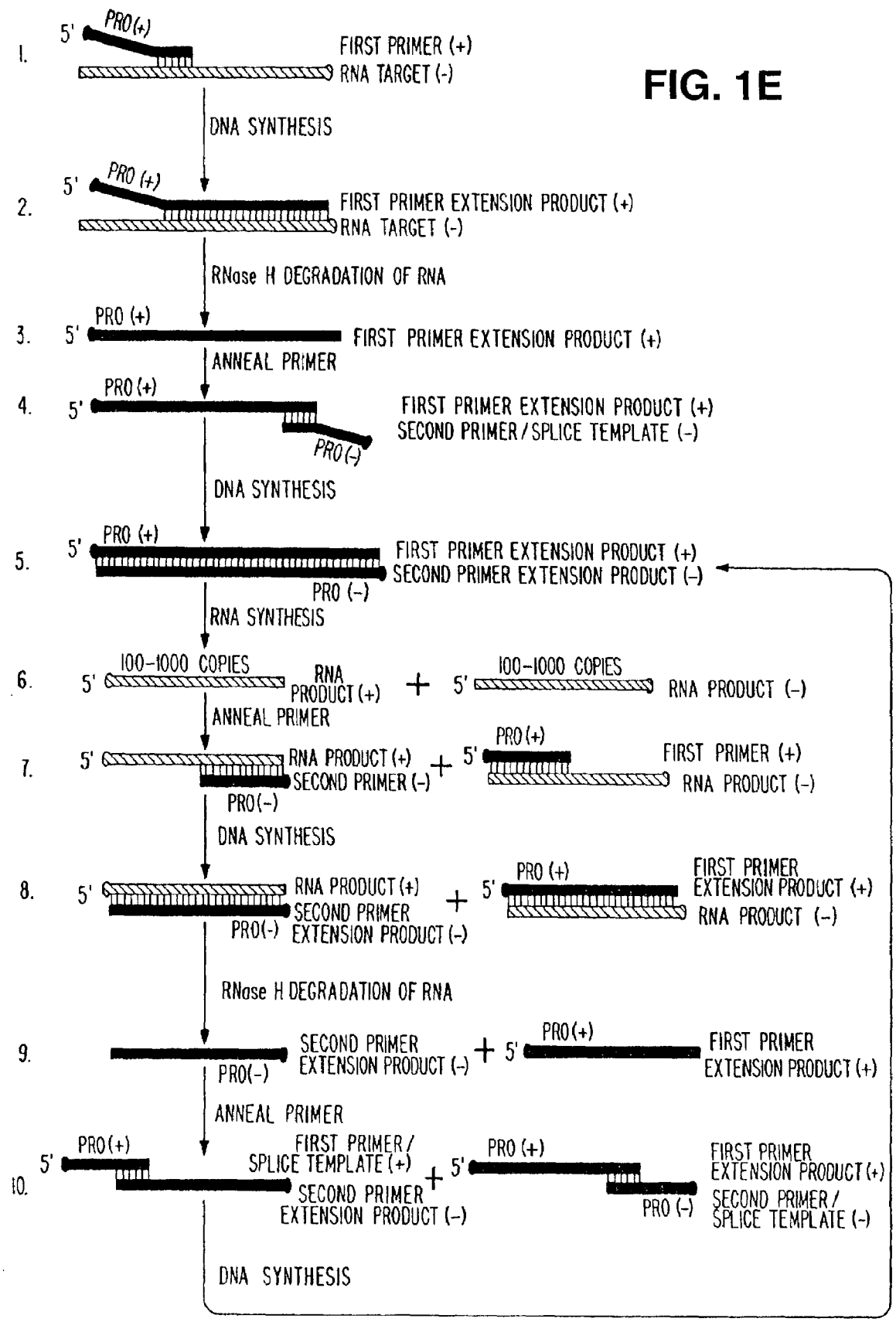

FIG. 1E depicts a target nucleic acid (RNA) which has a defined 5' end but which has additional sequences 3' to the target sequence. The first oligonucleotide is as depicted in FIG. 1A. The second oligonucleotide comprises a second primer which, since it complexes with the 3'-terminus of the first primer extension product, also comprises a splice template. The second oligonucleotide also has a promoter 5' to its complexing sequence.

Figure 1F:
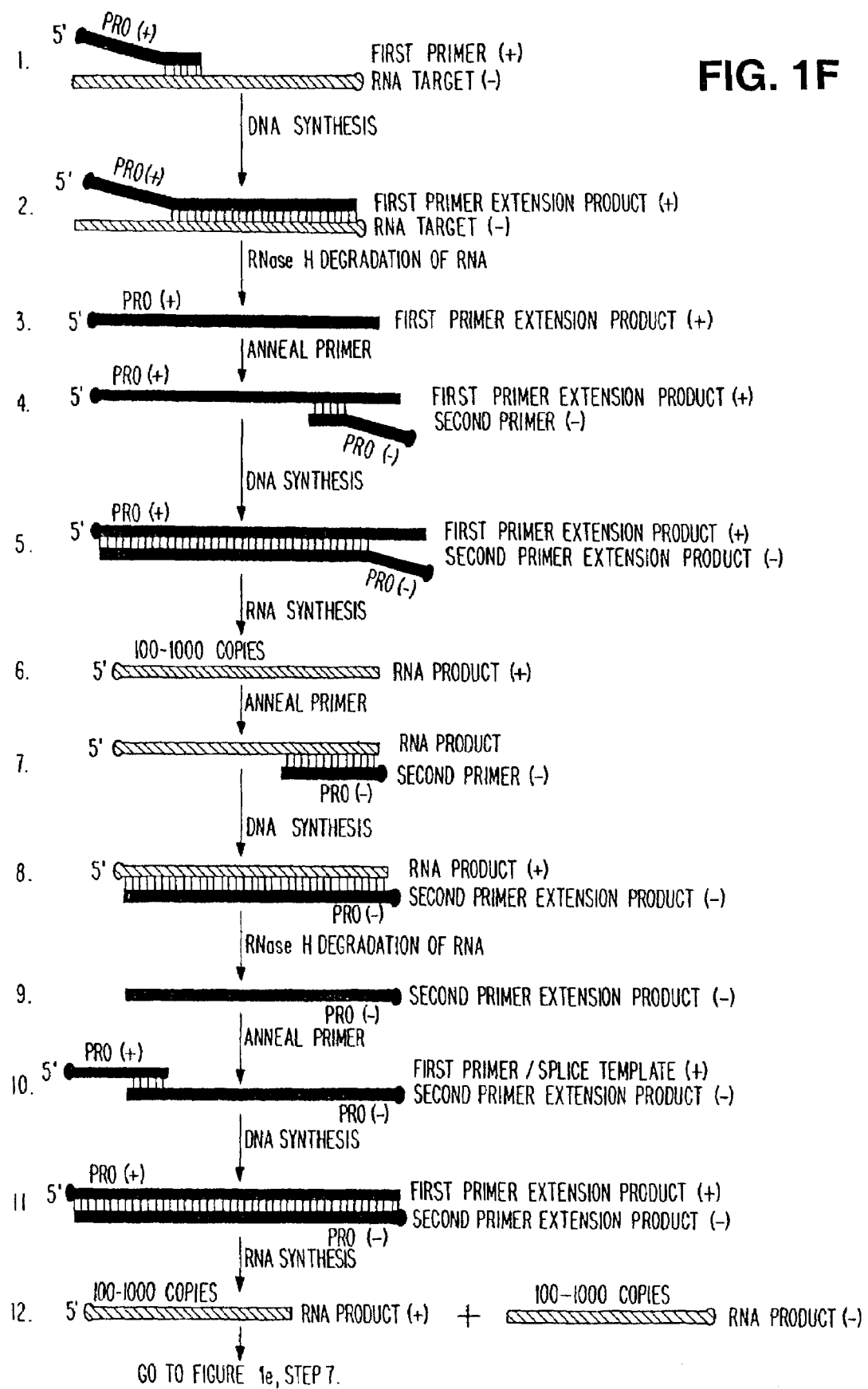

FIG. 1F depicts a target nucleic acid (RNA) having additional sequences both 5' and 3' to the target sequence. The first oligonucleotide is as depicted in FIG. 1A. The second oligonucleotide is as depicted in FIG. 1E, except it cannot act as a splice template in step (4), since the first primer extension product has additional sequences 3' to the target sequence.

Figure 1G:
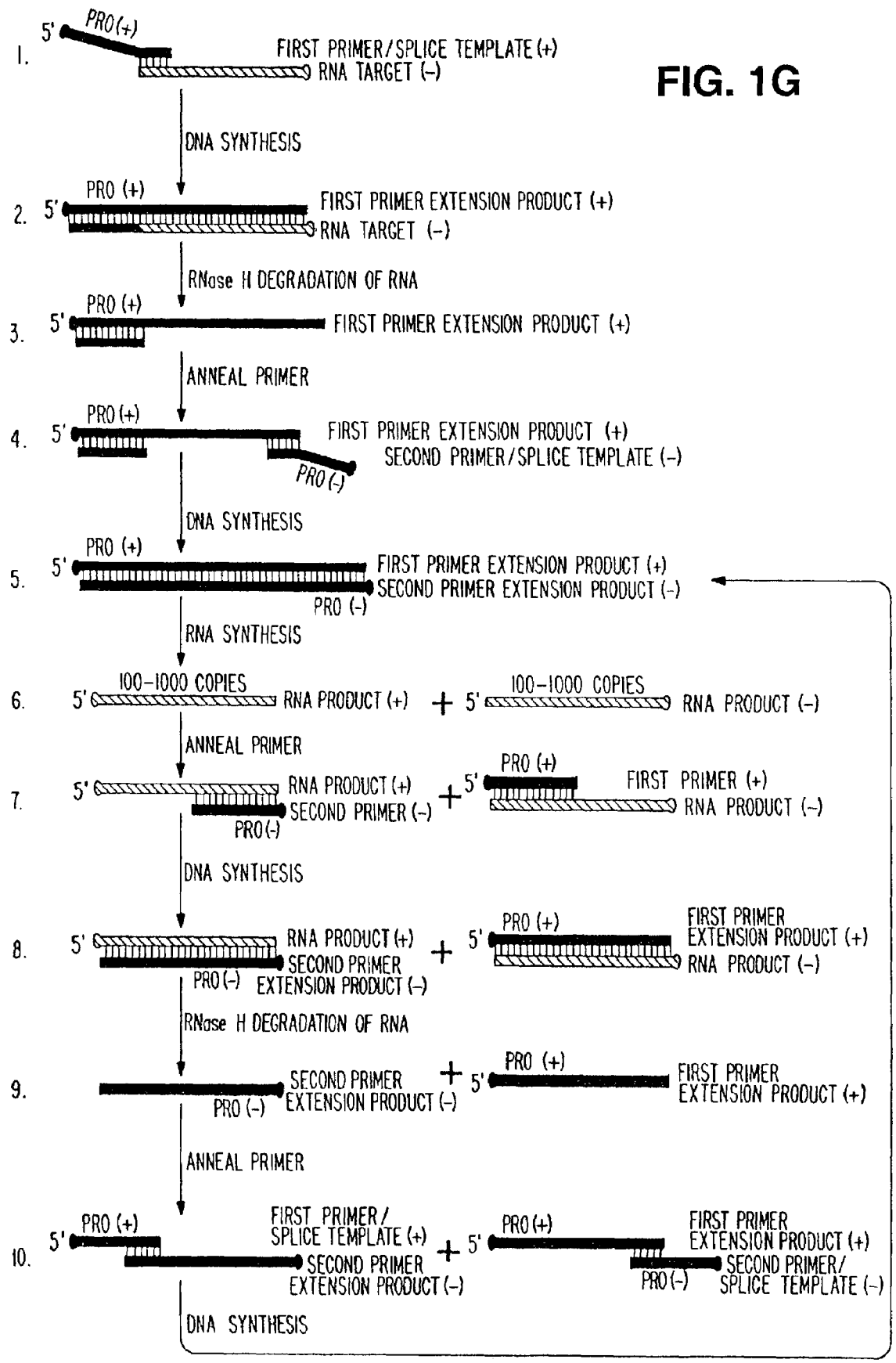

FIG. 1G depicts a target nucleic acid (RNA) which has both defined 5' and 3' ends, having no sequences besides the target sequence. The first oligonucleotide is as depicted in FIG. 1C and the second oligonucleotide as depicted in FIG. 1E. Since the target has no additional sequences, both oligonucleotides also act as splice templates.

Figure 1H:
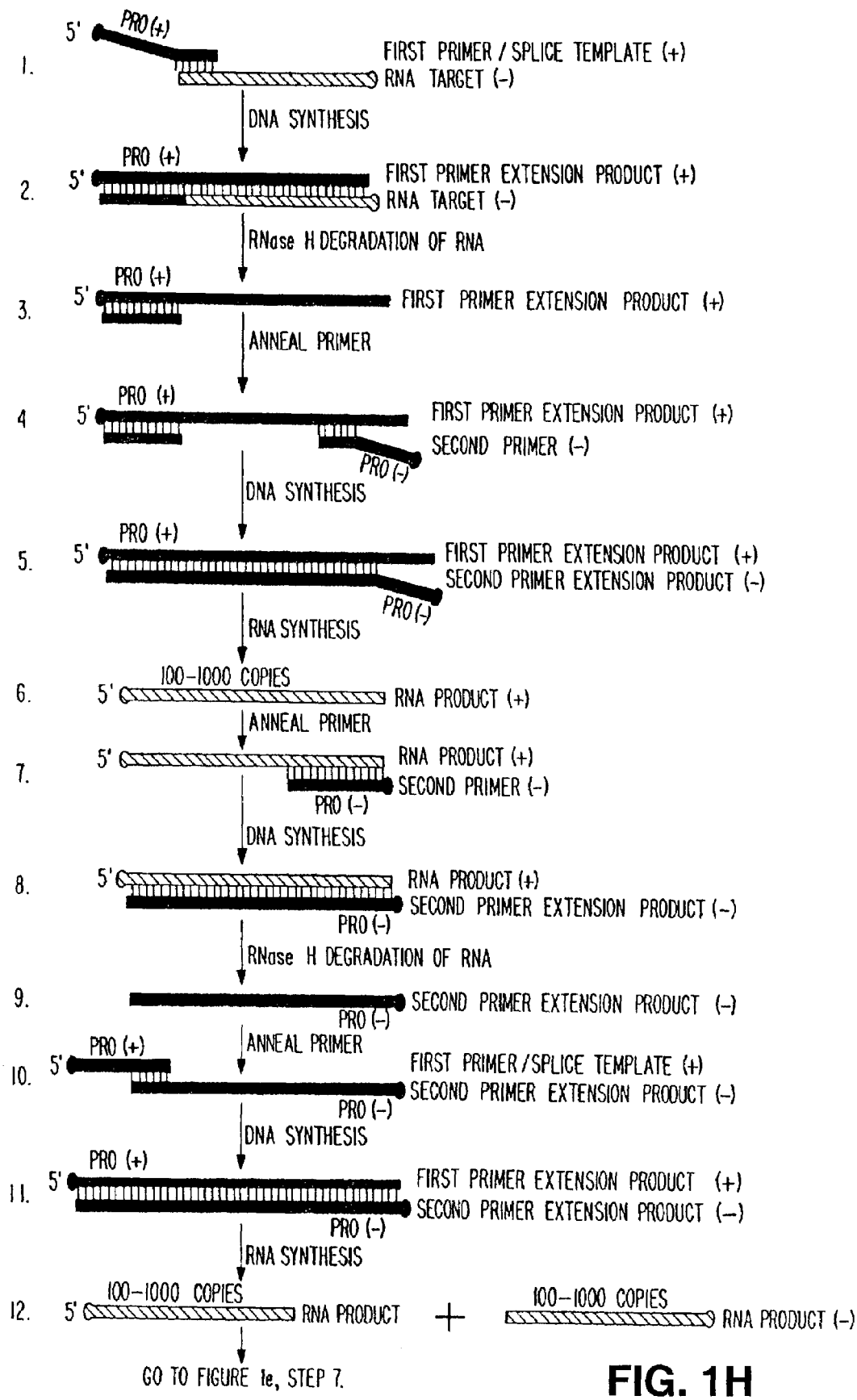

FIG. 1H depicts a target nucleic acid (RNA) which has a defined 3' end, having no sequences 3' to the target sequence, but has additional sequences 5' to the target sequence. The first oligonucleotide is as depicted in FIGS. 1C and 1G and acts as both a primer and splice template. The second oligonucleotide is as depicted in FIG. 1F.

Figure 1I:
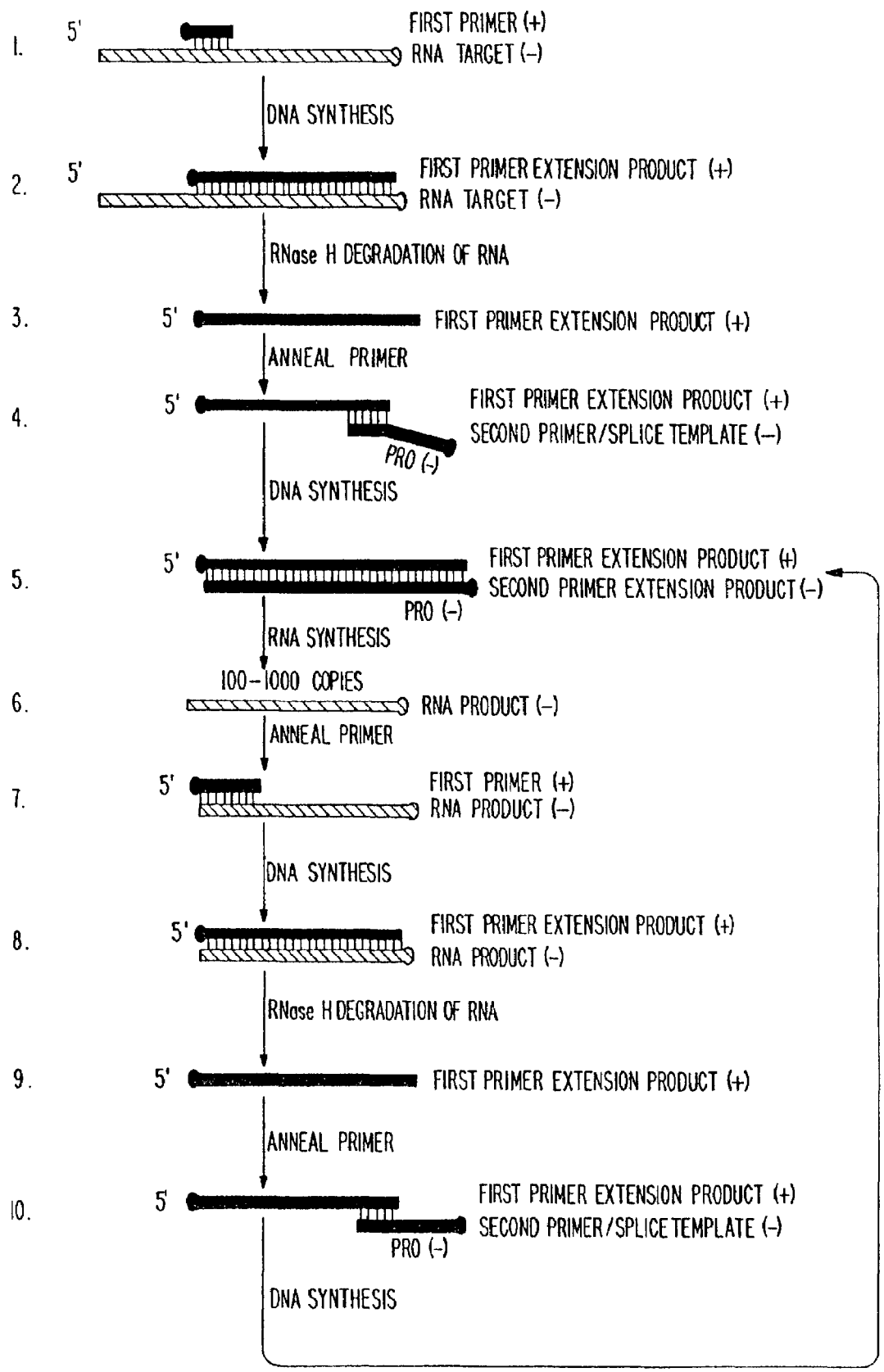

FIG. 1I depicts a target nucleic acid (RNA) which has a defined 5' terminus and has no additional sequences 5' to the target sequence, but has additional sequences 3' to the target sequence. The first oligonucleotide comprises a primer without a promoter. The second oligonucleotide comprises an unblocked splice template which has a promoter 5' to its complexing sequence.

Figure 1J:
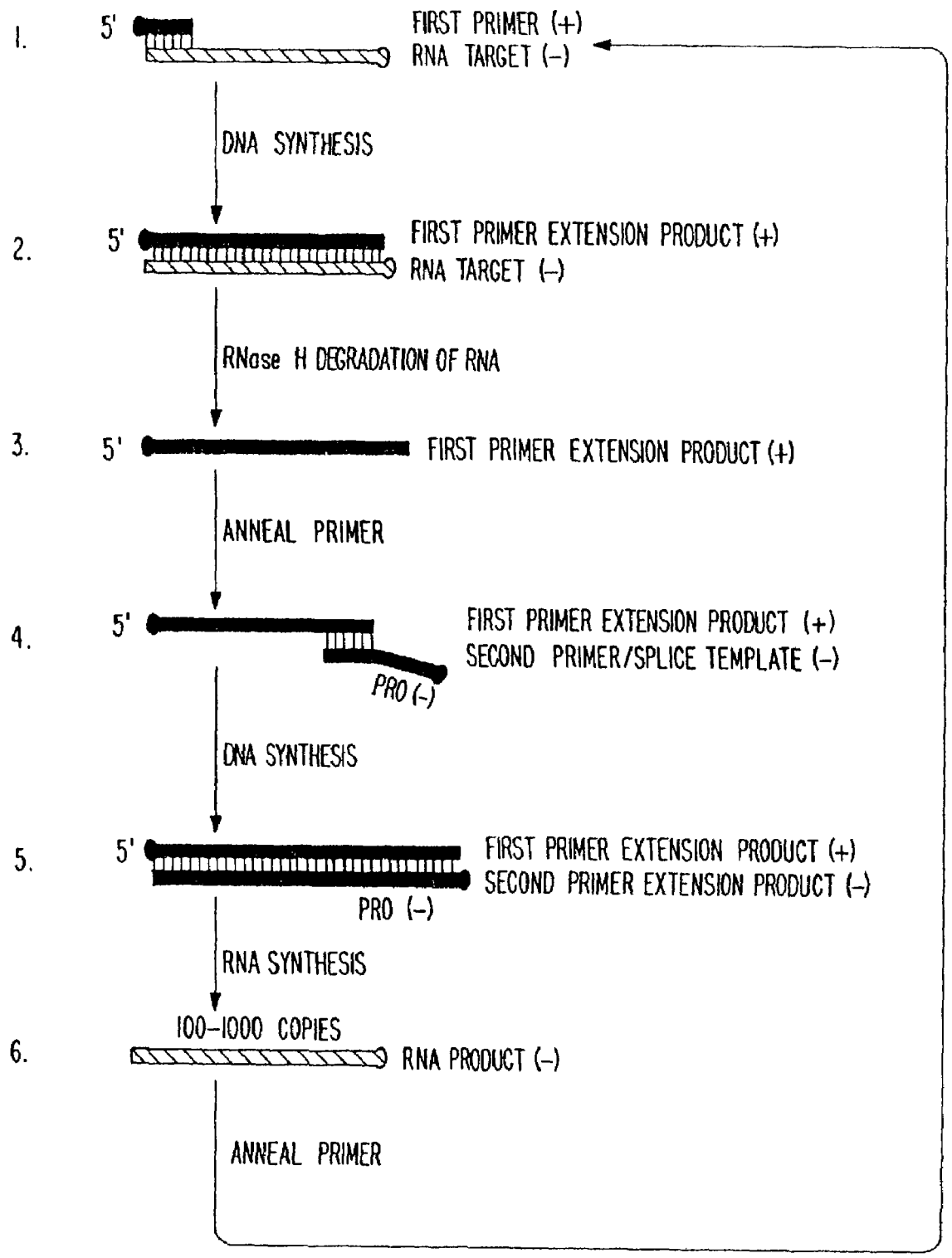

FIG. 1J depicts a target nucleic acid (RNA) which has defined 5' and 3' terminus and no sequences besides the target sequence. The first oligonucleotide comprises a primer without a promoter. The second oligonucleotide is as depicted in FIG. 1I.

Figure 1K:
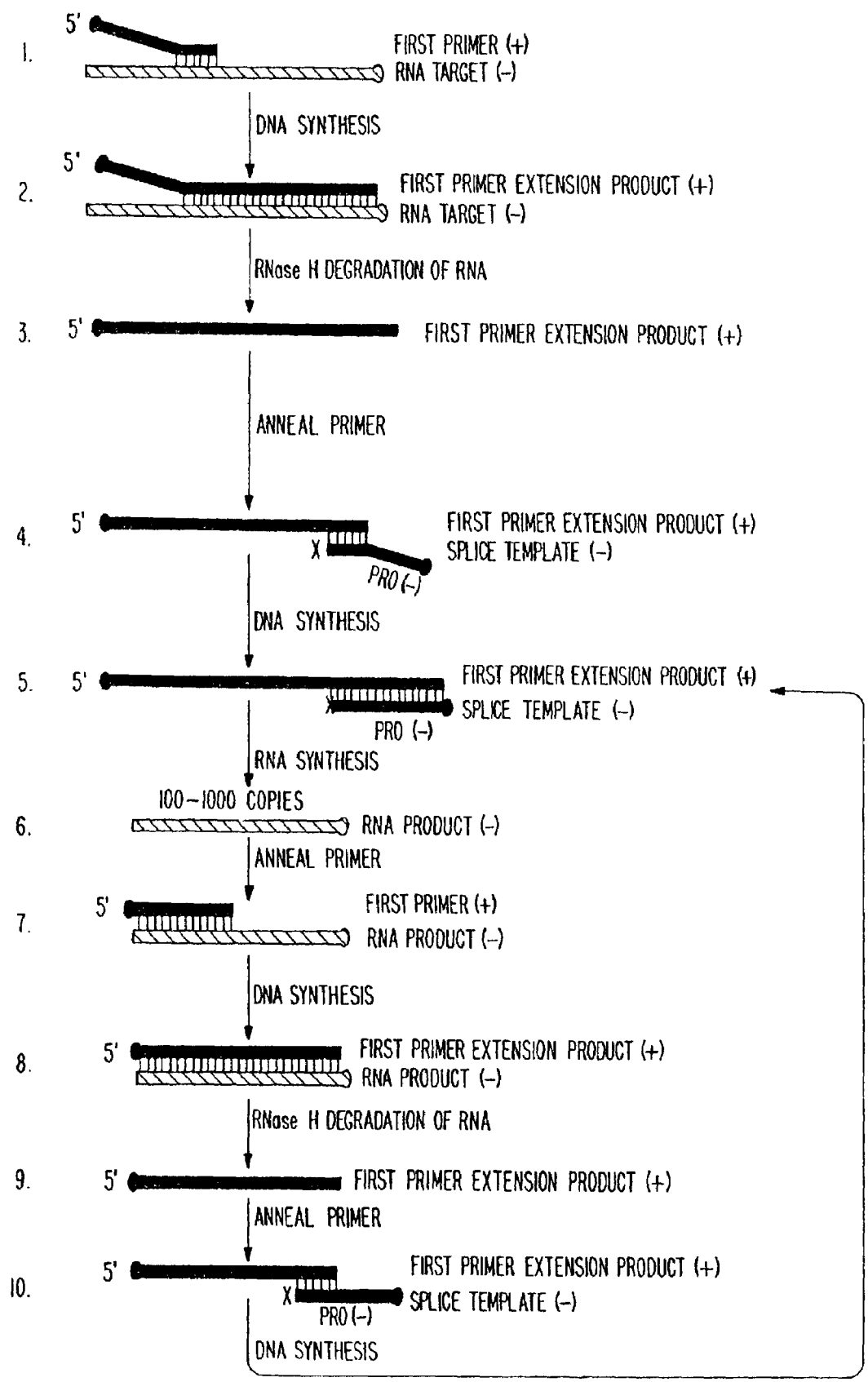

FIG. 1K depicts a target nucleic acid (RNA) which has a defined 5' terminus with no additional sequence 5' to the target sequence, but which has additional sequences 3' to the target sequence. The second oligonucleotide comprises a splice template having a promoter 5' to its completing sequence, but which is blocked at its 3' terminus. The second oligonucleotide is incapable of acting as a primer.

Figure 1L:
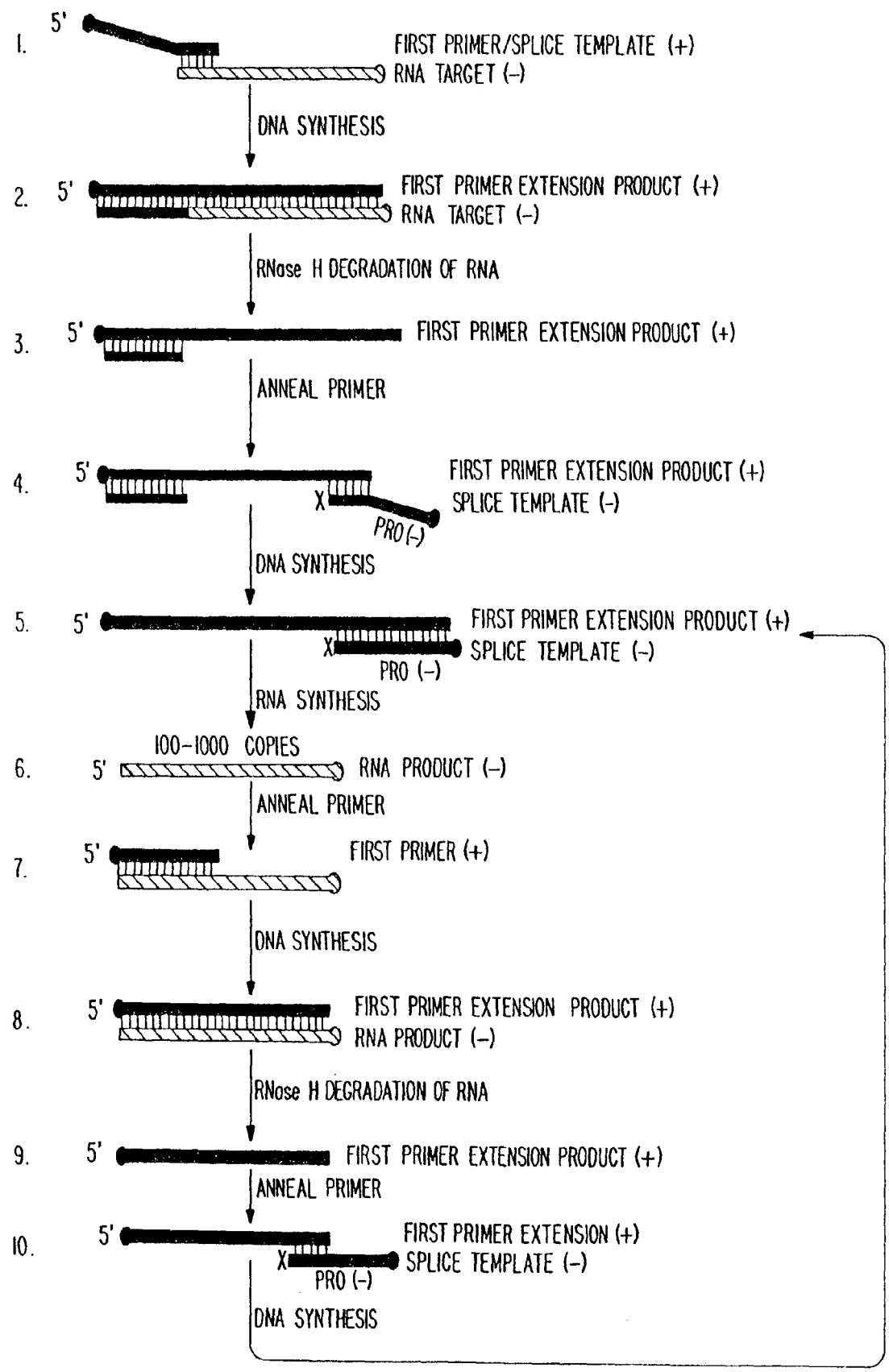

FIG. 1L depicts a target nucleic acid (RNA) which has defined 5' and 3' ends and no additional sequences besides the target sequence. The first oligonucleotide acts as both a primer and a splice template. The second oligonucleotide is a blocked splice template and is as depicted in FIG. 1K.

Figure 1M:
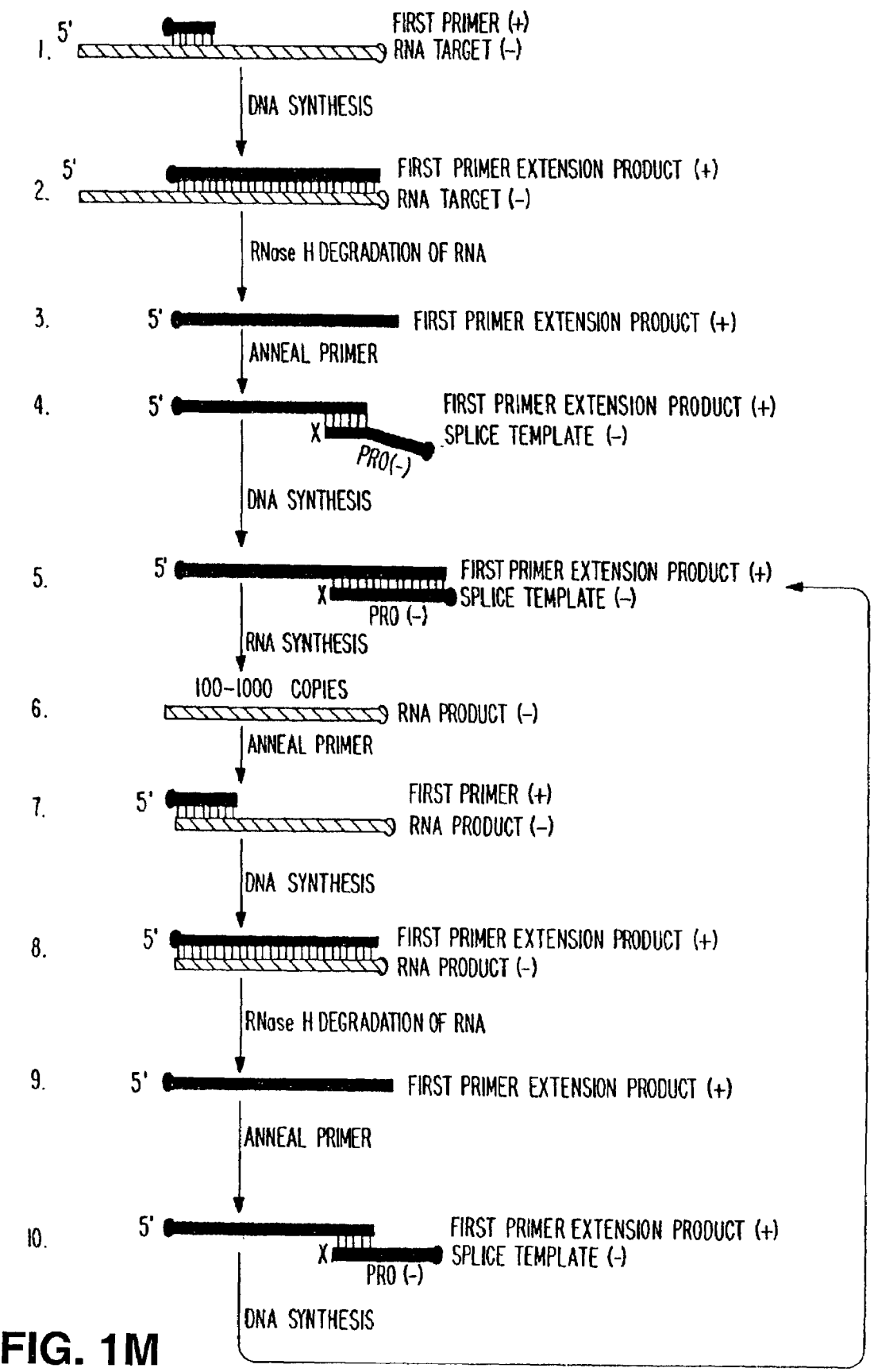

FIG. 1M depicts a target nucleic acid (RNA) which has a defined 5'-terminus, and, thus, no additional sequences 5' to the target sequence, but which has additional sequences 3' to the target sequence. The first oligonucleotide is a primer as depicted in FIG. 1I. The second oligonucleotide is a blocked splice template having a promoter, as depicted in FIGS. 1K and 1L.

Figure 1N:
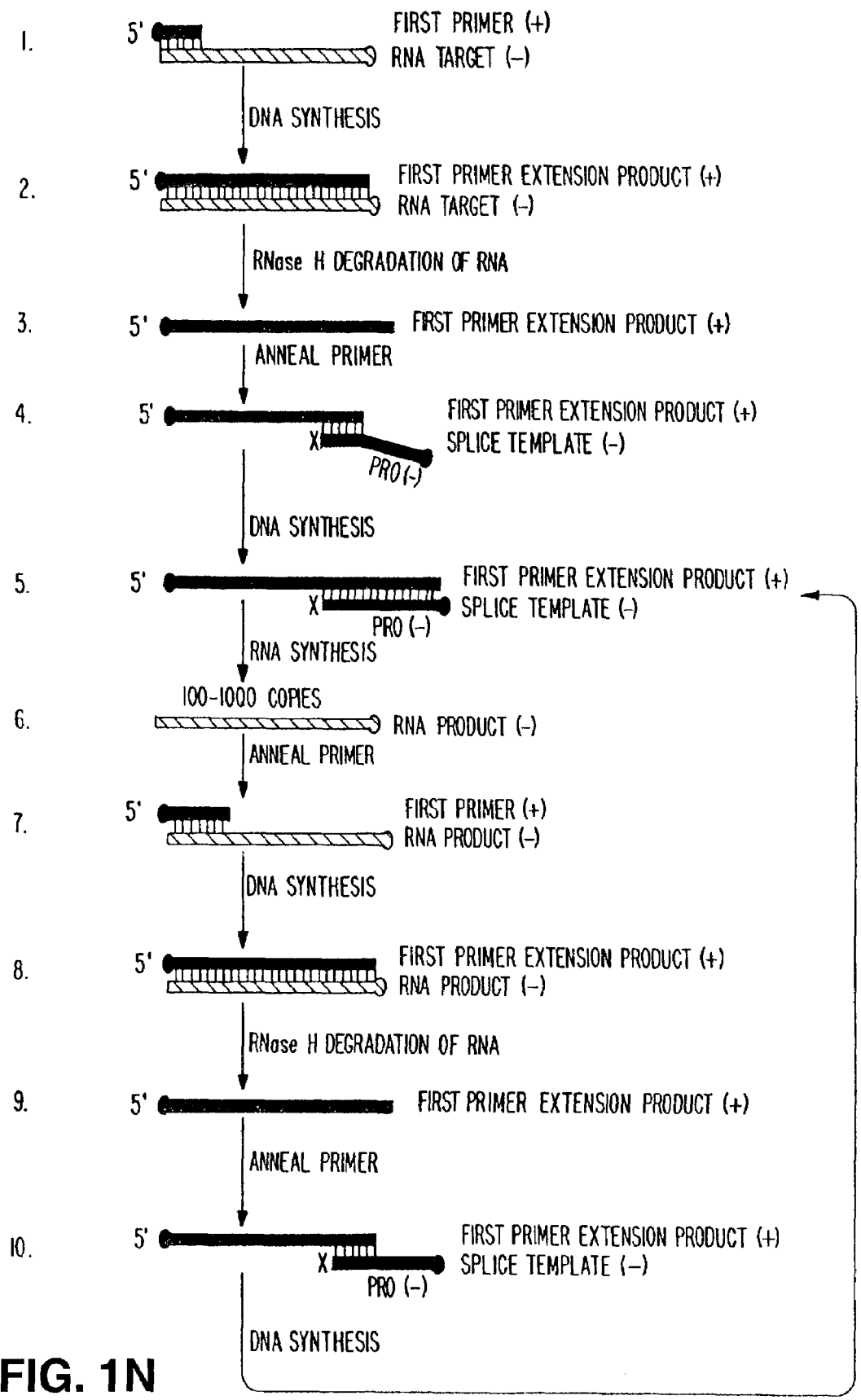
Figure 10:
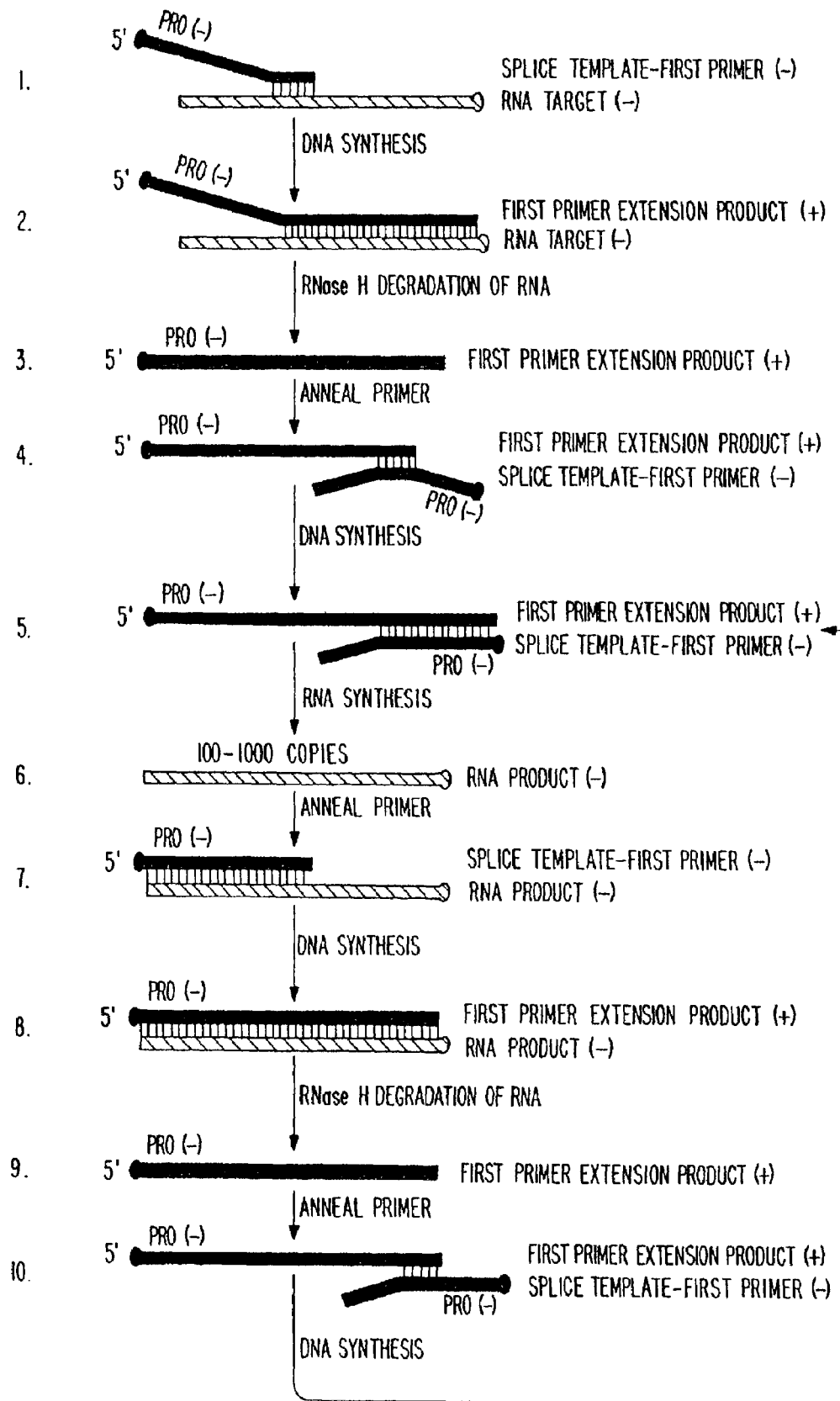

FIG. 1N depicts a target nucleic acid (RNA) which has both defined 5' and 3' sequences, having no additional sequences besides the target sequence. The first oligonucleotide comprises a primer without a promoter, as depicted in FIG. 1J. The second oligonucleotide comprises a blocked splice template having a promoter, as depicted in FIGS. 1K, 1L and 1M.

FIG. 1O depicts a target nucleic acid (RNA) which has a defined 5' terminus, having no additional sequences 5' to the target sequence, but which has additional sequences 3' to the target sequence. One oligonucleotide is used for both the first and second oligonucleotide. The oligonucleotide has a 3'-primer sequence which complexes to the 3'-terminal portion of the target sequence as shown in Step (1), and has a 5' splice template sequence with a promoter which complexes with the 3' terminus of the primer extension product as shown in step (4).

In summary, the methods of the present invention provide a method for autocatalytically synthesizing multiple copies of a target nucleic acid sequence without repetitive manipulation of reaction conditions such as temperature, ionic strength and pH which comprises (a) combining into a reaction mixture a target nucleic acid which comprises an RNA target sequence; two oligonucleotide primers, a first oligonucleotide having a complexing sequence sufficiently complementary to the 3' terminal portion of the RNA target sequence (for example the (+) strand) to complex therewith and a second oligonucleotide having a complexing sequence sufficiently complementary to the 3' terminal portion of the target sequence of its complement (for example, the (−) strand) to complex therewith, wherein the first oligonucleotide comprises a first primer which optionally has a sequence 5' to the complexing sequence which includes a promoter and the second oligonucleotide comprises a primer or a splice template; provided that if the first oligonucleotide does not have a promoter, then the second oligonucleotide is a splice template which has a sequence 5' to the priming sequence which includes a promoter for an RNA polymerase; a reverse transcriptase or RNA and DNA dependent DNA polymerases; an enzyme activity which selectively degrades the RNA strand of an RNA-DNA complex (such as an RNAse H) and an RNA polymerase which recognizes the promoter. The components of the reaction mixture may be combined stepwise or at once. The reaction mixture is incubated under conditions whereby an oligonucleotide/target sequence is formed, including DNA priming and nucleic acid synthesizing conditions (including ribonucleotide triphosphates and deoxyribonucleotide triphosphates) for a period of time sufficient whereby multiple copies of the target sequence are produced. The reaction advantageously takes place under conditions suitable for maintaining the stability of reaction components such as the component enzymes and without requiring modification or manipulation of reaction conditions during the course of the amplification reaction. Accordingly, the reaction may take place under conditions that are substantially isothermal and include substantially constant ionic strength and pH.

The present reaction does not require a denaturation step to separate the RNA-DNA complex produced by the first DNA extension reaction. Such steps require manipulation of reaction conditions such as by substantially increasing the temperature of the reaction mixture (generally from ambient temperature to about 80° C. to about 105° C.), reducing its ionic strength (generally by 10× or more) or changing pH (usually increasing pH to 10 or more). Such manipulations of the reaction conditions often deleteriously affect enzyme activities, requiring addition of additional enzyme and also necessitate further manipulations of the reaction mixture to return it to conditions suitable for further nucleic acid synthesis.

Suitable DNA polymerases include reverse transcriptases. Particularly suitable DNA polymerases include AMV reverse transcriptase and MMLV reverse transcriptase.

Promoters or promoter sequences suitable for incorporation in the primers and/or splice templates used in the methods of the present invention are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Promoter sequences for which there is a known and available polymerase that is capable of recognizing the initiation sequence are particularly suitable to be employed. Typical, known and useful promoters include those which are recognized by certain bacteriophage polymerases such as those from bacteriophage T3, T7 or SP6, or a promoter from *E. coli*.

Although some of the reverse transcriptases suitable for use in the methods of the present invention have an RNAse H activity, such as AMV reverse transcriptase, it may be preferred to add exogenous RNAse H, such as *E. coli* RNAse H. Although, as the examples show, the addition of exogenous RNAse H is not required, under certain conditions, the RNAse H activity present in AMV reverse transcriptase may be inhibited by components present in the reaction mixture. In such situations, addition of exogenous RNAse H may be desirable, where relatively large amounts of heterologous DNA are present in the reaction mixture, the native RNAse H activity of the AMV reverse transcriptase may be somewhat inhibited (see e.g., Example 8) and thus the number of copies of the target sequence produced accordingly reduced. In situations where the target sequence comprises only a small portion of DNA present (e.g., where the sample contains significant amounts of heterologous DNA), it is particularly preferred to add exogenous RNAse H. One such preferred RNAse H is *E. coli* RNAse H. Addition of such exogenous RNAse H has been shown to overcome inhibition caused by large amounts of DNA. (See, e.g., Example 8).

The RNA transcripts produced by these methods may serve as templates to produce additional copies of the target sequence through the above-described mechanisms. The system is autocatalytic and amplification by the methods of the present invention occurs autocatalytically without the need for repeatedly modifying or changing reaction conditions such as temperature, pH, ionic strength or the like. This method does not require an expensive thermal cycling apparatus, nor does it require several additions of enzymes or other reagents during the course of an amplification reaction.

The methods of the present invention may be used as a component of assays to detect and/or quantitate specific nucleic acid target sequences in clinical, environmental, forensic, and similar samples or to produce large numbers of copies of DNA and/or RNA of specific target sequence for a variety of uses.

In a typical assay, a sample to be amplified is mixed with a buffer concentrate containing the buffer, salts, magnesium, triphosphates, primers and/or splice templates, dithiothreitol, and spermidine. The reaction may optionally be incubated near 100° C. for two minutes to denature any secondary structures in the nucleic acid. After cooling, if the target is a DNA target without a defined 3' terminus, reverse transcriptase is added and the reaction mixture is incubated for 12 minutes at about 42° C. The reaction is again denatured near 100° C., this time to separate the primer extension product from the DNA template. After cooling, reverse transcriptase, RNA polymerase, and RNAse H are added and the reaction is incubated for two to four hours at 37° C. The reaction can then be assayed by denaturing the product, adding a probe solution, incubating 20 minutes at 60° C., adding a solution to selectively hydrolyze the label of the unhybridized probe, incubating the reaction six minutes at 60° C., and measuring the remaining chemiluminescent label in a luminometer. The methods of the HPA application cited supra are incorporated herein. Several other methods for product determination may be employed in place of the insolution probe hybridization.

If the target has a defined 3' terminus and one of the oligonucleotides is a splice template which has a complexing sequence sufficiently complementary to the 3' terminus to complex therewith and a promoter sequence 5' to the complex sequence or the target is RNA, a typical assay includes mixing the target with the buffer concentrate mentioned above and denaturing any secondary structure. After cooling, reverse transcriptase, RNA polymerase, and if desired, RNAse H are added and the mixture is incubated for two to four hours at 37° C. The reaction can then be assayed as described above.

II. Preliminary Procedures

The following are several embodiments of preliminary procedures which optionally may be employed in conjunction with the preferred method of the present invention. Since some target nucleic acids require modification prior to autocatalytic amplification, these procedures may be employed to accomplish the modifications. Where the target nucleic acid (and target sequence) is originally DNA, these procedures may be employed to produce RNA copies of the target sequence for use in the General Method. It should be appreciated that these Preliminary Procedures may themselves be repeated and therefore may be used as amplification methods in their own right.

Preliminary Procedure I

This method gives RNA copies of a target sequence of a target nucleic acid which comprises a (single-stranded) DNA with a defined 3' terminus. Preliminary Procedure I uses two nucleic acid components: a target nucleic acid molecule and an oligonucleotide splice template. This procedure requires a DNA target nucleic acid having a defined 3'-end. If the native 3' terminus is not known or is unsatisfactory for any reason, a new defined 3' terminus may be created by use of a restriction nuclease, ligation to another sequence, or some other means.

In the following description, (see FIGS. 2A to 2C) the target nucleic acid will arbitrarily have the "minus" sense. Thus, the splice template will have the "plus" sense so as to be sufficiently complementary to the target to complex therewith. The splice template has a complexing sequence sufficiently complementary to the 3' terminus of the target to complex therewith. The splice template also has a sequence 5' to the complexing sequence which includes a promoter sequence for an RNA polymerase. The splice template may optionally have other sequences 5' to the promoter, between the promoter and complexing sequences, and/or 3' to the complexing sequence. The splice template may also be modified at the 3' terminus to be "blocked" so that it cannot be extended by adding additional nucleotides in an extension reaction and is rendered incapable of acting as a primer in addition to acting as a splice template.

Preliminary Procedure I uses two enzyme activities: a DNA-dependent DNA polymerase and a DNA-dependent RNA polymerase.

The target nucleic acid is treated with the splice template under conditions wherein an oligonucleotide/target sequence complex is formed and DNA synthesis may be initiated. In a DNA extension reaction using an appropriate DNA polymerase, a sequence complementary to the sequence of the splice template 5' to the complexing sequence is added to the 3' terminus of the target DNA. The splice template, if not blocked at the 3' terminus, may also serve as a primer for the DNA polymerase and be extended to give a primer extension product. The product of the extension reaction, either double-stranded or partially double-stranded, target/splice template complex acts as a template for the synthesis RNA transcripts using an RNA polymerase which recognizes the promoter. The RNA transcripts may be then used for the general method or be used to generate DNA copies of the RNA as follows:

An RNA transcript comprising the target sequence (having the "plus" sense) is treated with a primer (which nominally has the "minus" sense) which has a complexing sequence sufficiently complementary to the 3' end of the target sequence of the RNA transcript to complex therewith under conditions whereby an oligonucleotide/target sequence complex is formed and DNA synthesis may be initiated. The primer is then extended in a DNA extension reaction using the RNA transcript as template to generate a DNA primer extension product having the target sequence. The DNA target sequence is separated from the RNA transcript by either denaturation or by degradation of the RNA and beginning with the splice template, the cycle is repeated. Optionally, the primer may also have additional sequences 5' to the priming sequence. The splice template may also have additional sequences 3' to the complexing sequence.

In one embodiment, the above method may be practiced using one oligonucleotide by using an oligonucleotide having a sequence which would comprise the primer 3' to the sequence which would comprise the splice template. (See, e.g. FIG. 2C).

Preliminary Procedure I is further described by reference to FIGS. 2A to 2E. FIG. 2A depicts a target nucleic acid (DNA) which has a defined 3' terminus, having no additional sequences 3' to the target sequence. The first oligonucleotide comprises both a primer and a splice template and has a promoter 5' to its complexing sequence.

Figure 2B:
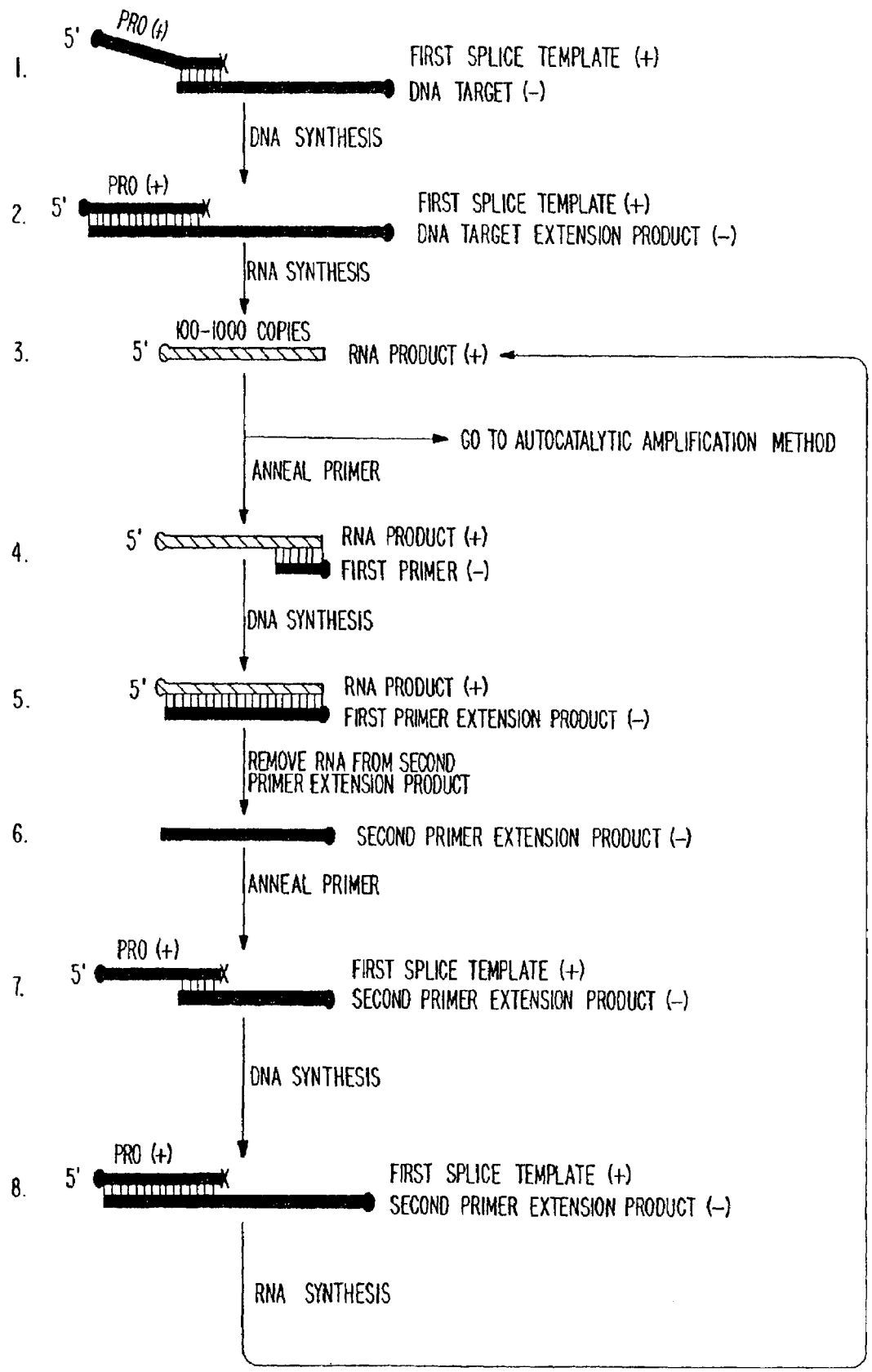
Figure 3:
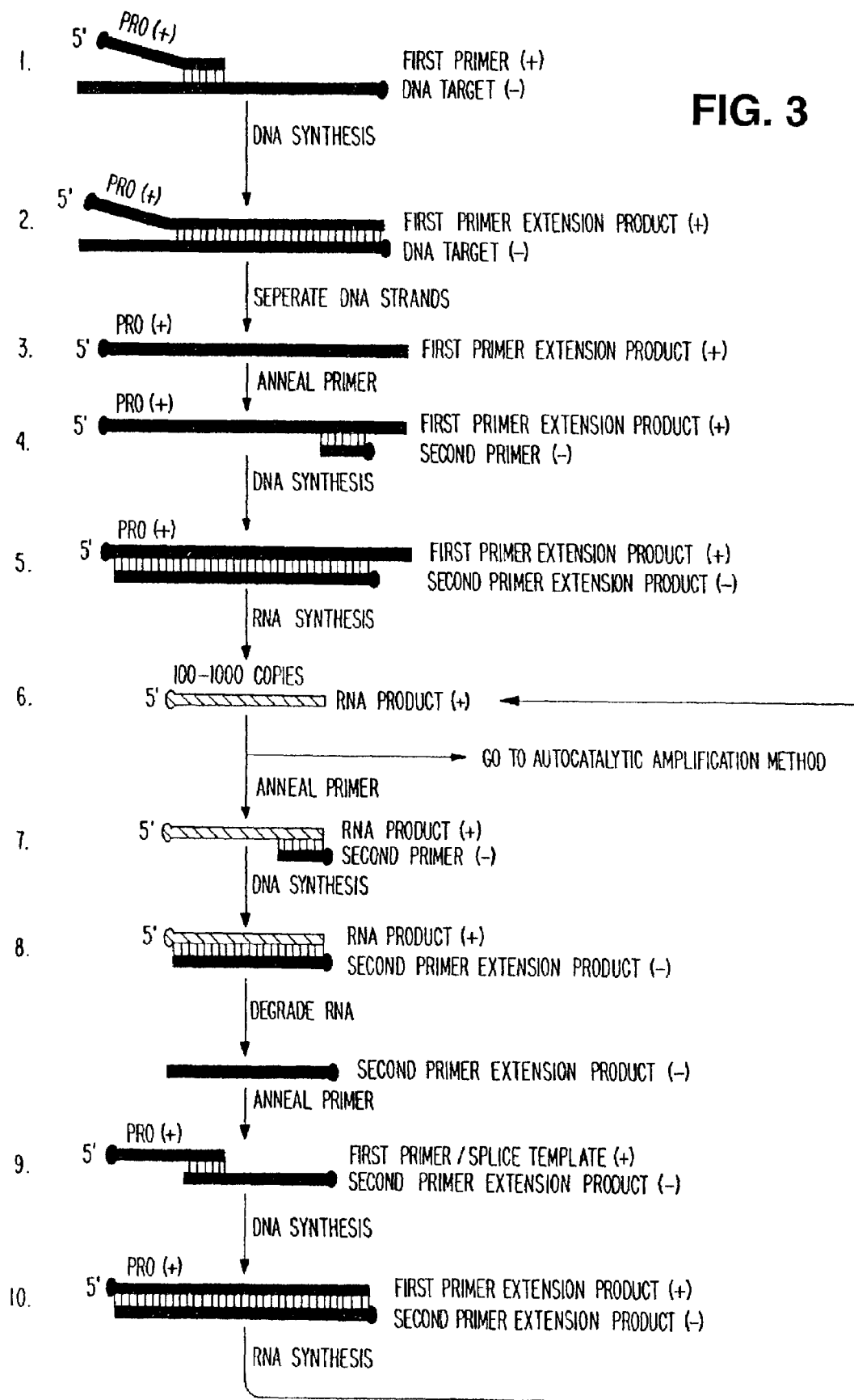
FIG. 3 depicts the embodiment of the present invention referred to as Preliminary Procedure II.
Figure 4A:
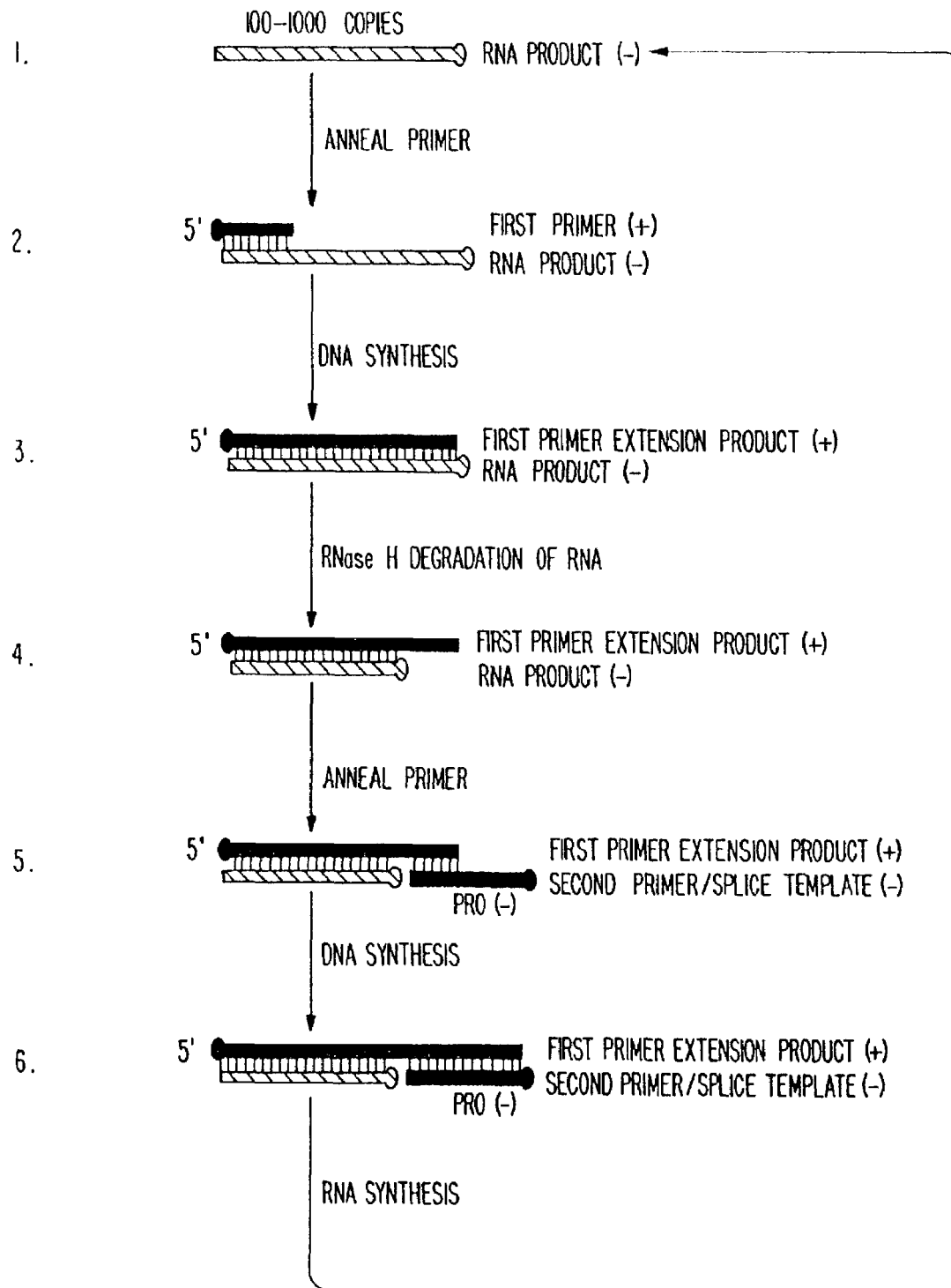
FIGS. 4A to 4D depicts the improved amplification method.
Figure 4B:
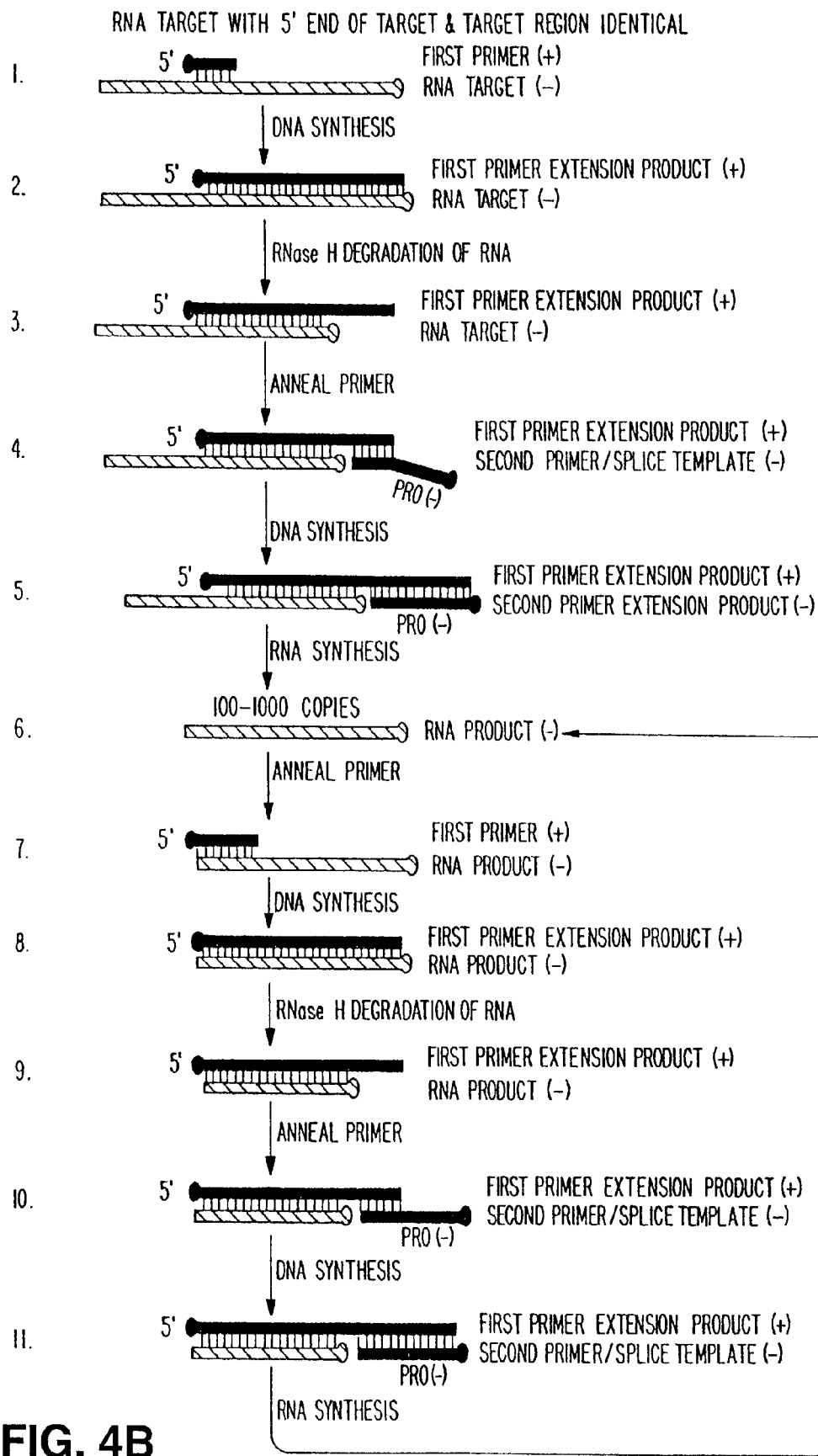
Figure 4C:
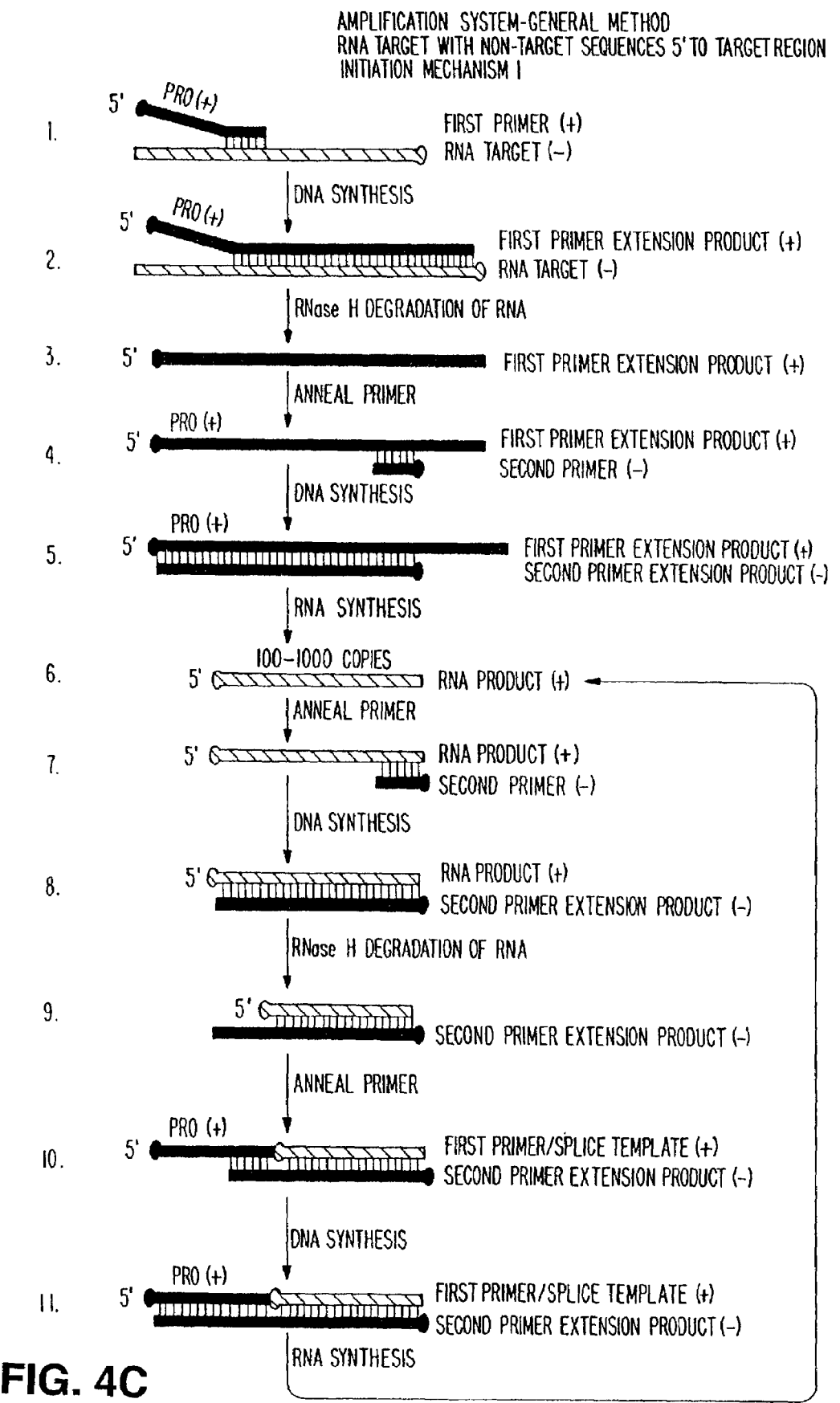
Figure 4D:
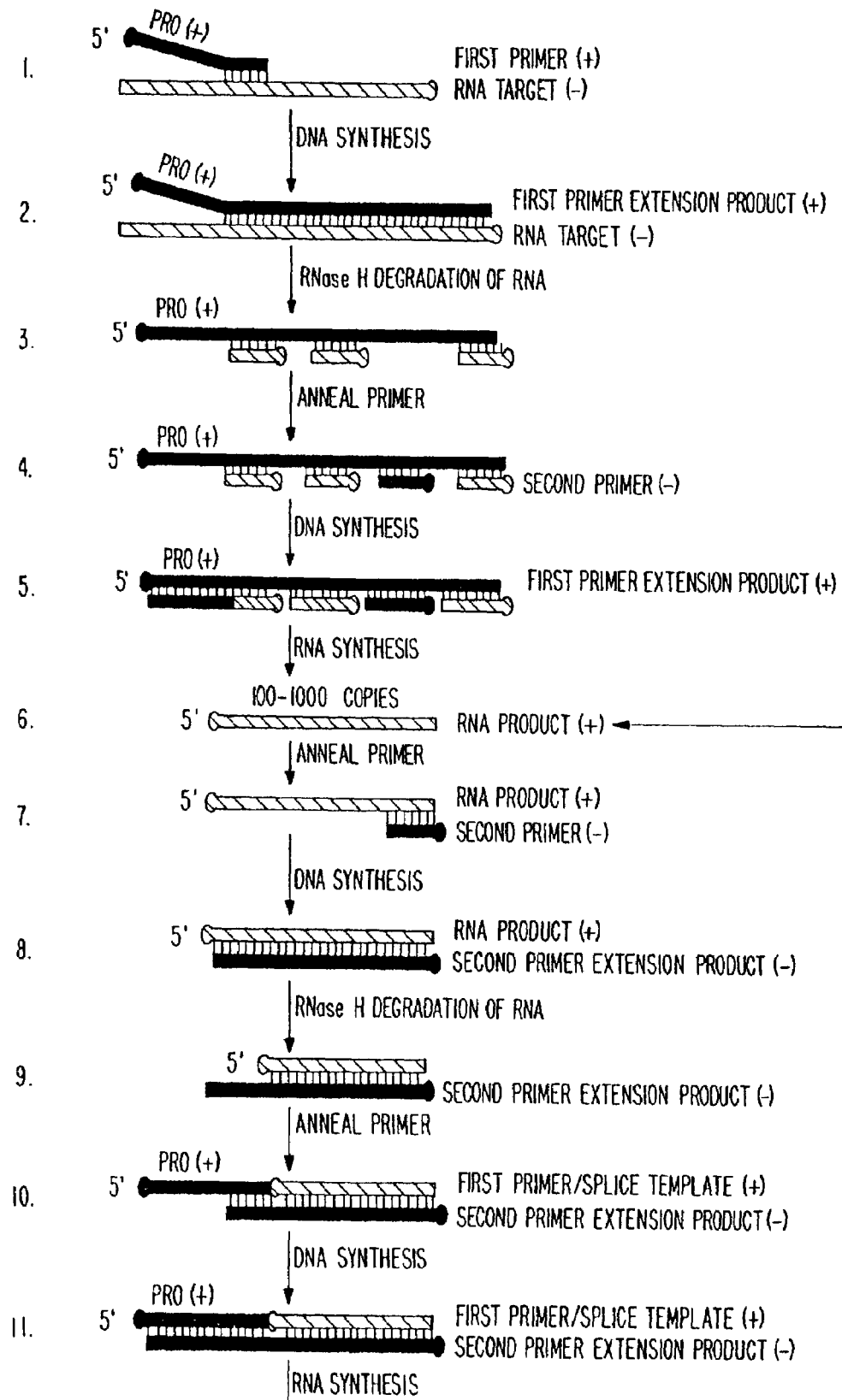

FIG. 2B depicts a target nucleic acid (DNA) as shown in FIG. 2A. The first oligonucleotide comprises a splice template which is blocked at its 3' end and is thus incapable of acting as a primer.

Figure 2C:
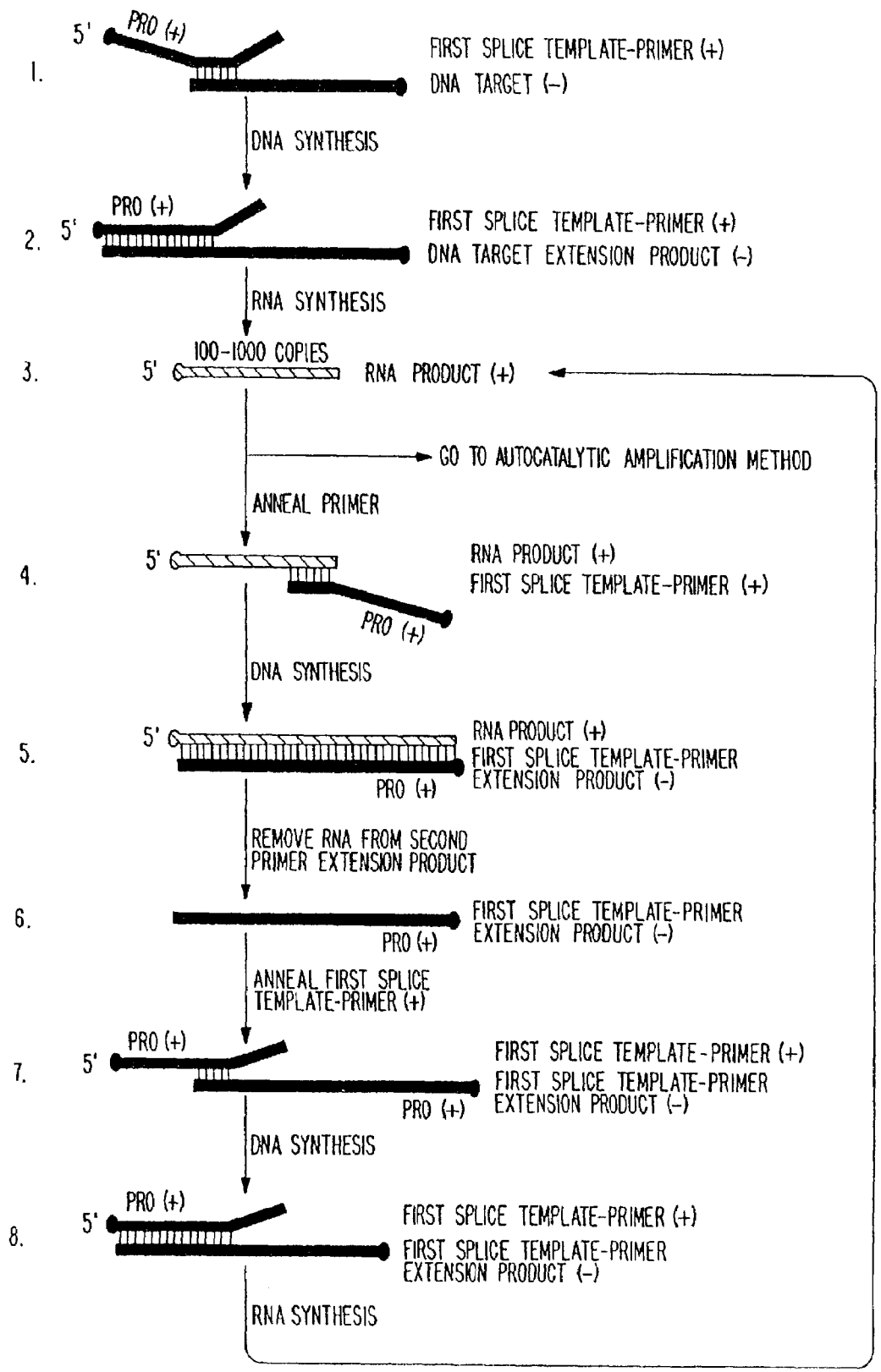

FIG. 2C depicts a target DNA as shown in FIGS. 2A and 2B. FIG. 2C depicts the use of one oligonucleotide which has a splice template (with a promoter) sequence 5' to a primer sequence at its 3' end. Thus, the oligonucleotide acts as a blocked splice template in steps (1) and (7) and as a primer (and splice template) in step (4).

Figure 2D:
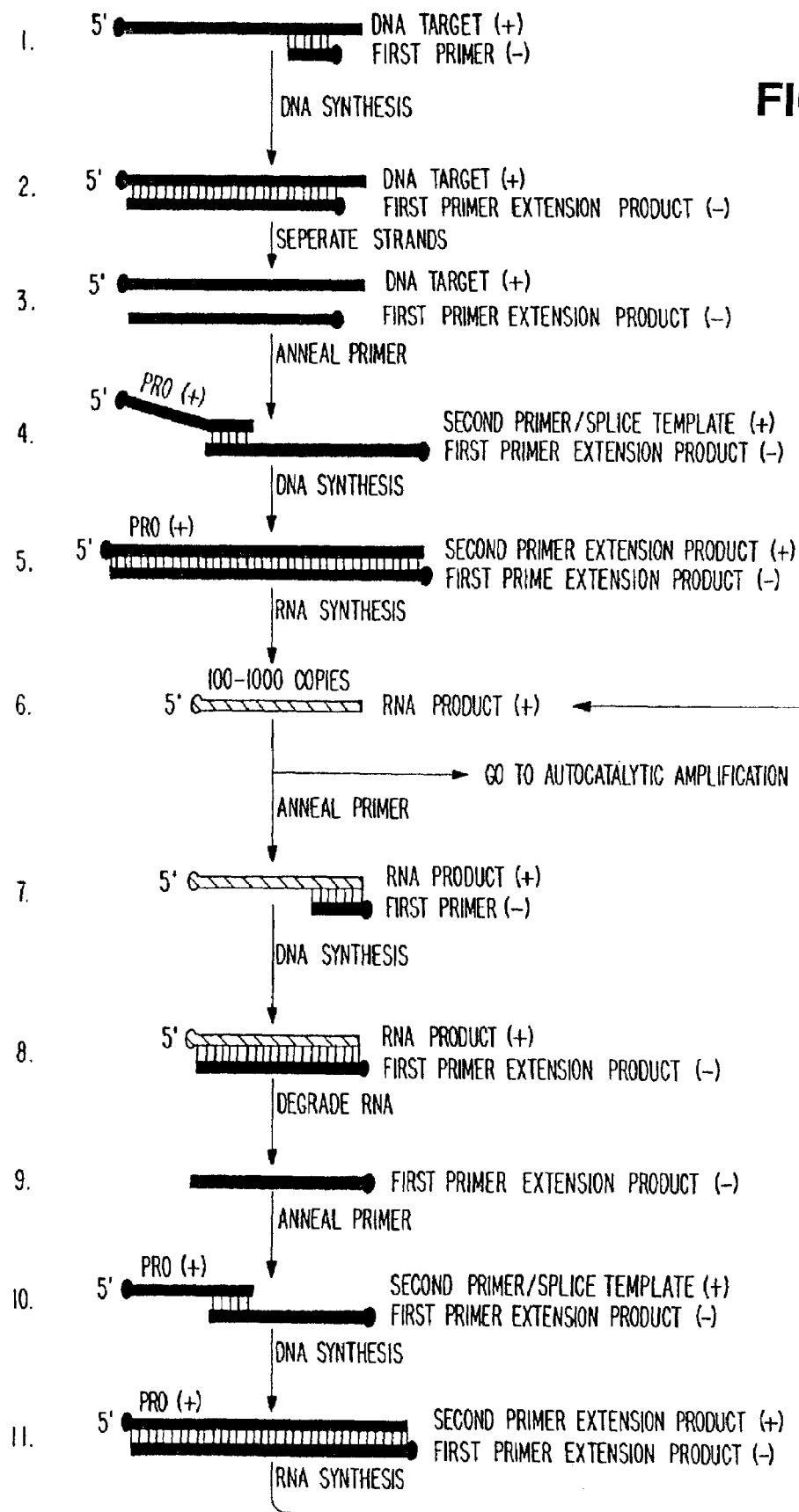

FIG. 2D depicts a target nucleic acid (DNA) which has a defined 5'-end and additional sequences 3' to the target sequence which undergoes prefatory complexing, primer extending and separating steps (steps 1 and 2) to generate a complementary DNA target having a defined 3'-terminus. The oligonucleotide of steps (1) and (7) comprises a primer which complexes with the 3' terminal portion of the target sequence of the original target DNA (here nominally (+)). The other oligonucleotide (of steps (4) and (10)) comprises an unblocked splice template which complexes with the 3'-end of the complement of the original target.

Figure 2E:
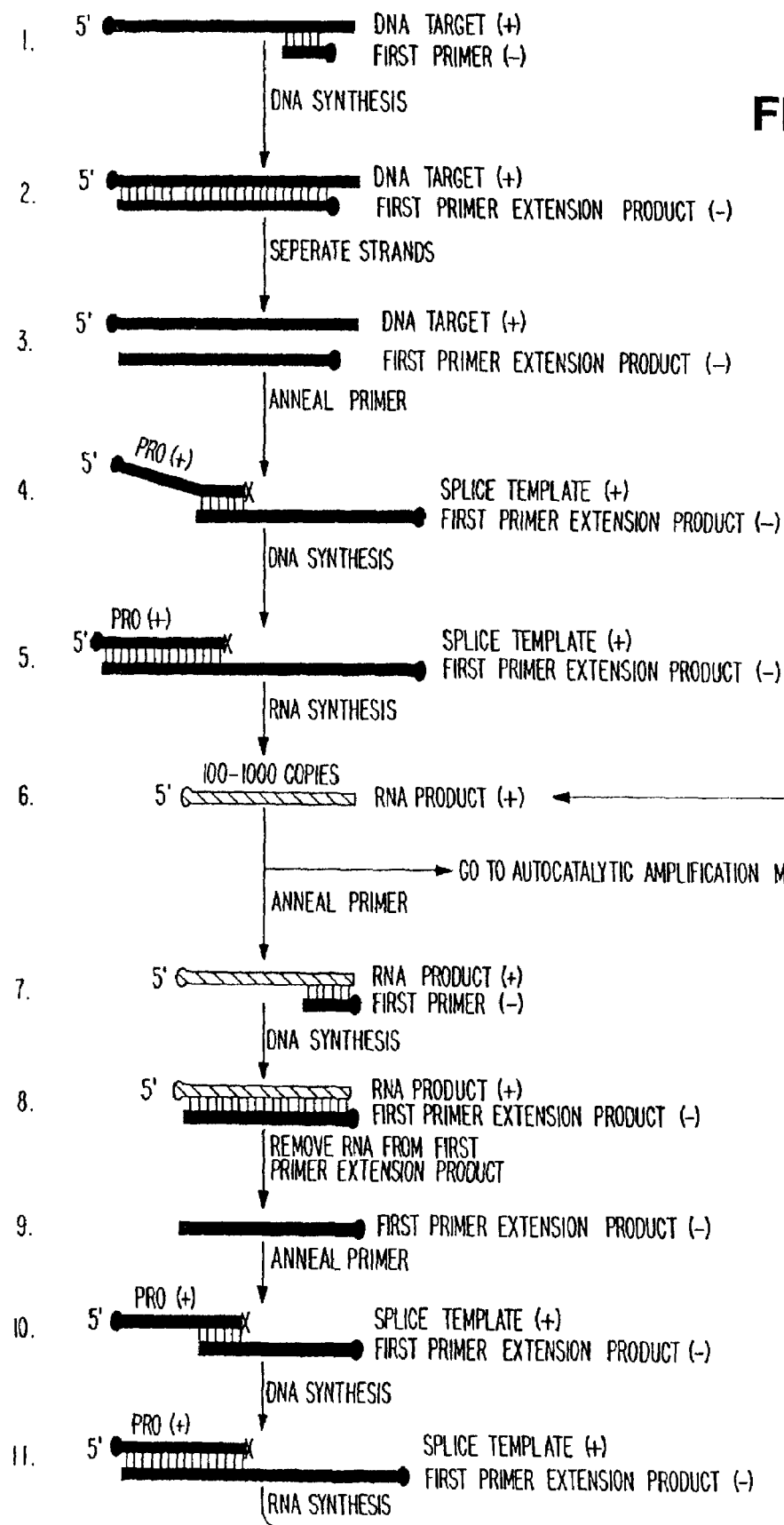

FIG. 2E depicts a target nucleic acid (DNA) which has a defined 5' terminus and additional sequences 3' to the target sequence which undergoes prefatory complexing, extending and separating steps (steps (1) and (2)) to generate a complementary DNA target having a defined 3'-terminus. The oligonucleotide of steps (1) and (7) comprises a primer which complexes with the 3' terminal portion of the target sequence of the original target DNA (here nominally (+)). The oligonucleotide of steps (4) and (10) comprises a blocked splice template which complexes with thed 3' terminal portion of the target sequence of the complement of the original target.

The splice template is complexed with the 3' terminus of the target nucleic acid under complexing conditions so that a target/splice template complex is formed and DNA synthesis may be initiated. (step 1) A suitable DNA polymerase is used to extend the 3' terminus of the target nucleic acid to add a sequence complementary to the sequence of the splice template 5' to the complexing sequence. If the 3' terminus of the splice template has not been blocked, and is sufficiently complementary to the target nucleic acid the splice template may act as a primer so that the 3' terminus of the splice template may also be extended. (FIG. 2A) The resulting target/splice template complex may be either partially or completely double-stranded. (See FIG. 2A versus FIGS. 2B and 2C) At minimum the double-stranded region comprises the promoter sequence and the priming sequence which complexed with the target nucleic acid.

The template of Step 2 is transcribed by an appropriate RNA polymerase. The RNA polymerase produces about 5–1000 copies of RNA for each template. In FIGS. 2A to 2C, the RNA produced is nominally of the "plus" sense and includes the sequence from the 3' end of the promoter to the 5' end of the target nucleic acid.

The RNA product of Step 3 may be used according to the general method to autocatalytically amplify the target sequence or alternatively may be treated under complexing and priming conditions with a primer which has a complexing sequence at its 3' terminus sufficiently complementary to the 3' terminal portion of the target sequence in the RNA to complex therewith and optionally includes other sequences 5' to the complexing sequence. The primer is extended using the RNA as a template by an RNA-dependent DNA polymerase in a primer extension reaction. This produces a product which is at least partially double-stranded and which must be made at least partially single-stranded for further synthesis by degradation of the RNA portion, such as by an RNAse H (step 5) or by some other method such as denaturation.

The DNA produced in Step 6 may be used as a target molecule for Step 1 and treated with a splice template as described above to produce more RNA and DNA. These steps may be cycled to produce any desired level of amplification. It should also be noted that, by appropriate choice of the splice template and primer(s), this new target molecule (Step 6) may have different termini than the original molecule. Furthermore, if the primer extension product from the RNA has a promoter sequence 5' to the complexing sequence, a second primer having a complexing sequence of the "plus" sense and optionally other sequences 5' to the complexing sequence may be used to copy the extended primer product to produce a double-stranded template for an RNA polymerase. A template so produced enables the RNA polymerase to make "minus" sense RNA which may be amplified using the general method or further amplified using the procedures herein.

Preliminary Procedure II

Preliminary Procedure II differs from Preliminary Procedure I in the way the autocatalytic species is generated. The DNA target nucleic acid need not have a defined 3' terminus. In one aspect, a primer containing a promoter sequence 5' to the complexing sequence is used instead of a splice template to introduce the promoter sequence into the template for the RNA polymerase. The primer has a complexing sequence sufficiently complementary to the 3'-terminal portion of the target sequence to complex therewith and a sequence which includes a promoter for an RNA polymerase 5' to the complexing sequence. The primer is extended with a DNA polymerase to give a primer extension product.

After separation of the strands, usually by thermal denaturation, a second oligonucleotide of the same sense as the target molecule is used as a primer to synthesize a DNA complement to the first primer extension product. The second primer may have additional sequences 5' to the complexing region which may include a promoter. Inclusion of a promoter sequence in the second primer may enhance amplification. The second primer may also be a splice template.

Preliminary Procedure II is further described with reference to FIG. 3. FIG. 3 depicts a target DNA which has additional sequences both 5' and 3' to the target sequence. The first primer has a complexing sequence at its 3' terminus and a sequence 5' to the complexing sequence which includes a promoter sequence and complexes sufficiently with the target to serve a priming function and initiate DNA synthesis. An appropriate DNA polymerase extends the primer to give a primer extension product. The strands are separated by denaturation or other means to yield to a single-stranded promoter containing primer extension product.

A second primer is used which has a complexing sequence at its 3' terminus sufficiently complementary to the 3' terminal portion of the target sequence of the first primer extension product and, optionally, other sequences 5' to the complexing sequence which may include a promoter sequence. The second primer is complexed sufficiently with the primer extension product from Step 3 to serve a priming function and initiate DNA synthesis. The DNA polymerase extends the second primer to give a second primer extension product. The resulting double-stranded DNA molecule may now serve as a template for the RNA polymerase to generate RNA transcripts for the General Method. As depicted in FIG. 3, the RNA molecules produced are nominally of the "plus" sense and may be multiplied using the general method of the present invention.

Where the complexing sequence of the second primer is complementary to the 3' terminus of the first primer extension product from Step 3 and the second primer includes a promoter sequence 5' to the complexing sequence, the second primer may serve as a splice template so that the 3'-terminus of the first primer extension product from Step 3 may be further extended to add the promoter sequence and produce a template for the RNA polymerase which produces RNA transcripts of both senses. The RNA molecules so produced may be amplified using the general method.

In another aspect of the present invention, the second primer acts as a splice template and has a promoter 5' to the complexing sequence, so that the first primer need not have a promoter. In that case, the first primer extension product from Step 2 is further extended to produce a complement to the promoter sequence, thus generating a template for the production of "minus" sense RNA by the RNA polymerase.

By repeating the steps described above, additional RNA and DNA copies of the target sequence may be produced.

EXAMPLES

Preface

The following examples of the procedures previously described demonstrate the mechanism and utility of the methods of the present invention. They are not limiting to the inventions and should not be considered as such.

Many of the materials used in one or more examples are similar. To simplify the descriptions in the examples, some of the materials will be abbreviated and described here.

The template referred to as "frag 1" is a double-stranded segment of DNA homologous to a region of DNA from the hepatitis B genome. It has been excised from a plasmid via restriction nuclease digestion and purified from the remaining nucleic acid by chromatographic methods. Subsequent to purification, the fragment has been cut with a restriction endonuclease and purified via phenol extraction and ethanol precipitation to yield the desired target.

The template referred to as "M13L(−)" is a purified single-stranded DNA target containing, as a small fraction of the total sequence, the minus strand target sequence.

Several different primers and splice templates were used in the examples described herein. The oligonucleotides referred to as T7pro(+) contains, near the 5' terminus, a T7 RNA polymerase promoter and, near the 3' terminus, a sequence complementary to the 3' terminus of the minus-strand target sequence to the two templates described above; T7pro(+) also contains other sequence information to enhance performance. The sequence for T7pro(+) is 5'-AATTT AATAC GACTC ACTAT AGGGA GAGGT TATCG CTGGA TGTGT CTGCG GCGT3' (SEQ ID NO:26).

Another oligonucleotide similar to T7pro(+) is ddT7pro (+). It differs from T7pro(+) in that the 3' terminus has been extended with a dideoxy nucleotide using terminal deoxynucleotidyl transferase. Unlike T7pro(+), ddT7pro(+) is incapable of serving as a primer for DNA synthesis by reverse transcriptase but can act as a splice template.

HBV(−)Pr is a primer which will hybridize to the plus strand of the frag 1 template and is homologous to a sequence within the M13L(−). [HBV(−)Pr is complementary to a sequence 3' to the plus strand sequence homologous to the T7pro(+).] The sequence for HBV(−)Pr is 5'-GAGGA CAAAC GGGCA ACATA CCTTG-3' (SEQ ID NO:27).

Another oligonucleotide containing a promoter region is T7pro(−). This promoter-primer contains a sequence identical to T7pro(+) but replaces the sequence complementary to the minus target with a sequence complementary to the plus target. The 3' terminus of T7pro(−) is complementary to the 3' terminus of the plus strand of frag 1. The sequence for T7pro(−) is 5'-AATTT AATAC GACTC ACTAT AGGGA GATCC TGGAA TTAGA GGACA AACGG GC-3' (SEQ ID NO:28). Like the ddT7pro(+), ddT7pro(−) is a 3' blocked oligonucleotide made by extending the 3' terminus with a dideoxynucleotide using terminal deoxynucleotidyl transferase. The ddT7pro(−) cannot serve as a primer but is otherwise similar to T7pro(−).

The templates used in these examples contain substantial sequence between the regions homologous or complementary to the and splice templates described above. As the sequence between the oligonucleotides will be amplified as a result of the invention, quantification of this sequence provides a specific means of measuring the amplification. It has been convenient to assay the products by hybridization techniques using DNA probes specific for the sequences coded for between the oligonucleotide primers and splice templates. Two probes are used in the examples presented below: Probe(+) and Probe(−). Probe(+) is complementary to the minus sense product and Probe(−) is complementary to the plus sense product. The sequence for Probe(+) is 5'-CCTCT TCATC CTGCT GCTAT GCCTC-3' (SEQ ID NO:29) and the sequence for Probe(−) is 5'-GAGC ATAGC AGCAG GATGA AGAGG-3' (SEQ ID NO:30). The probes used herein have been labeled with a chemiluminescent tag. In the assay, the label on hybridized probe emits light which is measured in a luminometer.

In the following examples, relative amplification was measured as follows. A sample of the amplification reaction mixture (usually 10 µl) was diluted to 50 µl with 10 mM Tris-HCl, pH 8.3, and denatured two minutes at 95° C. After cooling on ice, 50 µl of a probe solution containing approximately 75 fmol Probe(+) or Probe(−), 0.2 M lithium succinate, pH 5.2, 21% (w/v) lithium lauryl sulfate, 2 mM EDTA, and 2 mM EGTA, was added to the sample and mixed. The reactions were then incubated 20 minutes at 60° C. and cooled. To each hybridization reaction was added 500 µl of a solution prepared by adjusting a saturated sodium borate solution to pH 8.5 with hydrochloric acid, then diluting to bring the borate concentration to 0.8 M final and adding Triton X-100 to 5% (v/v) final. The reactions were then mixed and incubated six minutes at 60° C. to destroy the chemiluminescent label of the unhybridized probe. This method of destruction of the chemiluminescent label of unhybridized probe is quite specific; only a very small fraction of the unhybridized probe remains chemiluminescent. The reactions were cooled and the remaining chemiluminescence was quantified in a luminometer upon the addition of 200 µl of 1.5 M sodium hydroxide, 0.1% (v/v) hydrogen peroxide. In the assay, hybridized probe emits light which is measured in a luminometer. Since the reaction which destroys the chemiluminescent label of unhybridized probe is not 100% effective, there is generally a background level of signal present in the range of about 300 to 1300 relative light units (RLU).

Many other assay methods are also applicable, including assays employing hybridization to isotopically labeled probes, blotting techniques and electrophoresis.

The enzymes used in the following examples are avian myeloblastosis virus reverse transcriptase from Seikagaku America, Inc., T7 RNA polymerase from New England Biolabs or Epicentre, and Moloney murine leukemia virus (MMLV) reverse transcriptase and E. coli RNAse H from Bethesda Research Laboratories. Other enzymes containing similar activities and enzymes from other sources may be used; and other RNA polymerases with different promoter specificities may also be suitable for use.

Unless otherwise specified the reaction conditions used in the following examples were 40 mM Tris-HCl, 25 mM NaCl, 8 mM MgCl$_2$, 5 mM dithiothreitol, 2 mM spermidine trihydrochloride, 1 mM rATP, 1 mM rCTP, 1 mM rGTP, 1 mM rUTP, 0.2 mM dATP, 0.2 mM dCTP, 0.2 mM dGTP, 0.2 mM dTTP, 0.15 µM each primer or splice template, and specified amounts of template and enzymes in 100 µl volumes.

These reaction conditions are not necessarily optimized, and have been changed as noted for some systems. The oligonucleotide sequences used are exemplary and are not meant to be limiting as other sequences have been employed for these and other target sequences.

Example 1

Preliminary Procedure I

To demonstrate that this system worked, each of the four promoter containing oligonucleotides described above were each respectively put into reactions with or without 4 fmol target (frag 1). The reaction was incubated 2 minutes at 95° C. to denature the target, then cooled to allow the oligonucleotides to anneal to the target. Reverse transcriptase, 13 Units, and T7 RNA polymerase, 100 Units, were added and the reaction was incubated 30 minutes at 37° C. One-tenth of the reaction was assayed using the hybridization method. The results (in Relative Light Units or "RLU(s)" and fmols) presented in Table 1 show that both the blocked and unblocked oligonucleotides serve as splice templates to produce product. The signals measured for reactions without target represent typical background levels of signal, for this type of assay.

TABLE 1

Comparison of Splice Templates in Preliminary Procedure I.

| Spice Template | Target | Probe(−) | Product RLU | fmol |
|---|---|---|---|---|
| ddT7pro(+) | 4 fmol | Probe(−) | 38451 | 240 |
| ddT7pro(+) | 0 fmol | Probe(−) | 544 | 0 |
| T7pro(+) | 4 fmol | Probe(−) | 65111 | 410 |
| T7pro(+) | 0 fmol | Probe(−) | 517 | 0 |
| ddT7pro(−) | 4 fmol | Probe(+) | 47756 | 85 |
| ddT7pro(−) | 0 fmol | Probe(+) | 879 | 0 |
| T7pro(−) | 4 fmol | Probe(+) | 156794 | 290 |
| T7pro(−) | 0 fmol | Probe(+) | 600 | 0 |

Example 2

Cycling With Preliminary Procedure I

The amplification system was cycled with ddT7pro(+) and T7pro(+). In this experiment, 4 amol frag I, HBV(−)Pr and ddT7pro(+) or T7pro(+) were mixed in standard reactions and incubated at 95° C. After cooling, 13 Units of reverse transcriptase and 100 units of T7 RNA polymerase were added and the mixture was incubated 30 minutes at 37° C. One-tenth of the reaction was removed for assay and the cycle was repeated with the remainder. After repeating the cycle a third time, the 10 µl aliquots were assayed by the hybridization method using Probe(−). The results presented in Table 2 indicate that product is amplified through cycling with both blocked and unblocked splice templates.

TABLE 2

Cycling with Preliminary Procedure I.

| Splice template | Target | Relative Light Units (RLU's) | | |
|---|---|---|---|---|
| | | Cycle 1 | Cycle 2 | Cycle 3 |
| ddT7pro(+) | 4 amol | 602 | 1986 | 10150 |
| ddT7pro(+) | 0 amol | 658 | 592 | 595 |
| T7pro(+) | 4 amol | 891 | 6180 | 52160 |
| T7pro(+) | 0 amol | 496 | 504 | 776 |

Example 3

Sensitivity of Preliminary Procedure I

In this example the unblocked splice template, T7pro(+), and the primer, HBV(−)Pr, were used to test the sensitivity of the amplification method. Six cycles of Preliminary Procedure I were run as described in Example 2 with decreasing quantities of frag 1. After amplification, the product was assayed using the hybridization method described in the Detailed Description of the Invention. Using this method, $4 \times 10^{-21}$ moles frag 1 could be detected (see Table 3).

TABLE 3

Sensitivity using 6 cycles of Preliminary Procedure I.

| Target (moles) | Sample μl | Product RLU's |
|---|---|---|
| $4 \times 10^{-18}$ | 5 | 328390 |
| $4 \times 10^{-19}$ | 20 | 105364 |
| $4 \times 10^{-20}$ | 20 | 3166 |
| $4 \times 10^{-21}$ | 20 | 1927 |
| 0 | 20 | 806 |

Example 4

Amplification Including Preliminary Procedure I

In the following example, the target to be amplified was frag 1. In the first set of reactions, various combinations of target and splice templates were incubated at 95° C. for two minutes then cooled prior to adding 13 Units of reverse transcriptase and 100 Units of T7 RNA polymerase. The reactions were incubated 30 minutes at 37° C. then 5 μl aliquots of the reactions were assayed with both probes to quantitate the products. Subsequent to this assay, reactions were prepared using 5 μl of reactions 1 and 2 and the T7pro(−) splice template. The mixtures were incubated 2 minutes at 95° C. then cooled prior to adding 13 Units of reverse and 100 Units of T7 RNA polymerase. The new reactions were then mixed and incubated at 37° C. for 2 hours. Aliquots of 10 μl were removed to an ice bath at time points indicated in Table 4 below. The products were assayed using the hybridization method previously described. The data indicate that both splice templates allow production of RNA from frag 1. The data also indicate significantly more minus and plus sense products are produced in the reactions containing RNA and the splice template complementary to that RNA. And, finally, the reaction kinetics for the reaction 1B show a geometric increase in product whereas the kinetics for the 2B reaction are of a more linear form. This difference indicates the product in the 1B reaction is serving as a substrate to generate more product; thus the reaction is autocatalytic.

TABLE 4

Preliminary Procedure I

| | Reaction | | | |
|---|---|---|---|---|
| | 1 | 2 | 3 | 4 |
| Target (4 fmol) | Yes | Yes | Yes | No |
| T7pro(+) | Yes | No | No | No |
| T7pro(−) | No | No | Yes | No |

TABLE 4-continued

Preliminary Procedure I

| Probe | Time | Relative Light Units (RLU's) | | | |
|---|---|---|---|---|---|
| Probe(+) | 30' | 1156 | 1058 | 21859 | 591 |
| Probe(−) | 30' | 11693 | 771 | 744 | 691 |

| | Reaction | | | |
|---|---|---|---|---|
| | 1A | 1B | 2A | 2B |
| Reaction1 | Yes | Yes | No | No |
| Reaction2 | No | No | Yes | Yes |
| T7pro(−) | No | Yes | No | Yes |

| Probe | Time | Relative Light Units | | | |
|---|---|---|---|---|---|
| Probe(+) | 0' | 714 | 757 | 639 | 661 |
|  | 30' | 686 | 339 | 1663 | 1373 |
|  | 60' | 718 | 6331 | 645 | 1786 |
|  | 120' | 816 | 16889 | 660 | 2238 |
| Probe(−) | 120' | 3142 | 6886 | 637 | 780 |

Example 5

Reaction Kinetics for Amplification Including Preliminary Procedure I

The following example further demonstrates the potential of this embodiment of the methods the invention. A small quantity of frag 1 (10 amol), was used in reactions with various combinations of T7pro(+), T7pro(−), and HBV(−)Pr. The reaction mixtures were incubated at 95° C. for two minutes to denature the DNA target and cooled prior to adding reverse transcriptase and T7 RNA polymerase. After mixing, the reactions were incubated 30 minutes at 37° C. Fifteen microliter aliquots were removed at various time points and stored at 0° C. until assayed. The hybridization assay was used to quantitate the products of the reactions. The data presented in Table 5 show that the invention requires one splice template and one primer. A second splice template is advantageous, however. The results with only one primer or splice template were below the detection limits of the assay. As in the previous example, the reaction kinetics are geometric, indicating an autocatalytic system.

TABLE 5

Preliminary Procedure II Reaction Kinetics.

| | Reaction | | | | | | |
|---|---|---|---|---|---|---|---|
| | 1 | 2 | 3 | 4 | 5 | 6 | 7 |
| Target (10 amol) | No | Yes | Yes | Yes | Yes | Yes | Yes |
| T7pro(+) | Yes | No | Yes | No | No | Yes | Yes |
| T7pro(−) | Yes | No | No | Yes | No | No | Yes |
| HBV(−) Pr | Yes | No | No | No | Yes | Yes | No |
| Time (minutes) | Minus Product (RLU's) | | | | | | |
| 0 | 619 | 638 | 635 | 703 | 592 | 619 | 656 |
| 30 | 613 | 635 | 613 | 755 | 626 | 844 | 1133 |
| 60 | 635 | 649 | 856 | 894 | 635 | 2146 | 6008 |
| 90 | 593 | 619 | 619 | 925 | 624 | 6226 | 23484 |
| 120 | 621 | 606 | 627 | 946 | 639 | 12573 | 43939 |
| 180 | 678 | 635 | 714 | 930 | 627 | 21719 | 78682 |

TABLE 5-continued

Preliminary Procedure II Reaction Kinetics.

| Time (minutes) | Plus Product (RLU's) | | | | | | |
|---|---|---|---|---|---|---|---|
| 0 | 624 | 646 | 1661 | 710 | 621 | 636 | 962 |
| 30 | 637 | 601 | 802 | 629 | 655 | 803 | 758 |
| 60 | 639 | 706 | 800 | 679 | 664 | 226 | 2895 |
| 90 | 638 | 683 | 956 | 633 | 687 | 7786 | 8085 |
| 120 | 643 | 670 | 884 | 647 | 632 | 18160 | 18241 |
| 180 | 683 | 617 | 968 | 758 | 712 | 34412 | 41165 |

Our subsequent work has demonstrated continued product synthesis for over 5.0 hours, which is substantially better than prior art methods. We also have demonstrated increased sensitivity.

Example 6

Amplification Including Preliminary Procedure II

In this example various combinations of primers were used to amplify 500 amol of a DNA target without defined termini. The target was the M13L(−) referenced above. Upon reaction preparation, the samples were incubated two minutes at 95° C., then cooled prior to adding 13 Units of reverse transcriptase. The reactions were then incubated twelve minutes at 42° C. Next the reactions were again heated for two minutes at 95° C. and cooled. Reverse transcriptase and T7 RNA polymerase were added and the reactions were incubated for two hours at 37° C. Ten microliter aliquots of the reaction were assayed with both Probe(+) and Probe(−). The results presented in Table 6 show that synthesis of large amounts of nucleic acid occurs only when two primers are employed. They also demonstrate the benefit of two promoter-primers over one promoter-primer and one primer. The low level synthesis in reactions 4 and 5 correspond to synthesis of approximately one copy of DNA from the original template. The system employs an initial 95° C. denaturation step which may serve to denature double-stranded targets or double-stranded regions of a single-stranded target as well as inactivate unwanted nuclease and protease activities.

TABLE 6

Preliminary Procedure II System.

| | Reaction | | | | | | |
|---|---|---|---|---|---|---|---|
| | 1 | 2 | 3 | 4 | 5 | 6 | 7 |
| M13L(−) | No | No | Yes | Yes | Yes | Yes | Yes |
| T7pro(+) | Yes | Yes | No | Yes | No | Yes | Yes |
| T7pro(−) | Yes | No | No | No | Yes | Yes | No |
| HBV(−) Pr | No | Yes | No | No | No | No | Yes |
| Probe | Relative Light Units (RLU's) | | | | | | |
| Probe(+) | 862 | 744 | 762 | 1089 | 2577 | 96221 | 30501 |
| Probe(−) | 473 | 420 | 483 | 3038 | 1080 | 15171 | 14863 |

Example 7

Effect of RNAse H

To demonstrate that the addition of exogenous RNAse H may improve amplification in the autocatalytic systems described of the present invention, several reactions were prepared using various quantities of target, M13L(−), and either 0 or 2 Units of exogenous RNAse H. The exogenous RNAse H used was derived from *E. coli*. All reactions were prepared with T7pro(+) and T7pro(−). The reactions were subjected to the 95° C. denaturation and cooled prior to adding reverse transcriptase. After a twelve minute incubation at 42° C., the reactions were again denatured at 95° C. After cooling, reverse transcriptase, T7 RNA polymerase, and, if indicated (see Table 7), RNAse H was added and the reactions were incubated for 3 hours at 37° C. Aliquots of 10 μl were removed from each reaction at hourly intervals for assay by the hybridization method. The data in Table 7 show that exogenous RNAse H significantly enhanced the reaction kinetics and increases the sensitivity of the invention. Signals less than 600 RLUs were interpreted as typical background levels.

TABLE 7

Effect of Exogenous RNAse H on Amplification Including Preliminary Procedure II Sensitivity.

| Target | RNAse H | RLU's at Time(hours) | | | |
|---|---|---|---|---|---|
| (moles) | (Units) | 0 | 1 | 2 | 3 |
| $1 \times 10^{-17}$ | 0 | 478 | 7659 | 28716 | 60443 |
| $1 \times 10^{-18}$ | 0 | 440 | 946 | 13332 | 36039 |
| $1 \times 10^{-19}$ | 0 | 413 | 581 | 10063 | 41415 |
| $1 \times 10^{-20}$ | 0 | 406 | 424 | 717 | 4520 |
| 0 | 0 | 455 | 376 | 579 | 2075 |
| $1 \times 10^{-18}$ | 2 | 419 | 20711 | 50389 | 64073 |
| $1 \times 10^{-19}$ | 2 | 411 | 6831 | 21312 | 29818 |
| $1 \times 10^{-20}$ | 2 | 420 | 604 | 1281 | 1375 |

Example 8

Effect of Exogenous DNA

It has been demonstrated that the addition of exogenous DNA may significantly inhibit this autocatalytic amplification system. To further demonstrate the benefit of adding exogenous RNAse H, amplification reactions were prepared with or without 2 μg calf thymus DNA to demonstrate this inhibition. In reactions with the calf thymus DNA, two concentrations of reverse transcriptase were employed to test whether additional AMV RNAse H would overcome the inhibition. Also, RNAse H from *E. coli* was added to some of the reactions for the same reasons. The reactions differ from the standard reactions in that the concentration for each of the ribonucleotides were increased to 2.5 mM and the concentration of magnesium chloride was increased to 12.8 mM. The reactions were prepared using 100 amol of M13L (−) as a target and T7pro(+) and T7pro(−). After denaturing two minutes at 95° C., the reactions were cooled and 13 or 39 Units of reverse transcriptase were added and the reactions were incubated 12 minutes at 37° C. The reactions were again denatured at 95° C. and cooled prior to adding 13 or 39 Units of reverse transcriptase, 100 or 300 units of T7 RNA polymerase, and either 0 or 2 Units of *E. coli* RNAse H. After incubating one hour at 37° C., 10 μl of each reaction was assayed using the hybridization assay. The results presented in Table 8 showed that the calf thymus DNA inhibited the reaction by 90% in comparison to a reaction system without exogenous DNA and that additional reverse transcriptase (and its associated RNAse H) did not significantly affect the product amplification. The addition of more T7 RNA polymerase did have a significant effect on the product yield, but it was small relative to the increase due to addition of exogenous RNAse H. Not only was the inhibition eliminated, the amplification was increased over five-fold relative to the reaction without the calf thymus DNA and E. coli RNAse H. The signals observed with the higher amount of E. coli RNAse H were saturating for the amount of probe used in the hybridization assay. To accurately quantitate these samples, dilution of the amplified product would be required before assaying.

TABLE 8

Effect of RNAse H on Amplification Inhibition by Exogenous DNA

| Reverse Transcriptase (Units) | T7 RNA Polymerase (Units) | E. coli RNAse H (Units) | Target DNA (amol) | Exogenous DNA (μg) | Relative Light Units |
|---|---|---|---|---|---|
| 13 | 100 | 0 | 0 | 0 | 458 |
| 13 | 100 | 0 | 100 | 0 | 55305 |
| 13 | 100 | 0 | 100 | 2 | 3003 |
| 39 | 100 | 0 | 100 | 2 | 2786 |
| 13 | 300 | 0 | 100 | 2 | 5434 |
| 39 | 300 | 0 | 100 | 2 | 6831 |
| 13 | 100 | 4 | 100 | 2 | 278666 |
| 39 | 100 | 4 | 100 | 2 | 334649 |
| 13 | 300 | 4 | 100 | 2 | 359101 |
| 39 | 300 | 4 | 100 | 2 | 375043 |

Example 9

Amplification by the General Method

This system does not require an initial transcription and denaturation; a DNA complement of the target is made and the original target is removed by the RNAse H. The DNA may then anneal to a second primer or promoter-primer and through DNA synthesis produce a template for the RNA polymerase. If the RNAse H is not active, the DNA:RNA hybrid produced first will end the reaction without producing a template for the RNA polymerase. In an attempt to demonstrate the method of this invention, a plasmid containing an RNA polymerase promoter and the target nucleic acid was used to produce large quantities of single-stranded RNA transcripts containing the target sequence within other sequences. Two similar reactions were also prepared: one containing the plasmid without the RNA polymerase and the other with the RNA polymerase without the plasmid. Dilutions of each of these reactions were assayed to quantitate the products. Equivalent dilutions of all three reactions were used to prepare amplification reactions containing the two promoter-primers, T7 pro(+) and T7 pro(-). Reaction 1 of Table 9 contained 60 amol of RNA and 0.6 amol of the starting plasmid. Reaction 2 contained 0.6 amol of the starting plasmid, but no RNA. Reaction 3 contained no target. The reactions were not denatured at 95° C.; instead reverse transcriptase and T7 RNA polymerase were added and the reaction was incubated at 37° C. for four hours. Aliquots were removed hourly for later assay by the hybridization method. As shown in Table 9, the reaction containing the plasmid and the RNA produced from the plasmid gave large hybridization signals; the reaction containing the plasmid alone produced significant product as the T7 RNA polymerase could produce RNA from the plasmid which could then be utilized according to the General Method to produce more nucleic acid of both senses; and, finally, the control (Reaction 3) containing no target produced nothing.

TABLE 9

Preliminary Procedure IV Reaction Kinetics.

| Time (hours) | Reaction | | | | | |
|---|---|---|---|---|---|---|
| | 1 | 2 | 3 | 1 | 2 | 3 |
| | RLU's for Probe(+) | | | RLU's for Probe(-) | | |
| 2 | 9695 | 1890 | 886 | 7979 | 1074 | 434 |
| 3 | 22266 | 2819 | 824 | 15018 | 1487 | 491 |
| 4 | 33863 | 4571 | 828 | 16540 | 2310 | 556 |

Rxn 1: plasmid plus RNA.
Rxn 2: plasmid.
Rxn 3: no target

Example 10

Amplification by the General Method

The following experiment was done to determine if other methods of initiation were possible for the invention which may alleviate the need for the first primer extension and denaturation step for DNA targets without defined termini. In this experiment, the stated quantities of target are amplified with or without the first reverse transcriptase step as indicated in Table 10. The amplification time once all enzymes are added was four hours. The target used was the M13(+) diluted into normal saline. T7pro(+) and T7pro(-) were used. To 25 μl of each dilution was added 25 μl 0.1N KOH. The samples were incubated ten minutes at 98° C. and then cooled. Each sample was brought to 100 μl and final concentrations of 50 mM Trizma base, 40 mM glutamic acid, 25 mM potassium hydroxide, 12.8 mM magnesium chloride, 5 mM dithiothreitol, 2 mM spermidine trihydochloride, 2.5 mM each ribonucleotide triphosphate, 0.2 mM each deoxyribonucleotide triphosphate, and 0.15 μM each primer. To the Standard Protocol tubes, 13 U reverse transcriptase was added and the reactions were incubated 12 minutes at 42° C., then two minutes at 95° C., and cooled. Then to all tubes was added 13 U reverse transcriptase, 100 U T7 RNA polymerase, and 0.5 U RNAse H. The reactions were then incubated four hours at 37° C. and 10 μl aliquots were assayed using the chemiluminescent probe assay. The results presented in Table 10 show that some amplification was evident using the abbreviated protocol. And although the level of amplification observed was significantly less than that for the Standard Protocol, this may be further developed to be as efficient or may be useful in cases where significant levels of target nucleic acid are present.

TABLE 10

Amplification Without First Primer Extension

| Target | Moles | Protocol | RLU's |
|---|---|---|---|
| M13 (+) | 3.8E-17 | Standard | 2295451 |
| " | 3.8E-19 | " | 2374443 |
| " | 3.8E-21 | " | 230227 |
| Negative | 0 | " | 3037 |
| M13 (+) | 3.8E-17 | Short | 2475574 |
| " | 3.8E-19 | " | 27209 |
| " | 3.8E-21 | " | 17144 |
| Negative | 0 | " | 1679 |

The likely explanation for these data is that T7RNA polymerase is not completely specific. There is a low level of random RNA synthesis which generates small numbers of RNA copies of the target regions. These copies are amplified via the standard method.

Our initial work demonstrated excellent amplification with certain primer sets and targets without the addition of exogenous RNAse H. Our subsequent work clarifying the mechanism of the reaction has made it possible to efficiently apply the method to a wider variety of targets. We disclose and claim herein methods which both use exogenous RNAse H in amplification and those which rely on RNAse H activity associated with reverse transcriptase.

We have discovered that *E. coli* RNAse should not routinely be added as it does not always improve amplification. We have determined that some forms of RNAse H are sequence specific as to where they cut the RNA of RNA:DNA hybrids. In the amplification reaction, we have not detected the promoter-containing primer in full-length product DNA. In embodiments using two promoter-primers, only one of the promoter primers is detectably incorporated into full-length product DNA. All other mechanisms that have been postulated by those skilled in the art show full-length product DNA containing both primers. We attribute these findings to the likelihood that RNAse H is not fully degrading the major RNA species synthesized during amplification. Based on these findings, a new amplification mechanism is set forth herein which incorporates our findings regarding RNAse H sequence specificity. New and useful promoter-primer design criteria are disclosed. Furthermore, we claim herein novel methods for synthesizing multiple copies of a target nucleic acid sequence, comprising 1) selecting a primer, complementary to a portion of the RNA target sequence, which complexes with the portion of the RNA target, said portion of the target located such that it remains capable of forming primer extension product after being exposed to degradation by a selected RNAse H;

2) selecting a promoter-primer complementary to a portion of the DNA to be obtained by extension of the primer, which complexes with the DNA in an area where substantially all of the complementary RNA is removed from the duplex through degradation of RNAse H; and 3) combining the RNA target with the primer, promoter-primer, RNAse H, reverse transcriptase and transcripase and forming multiple copies of the RNA and multiple copies of DNA complementary to the RNA. The novel methods herein described do not make a substantially equivalent number of copies of DNA of the same polarity (or "sense") as the RNA target sequence.

This procedure provides a method which permits the design of efficient promoter-primers and primers for new target sites. We disclose and claim herein such promoter-primer and primer combinations and design criteria for same. The mechanism disclosed herein involves a novel reaction intermediate for transcription of RNA strands. This intermediate is a double-stranded complex of RNA and DNA which contains a double-stranded DNA promoter region. Nothing like this has, to our knowledge, ever been described in the literature. Indeed, none of the prior art systems, specifically neither Guatelli, J. C. et al., 87 *PNAS* 1874–1878 (1990), nor PCT App. Ser. No. 88/10315 to Gingeras, T. R. et al., properly select the primer and promoter-primer sequence based upon the location of RNAse H degradation sites. Thus, the methods herein are novel and nonobvious from any previously disclosed.

Recognition of the importance of the RNAse H sequence specificity and an understanding of the reaction mechanism is key to the efficient application of this target amplification method to a wide variety of target sequences. Moreover, until this time, practitioners assumed that RNAse H fully and systematically degraded the RNA strand of an RNA:DNA complex.

I. The Mechanism of Amplification Methods

Testing amplification efficiency with both prior art methods revealed a great deal of variability in amplification efficiency with small changes in the primer sets used. The reaction method generally accepted in the prior art did not, in our view, provide a reasonable explanation as to why one primer set worked so much better than another.

Attempts to improve amplification using the prior art methods did not give satisfactory results. Efficiency of priming was examined to see if differences in the ability to initiate DNA chains were responsible for observed differences in primer set efficiency. No correlation between priming efficiency and overall amplification could be found. Analysis of primer sets for the ability to form self-complementary structures and cross-complementary structures indicated that differences in primer efficiency were not solely attributable to these factors either.

We also found that the addition of *E. coli* RNAse H did not uniformly improve amplification. As the data submitted herein show, the results observed varied from target to target and from primer set to primer set. The amount of *E. coli* RNAse H added also is very important and must be kept within a narrowly defined range. With a given target and primer set, addition of *E. coli* RNAse H is helpful in some cases when the reverse transcriptase is that from avian myeloblastosis virus ("AMV") but not when the reverse transcriptase is that from Moloney murine leukemia virus ("MMLV"). Data illustrating these conclusions are provided herein.

Earlier work suggested that AMV reverse transcriptase leaves relatively large fragments when it digests the RNA from the RNA:DNA hybrid formed during virus replication. These fragments serve as primers to initiate synthesis of the second DNA strand. We report herein our findings that there is evidence for sequence specificity of the AMV and MMLV RNAse H activities.

In order to elucidate the mechanism of the reaction, individual primers were terminally labeled with $^{32}P$, and the incorporation of each primer into DNA products was examined by polyacrylamide gel electrophoresis. According to the generally accepted prior art mechanism, both primers would be incorporated into full length DNA products. Our experiments showed, however, that only the primer complementary to the major RNA species synthesized during amplification was incorporated into full length product. The primer having the same polarity as the major RNA strand was never detected in full length DNA product. In fact, it remained quite small. These results were confirmed with a number of different targets and primer sets.

The failure to detect extension of one of the primers indicated that a fully double-stranded DNA intermediate did not accumulate during amplification, and was not required for autocatalytic amplification. These observations indicate a mechanism for the amplification systems of this invention which takes into account probable sequence specificities of the RNAse H. The mechanism is generally depicted in FIG. 4.

Figure 5:
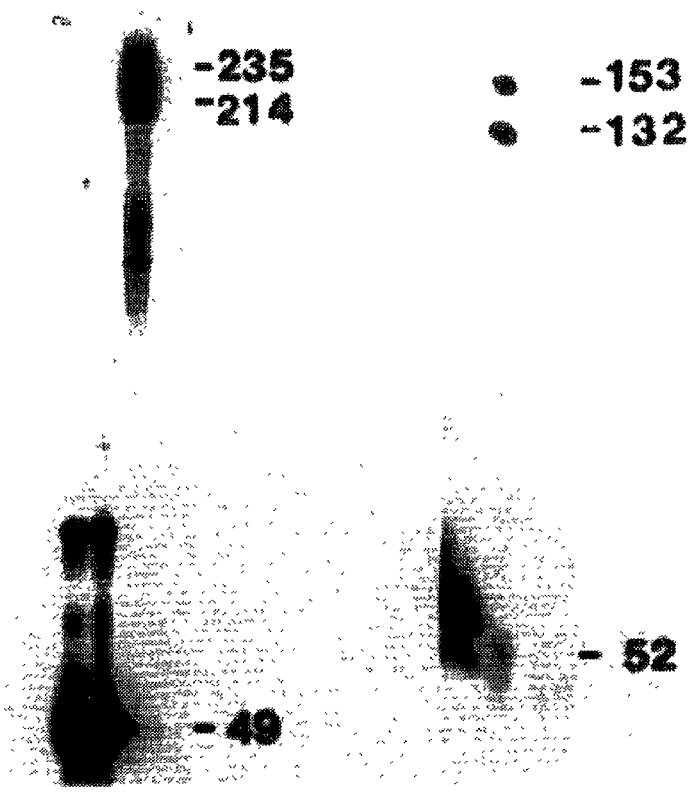
FIG. 5 shows the results of experiments testing the hypothesis that RNAse H from AMV and MMLV and *E. coli* have specific RNA cleavage sites.

Experiments have shown that the enzyme cuts the RNA of an RNA:DNA hybrid into specific pieces. Furthermore, the locations of the cut sites were shown to be in specific regions. To confirm the mechanism, an RNA:DNA hybrid was prepared which contained the plus strand RNA that would be generated from our T7pro$^+$/T7pro$^-$ target and primer set combination. The $^{32}$P labelled RNA was hybridized to complementary DNA, incubated with AMV reverse transcriptase (containing its associated RNAse H activity), and the reaction products were analyzed by polyacrylamide gel electrophoresis (FIG. 5). The fragment size indicated that several small pieces were generated and that these were produced by cuts near one or both ends. The interior region of the molecule was not cut. This experiment demonstrates that the enzyme has sequence or structural specificity under the reaction conditions used. The results were entirely consistent with the reaction mechanism of FIG. 4.

Further experiments were performed to determine where the cut sites occurred. It is preferred that multiple cut sites occur in the region homologous to the promoter-containing primer and not in the region binding the other primer. By labeling the termini of the RNA individually and analyzing the digestion products, it was found that under the conditions used the cuts were detected only at the 5' end of the RNA. This is consistent with the mechanism of FIG. 4.

Sequencing experiments were performed to determine the sequences at which the RNAse H activities of AMV and MMLV reverse transcriptases cut. Sequences were identified that were specifically cut by each enzyme. As predicted, the sequence specificities of the two enzymes are different, and this is believed to explain why some primer sets work better with one enzyme and some with another. The sequence specificities obtained for the MMLV enzyme under our reaction conditions do not match those reported in the literature under another set of reaction conditions, indicating that specificity may be influenced by reaction conditions.

Scrutiny of the role of the RNAse H in the amplification mechanism has resulted in our finding that completely removing the promoter directed transcript from its cDNA copy may not be necessary, or even desirable for formation of a new transcriptionally active template. Thus, in some applications, even a very low level of RNAse H activity, deriving from the reverse transcriptase-intrinsic RNAse H, will be sufficient for effective amplification if the RNase H is more site selective in allowing the promoter-primer to anneal to the first strand cDNA product or if it interferes less with the annealing of the other primer to the transcript.

Since *E. coli* RNAse H is reportedly less specific than the retroviral enzymes, it may cleave in the region to which the non-promoter containing primer binds, especially if the concentrations of this primer, the target, the *E. coli* RNAse H, and components affecting the enzyme activity are not carefully balanced. In our view these results make the use of *E-coli* RNase H non-preferable in commercial applications. Addition of another RNAse H activity, one with different specificities, may be useful in those cases in which the reverse transcriptase RNAse H does not cut in the desired regions or does not cut under appropriate conditions. Work with MMLV reverse transcriptase, for example, has shown that this enzyme is less sensitive than the AMV enzyme to inhibition by sample DNA. It is the best mode for many systems.

New primer sets were designed and are set forth herein based upon the model and the RNAse H sequence specificity information that we have obtained to date. Significantly better synthesis was obtained from these primer sets than was obtained with those designed previously without knowledge of the mechanism and sequence specificities. The invention herein described makes possible the design of functional primer sets for specific target regions.

The new mechanism we have discovered involves a novel reaction intermediate for transcription of RNA strands. This intermediate is a double-stranded complex of RNA and DNA which also contains a double stranded DNA promoter region. To our knowledge, the reaction is demonstrably different from any previously disclosed.

An understanding of the reaction mechanism is critical to using these target amplification procedures. Recognition of the importance of the RNAse H sequence specificity is key to the efficient application of this target amplification method to a wide variety of target sequences. On the other hand, the empirical approach to promoter-primer design is very intensive, costly, and has a low frequency of success, making this invention a useful advance in the art.

A. Narrow Range of Activity for RNAse H Concentration

The amplification system with *E. coli* RNAse H initially was considered to be the preferred embodiment because greater synthesis was achieved with the particular target and primer set being studied, and the *E. coli* RNAse H was found to be useful in helping to overcome inhibition by sample DNA. However, analysis of the reaction indicates that addition of *E. coli* RNAse H is detrimental to amplification in many cases. Moreover, amounts of *E. coli* RNAse H added must be carefully controlled over a narrow range since the presence of too much or too little is harmful. For practical commercial application of the method, this is a significant drawback, especially since the enzyme may not be completely stable on storage. In addition, the use of *E. coli* RNAse H adds significant cost and complexity to the system. The cost may be prohibitive for many commercial applications. Using *E. coli* RNAse H makes the assay more complex, which in turn increases research and development costs and may make the assay too delicate for wide commercial application. Thus, our elucidation of the assay mechanism has resulted in methods for a widely applicable assay both in terms of technical feasibility (applicability to target sites) as well as being a cheaper and a more robust procedure. Since the addition of *E. coli* RNAse H was found to result in increased amplification in early experiments, the effect of *E. coli* RNAse H on the performance of the amplification system in samples containing serum or human DNA was examined in several experiments.

Example 11

Optimization of *E. coli* RNAse H Concentration

Experiments were performed to determine the amount of *E. coli* RNAseH needed for optimal amplification in serum. The following experiment compared amplification with the T7pro$^+$/T7pro$^-$ primer pair in the presence of 0, 0.25, 0.5 and 1 U of RNAseH per assay. HBV+plasma diluted to the levels shown in HBV– human serum or HBV– serum alone was tested.

Ten μl of serum were added to an equal volume of 0.1 N KOH and covered with a layer of oil to prevent evaporation. The samples were mixed, heated at 95° C. and allowed to cool to room temperature. The samples were brought to 90 μl reaction volume with a final concentration of 50 mM Tris acetate pH 7.6, 20.8 mM MgCl$_2$, 5 mM dithiothreitol, 2 mM spermidine hydrochloride, 0.15 μM each primer, 6.25 mM GTP, 6.25 mM ATP, 2.5 mM UTP, 2.5 mM CTP, 0.2 mM each dTTP, DATP, dGTP, dCTP and 13 U of AMV reverse transcriptase. The samples were mixed and heated at 37° C. for 12 minutes, then heated to 95° C. and cooled to room temperature. Thirteen units of RT and 100 U of T7 RNA polymerase were added and the reactions were incubated for three hours at 37° C. Twenty-five μl of each reaction was assayed.

The data show that there is a narrow optimum range of concentration of E. coli RNAse H centering around 0.25 U E. coli RNAse H per reaction for this system. Even though E. coli RNAse H is difficult to use, some added RNAse H activity was beneficial in this experiment.

TABLE 11

| Moles Target | RNAseH (Units) | RLU observed |
| --- | --- | --- |
| $5 \times 10^{-20}$ | 0 | 567809 |
| $5 \times 10^{-22}$ | | 18041 |
| $5 \times 10^{-23}$ | | 2938 |
| 0 | | 1634 |
| $5 \times 10^{-20}$ | 0.25 | 1153366 |
| $5 \times 10^{-22}$ | | 732109 |
| $5 \times 10^{-23}$ | | 5566 |
| 0 | | 1423 |
| $5 \times 10^{-20}$ | 0.5 | 1001904 |
| $5 \times 10^{-22}$ | | 29596 |
| $5 \times 10^{-23}$ | | 1793 |
| 0 | | 1898 |
| $5 \times 10^{-20}$ | 1.0 | 610485 |
| $5 \times 10^{-22}$ | | 13026 |
| $5 \times 10^{-23}$ | | 4062 |
| 0 | | 1662 |

Example 12

Next the amount of E. coli RNAse H needed for optimal amplification of an HIV primer pair was determined in the presence or absence of a lysate containing 8 μg of human DNA. $2 \times 10^{-18}$ moles of viral target were present in each reaction. DNA target was mixed with 50 pmol of each primer in 40 mM Tris HCl pH 8.3, 25 mM NaCl, 20.8 mM MgCl$_2$, 5 mM dithiothreitol, 2 mM spermidine hydrochloride, and nucleotide triphosphates as described for Table 11, heated to 95° C. and cooled to room temperature. Thirteen units of AMV reverse transcriptase were added and the reaction heated to 42° C. for 12 minutes, to 95° C. and cooled again to room temperature. Thirteen units of AMV reverse transcriptase and 100 units of T7 RNA polymerase were added and the reactions heated to 37° C. for 3.5 hours prior to assay.

TABLE 12

| Lysate | RNAse H | RLU |
| --- | --- | --- |
| − | 0 U | 8,400 |
| − | 0.5 | 239,000 |
| − | 1.0 | 468,000 |
| − | 1.5 | 498,000 |
| − | 2.0 | 439,000 |
| − | 3.0 | 20,100 |
| − | 4.0 | 5,806 |
| + | .0 | 1,667 |
| + | 0.5 | 924 |
| + | 1.0 | 6,635 |
| + | 1.5 | 579 |
| + | 2.0 | 13,400 |
| + | 3.0 | 17,800 |
| + | 4.0 | 9,152 |

These results illustrate that E. coli RNAse H levels have to be carefully controlled as too much E. coli RNAse H was detrimental to the amplification. Additionally, the optimal concentration was altered by the presence of nonspecific human DNA and the inhibition by human DNA was significant at all RNAse H levels.

Example 13

We investigated the effect of E. coli RNAse H on amplification of a second region referred to as HIV region 2. The following data demonstrate that E. coli RNAse H enhances amplification within a narrow concentration range. The HIV region 2 primers were amplified as described for Table 12 in the presence of different concentrations of E. coli RNAse H. Ten microliters of each reaction were assayed and dilutions were made when necessary. Signals were compared to a standard curve to determine the amount of target made.

| RNAse H | pmole target | pmole product | Amplification observed |
| --- | --- | --- | --- |
| — | 0 | 0 | 0 |
| — | $1.67 \times 10^{-10}$ | 2.14 | $1.3 \times 10^{10}$ |
| 0.2 U | $1.67 \times 10^{-10}$ | 0.17 | $1.0 \times 10^{9}$ |
| 0.4 U | $1.67 \times 10^{-10}$ | 0.18 | $1.1 \times 10^{9}$ |
| 1.2 U | $1.67 \times 10^{-10}$ | 0.012 | $7.6 \times 10^{7}$ |
| — | $1.67 \times 10^{-8}$ | 16.0 | $9.6 \times 10^{8}$ |
| 0.2 U | $1.67 \times 10^{-8}$ | 20.6 | $1.2 \times 10^{9}$ |
| 0.4 U | $1.67 \times 10^{-8}$ | 0.14 | $8.5 \times 10^{6}$ |
| 1.2 U | $1.67 \times 10^{-8}$ | 0.15 | $9.0 \times 10^{6}$ |

These data show that amplification can be achieved without the addition of E. coli RNAse H, contrary to the assertions of Guatelli, et al., 87 PNAS 1874–1878.

We investigated using E. coli RNAse H with MMLV reverse transcriptase in several target regions. Reactions were done in the presence or absence of 8 μg human DNA using conditions described for Example 12, with a 3 hour autocatalysis step. Primer sets from HIV regions 1, 3 and 4 were tested. The amount of viral template used was selected to give RLU in the linear range of the hybridization assay. MMLV reverse transcriptase was used at 400 U during initiation, 800 U for efficient amplification. 400 U of T7 RNA polymerase were included, and 1 U of E. coli RNAse H was added as indicated. Values presented under the column headings, +RNAse H, −RNAse H, are RLUs obtained from assay of 10 μl of the reactions.

TABLE 15

| Target Region | Moles Target | Human DNA | +RNAse H | −RNAse H |
| --- | --- | --- | --- | --- |
| HIV region 1 | $2 \times 10^{-21}$ | — | 54,900 | 137,000 |
| HIV region 1 | $2 \times 10^{-21}$ | 8 μg | 15,100 | 13,800 |
| HIV region 3 | $2 \times 10^{-20}$ | — | 96,100 | 391,000 |
| HIV region 3 | $2 \times 10^{-20}$ | 8 μg | 124,000 | 246,000 |
| HIV region 4 | $2 \times 10^{-21}$ | — | 20,400 | 107,000 |
| HIV region 4 | $2 \times 10^{-21}$ | 8 μg | 56,000 | 8,800 |

In the presence of DNA, E. coli RNAse H apparently stimulated amplification directed by the HIV region 4 primers. In most cases we have tested, amplification using MMLV reverse transcriptase alone is at least as good as when MMLV reverse transcriptase is used with E. coli RNAse H. E. coli RNAse H is not required for efficient amplification, contrary to the assertions of Guatelli, et al., 87 PNAS 1874–1878.

Sequence Specificity of Reverse Transcriptase

We also have discovered that some primer sets work best with AMV reverse transcriptase while others work best with MMLV reverse transcriptase or with one of the reverse transcriptases and added E. coli RNAse H. The observed degree of variability in amplification efficiency with small changes in promoter primers and primers or source of RNAse H supports our proposed mechanism. We set forth below our detailed data in support of these findings.

MMLV reverse transcriptase has been cloned, and is commercially available from BRL (Bethesda Research Labs), U.S. Biochemicals and others in a very concentrated form (greater than 300 units per µl). It should be noted that comparable DNA synthetic activity on natural nucleic acid templates is obtained with approximately 10-fold greater unit concentration of MMLV reverse transcriptase compared to AMV reverse transcriptase. Lack of comparability in unit activity is due to the fact that the enzymes show different relative activities when tested with homopolymer templates (used in the unit activity assay) and heteropolymeric nucleic acid templates. We tested the use of MMLV reverse transcriptase at various levels in our amplification reactions. Examples of these results are shown in the tables below. In the AMV reverse transcriptase samples, reverse transcriptase was used at 14 U during the initiation step and 56 U during the amplification step. The amount of MMLV reverse transcriptase was titrated for both the initiation and the amplification steps. The incubation conditions used were as described for Example 12 except that 15 pmol of each HIV region 2 primer was used and 25 mM KCl replaced the NaCl. T7 polymerase was used at 400 U during the amplification. The following table shows performance in the presence or absence of 8 µg human DNA. Columns headed with the designation AMV or MMLV show the results of amplifications performed with AMV reverse transcriptase or MMLV reverse transcriptase, respectively. The numbers refer to the number of units used during initiation and autocatalysis, respectively. The values contained within the table are RLUs. Note that dilutions of the amplification products were not performed and values >200,000 RLU may significantly underestimate the extent of amplification since signal saturation occurs at a level of hybridization target sufficient to give about 250,000 RLU with the conditions used.

TABLE 16

| Moles Target | Human DNA | AMV 14/56 | MMLV 400/400 | MMLV 400/600 | MMLV 400/800 |
|---|---|---|---|---|---|
| 0 | − | 495 | 470 | — | 3,800 |
| $1.6 \times 10^{-22}$ | − | 278,000 | 77,000 | — | 5,621 |
| $1.6 \times 10^{-20}$ | − | 292,000 | 278,000 | — | 269,000 |
| 0 | + | 474 | 547 | 488 | 1,352 |
| $1.6 \times 10^{-20}$ | + | 10,200 | 62,700 | 205,000 | 149,000 |

Although the sensitivity of amplification directed by MMLV reverse transcriptase in the absence of human DNA was significantly lower than AMV directed amplification, the MMLV was much more effective in the presence of exogenous DNA.

After observing the high level amplification of the HIV region 2, we tested the other target regions in the presence of human DNA and found that, using AMV reverse transcriptase, E. coli RNAse H was still required for the most effective amplification in these regions. We then tested each target region using MMLV reverse transcriptase, without E. coli RNAse H, to compare amplification performance with reactions containing AMV reverse transcriptase+E. coli RNAse H. An example of these results for two target regions is shown in the table below. The HIV region 3 and 4 primers were used (50 pmol per reaction) as described for Example 12. In reactions using AMV reverse transcriptase, 14 U was used at initiation, 56 U reverse transcriptase+1 U E. coli RNAse H were added for amplification. In reactions using MMLV reverse transcriptase, 400 U was added at initiation and 800 U for amplification. All reactions contained 400 U T7 RNA polymerase during the four-hour amplification incubation. Values within the tables are RLU obtained from Homogeneous Protection Assay performed using 10 µl of the amplification reactions. Dilutions of the reactions were performed in some cases before assay.

TABLE 17

| Moles Target | Human DNA | HIV region 3 AMV | HIV region 3 MMLV | HIV region 4 AMV | HIV region 4 MMLV |
|---|---|---|---|---|---|
| 0 | − | 2,049 | 751 | 1,184 | 777 |
| $1.6 \times 10^{-21}$ | − | 70,800 | 689 | $2.1 \times 10^7$ | 305,000 |
| $1.6 \times 10^{-20}$ | − | 510,000 | 1,869 | — | — |
| 0 | + | 551 | 400 | 1,058 | 1,182 |
| $1.6 \times 10^{-21}$ | + | — | — | 13,900 | 16,200 |
| $1.6 \times 10^{-20}$ | + | 706 | 1,862 | 141,000 | 154,000 |
| $1.6 \times 10^{-19}$ | + | — | — | 683,000 | 723,000 |
| $1.6 \times 10^{-18}$ | + | 10,800 | 115,000 | — | — |

As observed in the HIV region 2, in the absence of human DNA, the amplification with MMLV is significantly less than with AMV reverse transcriptase with E. coli RNAse H but in the presence of DNA the MMLV directed amplification is at least as good as accomplished by AMV reverse transcriptase with RNAse H.

Example 14

Primers for Second Region of HBV Genome

The following experiment was performed with primer sets directed to two regions of the HBV genome. The data show that the primer sets do not amplify to the same extent with AMV RT. The experiment was performed as described for Example 11 using HBV positive plasma diluted in negative serum. Ten microliters of amplification reaction were tested in the hybridization assay.

TABLE 18

| | RLU observed | |
|---|---|---|
| Moles Target | HBV Region 1 | HBV Region 2 |
| $4.8 \times 10^{-21}$ | | 690,674 |
| $4.8 \times 10^{-22}$ | 475,849 | 73,114 |
| $4.8 \times 10^{-23}$ | 242,452 | 4,193 |
| 0 | 1,417 | 1,940 |

These results were confirmed by additional experiments using standard protocols. The region 1 primers consistently gave higher RLU in these experiments.

In contrast, when 800 U of MMLV enzyme were used to amplify the same two primer pairs, the opposite effect was seen as shown below.

TABLE 19

| | RLU observed | |
|---|---|---|
| Moles Target | Region 1 | Region 2 |
| $9.6 \times 10^{-20}$ | 37,278 | 1,067,951 |
| $9.6 \times 10^{-22}$ | 1,858 | 40,826 |
| 0 | 1,010 | 1,646 |

In this experiment, each reaction contained 5 µl serum.

Thus, the amplification potential of each primer pair was influenced by the reverse transcriptase present during amplification. Factors such as the availability of the template sequences, ability of the primers to hybridize specifically, and efficiency of RNA synthesis should not be affected significantly by the type of reverse transcriptase present. Factors such as RNAse H specificity and activity and DNA polymerizing activity could be affected.

The following data illustrates that promoter-primer combinations used in the appropriate conditions can be designed to increase amplification.

TABLE 21

This experiment was performed with HBV region 2 primers as described for Table 11 except that the entire amplification reaction was analyzed by hybridization.

| Target Molecules | Moles Target | RLU Observed |
|---|---|---|
| 1200 | $2 \times 10^{-21}$ | 1,094,177 |
| 120 | $2 \times 10^{-22}$ | 442,137 |
| 12 | $2 \times 10^{-23}$ | 24,053 |
| 1.2 | $2 \times 10^{-24}$ | 8,654 |
| 0 | 0 | 1,828 |

Example 15

Comparison of AMV Reverse Transcriptase and MMLV Reverse Transcriptase

The following experiment compared amplification of primers for a BCL-2 chromosonal translocation major human chromosomal breakpoint t(14;18) found in patients with CML using MMLV (300 units) or AMV (39 units). The effect of E. coli RNAse H was evaluated with each enzyme. Amplifications were performed as described for Example 12 except that 24 mM $MgCl_2$ and 50 pmol each primer were used. In reactions containing lysate, 4 µg of DNA from white blood cells was present. All reactions contained 300 units T7 RNA polymerase and 10 amol of input double-stranded DNA target.

TABLE 22

| RT | Lysate | 0 Units RNAse H | 0.5 Units RNAse H | 1.0 Units RNAse H | 2.0 Units RNAse H |
|---|---|---|---|---|---|
| AMV | − | 108,018 | 2,035,377 | — | — |
|  | + | 44,485 | 204,894 | 165,972 | 136,647 |
| MMLV | − | 3,015,948 | 2,224,666 | — | — |
|  | + | 3,070,136 | 2,714,257 | 767,218 | 105,845 |

The results show that MMLV and AMV RT do not amplify this primer set to the same extent, particularly in the absence of E. coli RNAse H. E. coli RNAse H added to reactions containing AMV reverse transcriptase markedly improved amplification; this indicates that the RNAse activity was limiting in these reactions. In contrast, E. coli RNAse H did not enhance amplification when added to reactions containing MMLV RT. The data also confirms a point already made concerning the ability of MMLV RT to sustain significant amplification in the presence of large amounts of nonspecific human DNA.

C. One Primer was not Incorporated into Full Length Product

One of our most important findings is that the primer of the same polarity as the major RNA species was not detectably incorporated into full length DNA product. To demonstrate this, individual primers were terminally labeled with $^{32}P$, and the incorporation of each primer into DNA products was examined by polyacrylamide gel electrophoresis. We initially expected both primers to be incorporated into full length DNA products. However, the primer containing the promoter was not observed in full length DNA product. In fact, it remained quite small. These results were confirmed with a number of different targets and primer sets. Our method is explained below.

To identify the species of cDNA accumulated during autocatalysis, primers were $^{32}P$-labeled at the 5' end with T4 polynucleotide kinase and spiked into amplification reactions. The following examples show that cDNA of one polarity is preferentially accumulated during amplification, and that the accumulated strand is always complementary to the predominant RNA species synthesized during autocatalysis. FIG. 5 shows the result of incorporation of $^{32}P$-labeled HIV region 2 primers during amplification. This primer set results in synthesis of a 214 base RNA of the (+) sense. The primer complementary to the RNA was incorporated into two major bands of 235 and 214 bases when target sequences were present (lane 3). No full length fragments were seen in the absence of target (lane 4). The 214 base fragment represents cDNA equal in length to the RNA while the 235 base fragment is equal in length to the RNA+21 bases of the T7 promoter sequence. In contrast, the promoter primer was not observed in full length DNA product in the presence or absence of target (lanes 1 and 2 respectively).

Lanes 5–8 of FIG. 5 show the result of incorporation of $^{32}P$-labeled HBV region 1 primers during amplification. These are known as T7pro$^+$ and T7pro$^-$. This primer set is capable of producing 132 base RNA of two polarities but the (+) strand RNA predominates. T7pro$^-$, which is complementary to the predominant RNA, was incorporated into fragments of 132 bases and 153 bases consistent with our proposed mechanism (lane 7 (+) target, lane 8, (−) target). The 153 base fragment is equal in length to the RNA+21 bases of the T7 promoter sequence of the T7 pro$^+$. In contrast, $^{32}P$-labeled T7pro$^+$ primer was not incorporated into fragments of either length (lane 5 (+) target, lane 6, (−) target).

The reactions analyzed by gel electrophoresis were also analyzed by HPA to determine if cDNA of the same polarity as the predominant RNA could be detected by another method. Plus and minus strand probes were used to determine the relative ratio of strands made, and a portion of each reaction was treated with RNAse A to determine the ratio of RNA to DNA. The results are set forth below.

TABLE 23

| Probe Polarity | Primer set | RLU No treatment | RLU RNase A |
|---|---|---|---|
| (−) | *HIV Region 2 | 679,182 | 1037 |
|  | HIV Region 2 | 453,675 | 1464 |
| (+) | *HIV Region 2 | 32,922 | 1,094,249 |
|  | HIV Region 2 | 39,494 | 655,595 |
| (−) | *HBV Region 1 | 567,110 | 4,854 |
|  | HBV Region 1 | 671,656 | 4,210 |
| (+) | *HBV Region 1 | 56,550 | 303,160 |
|  | HBV Region 1 | 77,983 | 450,332 |

*= (+) strand primer labeled with $^{32}P$, others, (−) strand primer labeled with $^{32}P$.

These results show that the amplifications worked well, even when full length product was not observed with the promoter primer. These results correlate with what was observed in the previous study, that is, most of the signal observed with one sense probe is from RNA, and the complementary strand signal is as expected, from DNA. This was true even for the HBV region 1 primer set which should have made RNA of both polarities.

D. Confirmation of Mechanism Showing that the Enzyme Cuts RNA of the RNA/DNA Hybrid at Specific Loci Based upon the experiments and observations reported hereinabove, the mechanism for the amplification systems that takes into account probable sequence specificities in the RNAse H is depicted in FIG. 4. In support of this mechanism, since RNAse H sequence specificity is a key element, it is necessary to show that indeed the enzymes cut the RNA of an RNA:DNA hybrid at specific locations. Furthermore, the locations of the cut sites needed to be in specific regions according to the model in order for good amplification to be obtained. To examine this question, an RNA:DNA hybrid was prepared that contained the RNA that would be generated from a known target and primer set combination. The RNA was labeled with $^{32}$P, incubated with AMV reverse transcriptase (containing its associated RNAse H activity), and the reaction products were analyzed by polycryamide gel electrophoresis. The results were entirely consistent with the new reaction mechanism, namely, the fragment size indicated that several small pieces were generated and that these were produced by cuts near one or both ends. The interior region of the molecule was not cut. This experiment confirmed that the enzyme has sequence or structural specificity under the reaction conditions used.

Further experiments were performed to determine where the cuts occurred since the proposed mechanism requires that multiple cuts occur in the region binding the promoter-containing primer. By labeling the termini of the RNA individually and analyzing the digestion products, it was demonstrated that the cuts were made only at the 5' end of the RNA. This also is consistent with the proposed mechanism.

Example 16

FIG. 6 shows that the RNAse H activities from AMV, MMLV and *E. coli* cut at specific RNAse H cleavage sites. The arrows in the figure indicate the position of full-length RNA.

FIG. 6 shows the result of an experiment in which HIV region 2 RNA was internally labelled with $^{32}$P, hybridized to a single-stranded target sequence and nicked with RNAse H from AMV for 45 minutes (lane 2), MMLV for 5, 15, 45 or 120 minutes (lane 3–6) or *E. coli* RNAse H for 5 minutes (lane 7). The sizes of fragments produced were discrete and different with each enzyme, indicating specificity of cleavage of the enzymes and varied specificity among enzymes with this template. The most rapid degradation was observed in the presence of *E. coli* RNAse H, indicating less specificity or greater activity of cutting with this enzyme.

Figures 6A, 6B:
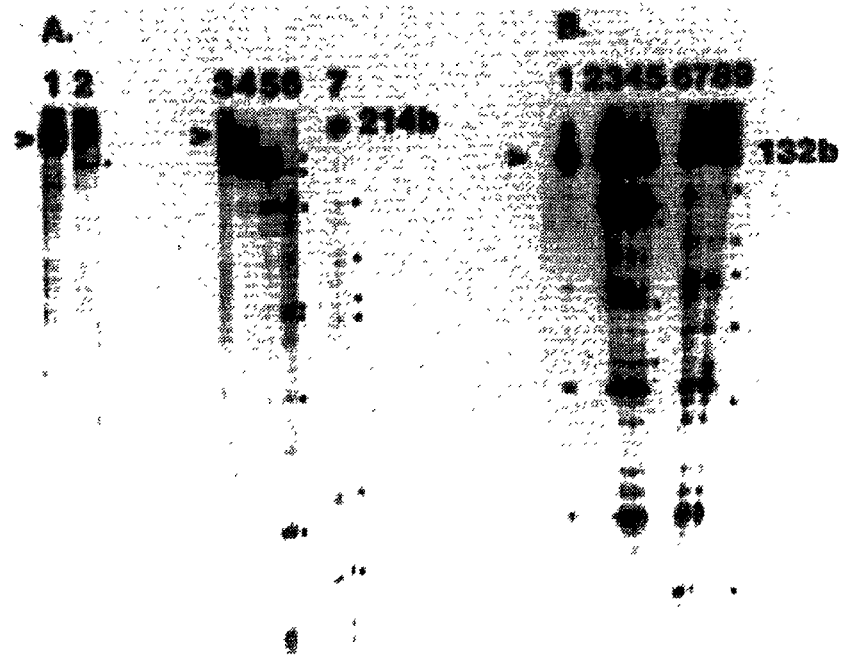
FIG. 6 shows the results of incorporation of $^{32}$p-labeled primers during amplification.

FIG. 6b shows the results of hybridization of HBV region 1 RNA to a synthetic target sequence, followed by nicking with RNAse H from AMV reverse transcriptase for 5, 30, 60 or 120 minutes (lanes 2–5) or *E. coli* for 1, 3, 15 or 60 minutes (lanes 6–9). Different sized fragments were produced with the two enzymes, indicating specificity of cleavage. When the HBV RNA was labeled on the 3' terminus and nicked with AMV reverse transcriptase, the same sized fragments were observed, indicating that the cleavage sites were near the 5' end of the RNA.

These data indicate that specific sites are cleaved with RNAse H from AMV, MMLV and *E. coli*, and that at least some sites are different with the three enzymes. The presence of specific sites within the region to be amplified allows the RNA in an RNA:DNA hybrid to be cleaved, allowing autocatalysis to occur efficiently. Primers designed using cut site information show improved amplification efficiency. This is consistent with our observations that certain primer sets amplified to different extents depending on the source of RNAse H.

E. Identification of MMLV and AMV RNAse H Cut Sites

Example 17

To identify sites digested by AMV RNAse H, RNA was hybridized with a complementary sequence and nicked with AMV RNAse H. Following denaturation, a primer complementary to the 3' end of the region to be sequenced was hybridized and extended in the presence of dideoxynucleotides by the Sanger sequencing method. Termination of cDNA synthesis, indicating cleavage of RNA, was observed at the following sites for the HBV RNA:

5'.GGGAGAGGUUAUCGC*UGGA*UGUGUCUGCGG
CGUUUUAUCA*UAU UCCUCUUCA*UCCUG . . . 3'
(SEQ ID NO:32).

To identify sites digested by MMLV RNAse H, RNA was hybridized with a complementary sequence and nicked with MMLV RNAse H. Following denaturation, a primer complementary to the 3' end of the region to be sequenced was hybridized and extended in the presence of dideoxynucleotides by the Sanger sequencing method. Termination of cDNA synthesis was observed at the following sites for the HBV RNA:

5'_GGGAGAGGUUAUCGC*UGGA*UGUGUCUGCGGC*GUUUUAUCA*

UAUUCCUCUUCAUCCUGC*UGCUAUGCCUCA*UCUUC . . . -3'

The following sites were identified for a second HBV RNA sequence:

5'_GGGAGACCCGAGAU*UGA*GAUCUUCUGCGAC

GCGGCGAU*UGA*GAUCUGCGUCU*GCGAGGCGAGGGAGU*UCU*UCUU*

CUAGGGGACCUGCCUCGGUCCCGUC*GUCUA . . . 3'

The following sites were identified for an HIV RNA sequence:

5'_GGGAGACAAA*UGGCAGUA*UUCAUCCAC

AAUUUUAAAAGAAAAGGGGGAUUGGGGGGUA

CAGUGCAGGGGAAAGAAUAGUAGACAUAAUAGC*AACAGACA

UAC*AAACUAAAGAAUUACAAAAACAAAUUAC*AAAAAUUCAA

AAUUUUCGGGUUUAUUACAGGGAC*AGC*AGAAA . . . 3'

Most of the cleavage sites occurred near the dinucleotides CA or UG. The method used for detecting cleavage sites only identified sites which accumulated during the cleavage reaction. It is expected that additional sites could be cleaved which were not recognized by the method used.

F. Primers for Amplification Systems

Based on findings that the various RNAse H enzymes have sequence specificity, we have tested various primer/target combinations and attempted to optimize their performance in amplification systems. Data obtained to date indicates that the piece size of the RNA fragments produced is relatively large and that the fragments probably do not spontaneously dissociate from the duplex. This is not unexpected since work with AMV reverse transcriptase copying AMV RNA or poliovirus RNA showed that the RNA fragments that were produced by the RNAse H were used by the enzyme to prime the synthesis of cDNA from the initially synthesized cDNA strand.

If the RNAse H enzymes have sequence specificity, the amplification reaction proceeds as follows (beginning with the RNA intermediate in the reaction):

The primer complementary to the major RNA species produced during amplification binds at the 3' terminus of the RNA. Since the concentration of primer is high in the reaction, excess primer produces RNA:DNA duplexes which may be cut by the RNAse H activity before being able to initiate synthesis. Therefore, it is preferable that the primer binding region does not contain a large number of sequences recognized by the RNAse H enzyme used in the reaction.

As cut sites occur frequently, it may not be practical in some cases to design an RNA complementary primer without recognized cut sites; in such cases, the cut sites should be as near the 5' terminus as possible to allow the 3' terminal portion of the primer to remain annealed to the RNA.

Upon extension of the primer by a suitable DNA polymerase, the binding site for the second primer, which contains the RNA polymerase promoter, must now be exposed. It is sufficient to remove only a portion of the RNA to allow nucleation and zippering of the primer as it hybridizes to the cDNA, to allow reverse transcriptase mediated binding of the primer and initiation of synthesis, or merely to nick the RNA so that the RNA fragment that results may be displaced. Since our data show relatively large pieces of RNA are made and that the promoter containing primer is not incorporated into full-length DNA, the following events can occur:

1. There is sufficient nicking of the RNA to permit binding of the promoter-primer. Whether a nick in the appropriate place simply produces an RNA fragment sufficiently small to melt off and expose the primer binding site or a portion thereof or whether a nick allows an unwinding activity associated with one or more of the enzymes to displace the RNA fragment is not known at this time.

2. The cDNA 3' terminus is extended by the reverse transcriptase to make the promoter region double-stranded DNA.

3. RNA is synthesized from the complex thus made. This complex would consist of a cDNA bound to RNA and containing a double-stranded DNA promoter.

Thus, there must be a sequence recognized by the RNAse H activity present in the reaction somewhere in or near the binding site for the primer containing the RNA polymerase promoter.

In some applications, it may also be desirable to not have RNAse H recognition sites within the target sequence itself. Sites within the target may be cleaved and used to produce RNA primers for synthesis of double-stranded cDNA regions. It may be preferable to eliminate the possibility of this enzymatic activity.

New primer sets were designed based upon the model and the RNAse H sequence specificity information that we have obtained. Our design criteria are as follows:

For the T7 promoter-primer:
1) The primer region should have one or more cut sites per 10 bases.
2) The primer region should have a cut site near the 5' end.
3) The primer region should have a cut site near the 3' end and possibly a partial site at the 3' end.
4) The primer length should be >18 bases.
5) The $T_m$ estimated should be about 55–65° C.

For the other primer:
1) The primer should have few or no RNAse H cut sites.
2) Any cut sites in the primer should be near the 5' end.
3) The primer length should be about 18–28 bases in length.
4) The $T_m$ estimated should be about 55–65° C.

Significantly better synthesis was obtained from primer sets designed using these criteria and knowledge of the mechanism and sequence specificities. This shows the utility of the invention in making possible the design of functional primer sets for specific target regions. These are explained more fully below.

Example 18

Our findings regarding RNAse H specificity have been used to design efficient promoter-primer combinations. Prior art methods simply nonselectively attached promoters to primer sequences. We have been able to design and optimize promoter-primer combinations to increase the yield of amplified product. The following experiment shows that small changes in promoter-primer sequence result in large changes in amplification efficiency.

The following examples show primers from similar regions which were compared for RNAse H cleavage sites and GP-III amplification efficiency. In each example, duplicate amplifications were performed using common reagents except for the primers being tested.

1. Non-promoter Primers

In the first example, the non-promoter primer site for the CML major t(14; 18) breakpoint amplification region was moved 15 bases, resulting in a reduction in the number of putative RNAse H cut sites from 4 to 1, assuming a 4 base recognition sequence or from 5 to 2 assuming a 3 base recognition sequence. The reaction was performed as described for Example 15 except that 2.5 mM ATP, 16.5 mM $MgCl_2$ and 50 mM KCl were included. This change in primer sequence had a dramatic positive effect on amplification efficiency. In the second case, an intentional mismatch was placed internally in the non promoter primer of HBV region 1 to remove the only putative RNAse H cut site, assuming a 4 base recognition site. In the case of a 3 base cut site, one skilled in the art would recognize that the mismatch removed the cut site nearest the 3' end. This change also had a definitive positive effect on amplification efficiency. The data demonstrate that two methods, changing the position of the primer, or inclusion of mismatches, can be used to enhance amplification. Presumably, removal of RNAse H cut sites from the non-promoter primer results in more efficient priming of cDNA synthesis during autocatalysis.

|  | Sequence | RLU |
|---|---|---|
| Example 1 | GGAGCTGCAGATGCTGACCAAC | 78,880 |
|  | GACCAACTCGTGTGTGAAACTCCA | 2,552,333 |
| Example 2 | TCCTGGAATTAGAGGACAAACGGGC | 57,710 |
|  | TCCTGGAATTAGAGGATAAACGGGC | 518,695 |

2. promoter-primers. The following examples show promoter primers which come from similar regions but which differ in the number of putative RNAse H cut sites. In the first case, the two promoter primer sites for the HIV region 5 are displaced by 10 bases, changing the number of putative RNAse H cut sites from two to three, assuming a four base recognition site, or from 3 to 5 assuming a 3 base recognition site. This has a positive effect on amplification efficiency. In the second case, a sequence containing putative RNAse H cut sites was inserted upstream of the promoter primer for the major breakpoint t(14; 18) translocation, and one mismatch to the target was included to generate a cut site within the primer region. This also had a positive effect on amplification efficiency. This demonstrates that insertion of RNAse H cut sites in the promoter primer can be used to enhance amplification efficiency. Presumably, inclusion of RNAse H cut sites assists in RNA strand displacement, increasing the efficient of copying of the promoter region, thereby resulting in more efficient autocatalysis.

|  | Primer name | RLU |
| --- | --- | --- |
| Example 3 | A | 45,466 |
|  | B | 908,147 |
| Example 4 | C | 64,601 |
|  | D | 2,946,706 |

Sequences of the primers above are:

```
Primer A:
AATTTTAATACGACTCACTATAGGGAGAAATCTTGTGGGGTGGCTCCTTC
T-3'

Primer B:
AATTTAATACGACTCACTATAGGGAGAGGGGTGGCTCCTTCTGATAA
TGCTG-3'

Primer C:
ATTTAATACGACTCACTATAGGGAGACGGTGACCGTGGTCCCTTG-3'

Primer D:
TAAATTAATACGACTCACTATAGGGAGATCAGTTACAATCGC
TGGTATCAACGCTGAGCAGACGCTGACCGTGGTCCCTTG-3'
```

In the above examples, removal of RNAse H cut sites from the non-promoter primer resulted in enhanced amplification, even if the removal of the cut site involved the incorporation of a mismatch to the original target. Design of the promoter-containing primer to include additional RNAse H cut sites also enhanced amplification, again, even if the incorporation of cut sites involved inclusion of mismatches to the original target. The number, distribution, and position of putative RNAse H cut sites determine, in part, the usefulness of a given primer.

Improvement of amplification by inclusion of intentional mismatches or insertion of sequences between the promoter and primer are nonobvious improvements to the amplification method.

In a preferred embodiment of the present invention, the RNA target sequence is determined and then analyzed to determine where RNAse H degradation will cause cuts or removal of sections of RNA from the duplex. Experiments can be conducted to determine the effect of the RNAse degradation of the target sequence by RNAse H present in AMV reverse transcriptase and MMLV reverse transcriptase, by *E. coli* RNAse H or by combinations thereof.

In selecting a primer, it is preferable that the primer be selected so that it will hybridize to a section of RNA which is substantially nondegraded by the RNAse H present in the reaction mixture. If there is substantial degradation, the cuts in the RNA strand in the region of the primer may stop or inhibit DNA synthesis and prevent extension of the primer. Thus, it is desirable to select a primer which will hybridize with a sequence of the RNA target, located so that when the RNA is subjected to RNAse H, there is no substantial degradation which would prevent formation of the primer extension product.

The site for hybridization of the promoter-primer is chosen so that sufficient degradation of the RNA strand occurs to permit removal of the portion of the RNA strand hybridized to the portion of the DNA strand to which the promoter-primer will hybridize. Typically, only portions of RNA are removed from the RNA:DNA duplex by RNAse H degradation and a substantial part of the RNA strand remains in the duplex. An RNA:DNA duplex containing a double-stranded DNA promoter results.

The invention claimed is:

1. An oligonucleotide probe, wherein the base sequence of said probe consists of or is contained within the RNA equivalent of the base sequence of a reference sequence selected from the group consisting of SEQ ID NO:1, SEQ ID NO:4, SEQ ID NO:7, SEQ ID NO:10, SEQ ID NO:13, wherein said probe hybridizes to HIV-derived nucleic acid in a sample to a form a detectable probe:target duplex which indicates the presence of HIV nucleic acid under hybridization conditions, and wherein said probe does not hybridize to human nucleic acid in said sample to form a detectable probe:non-target duplex under said conditions.

2. The probe of claim 1, wherein said reference sequence is SEQ ID NO:1.

3. The probe of claim 1, wherein said reference sequence is SEQ ID NO:4.

4. The probe of claim 1, wherein said reference sequence is SEQ ID NO:7.

5. The probe of claim 1, wherein said reference sequence is SEQ ID NO:10.

6. The probe of claim 1, wherein said reference sequence is SEQ ID NO:13.

7. The probe of claim 1, wherein the base sequence of said probe consists of the RNA equivalent of the base sequence of said reference sequence.

8. The probe of claim 1, wherein said probe includes a detectable label.

9. A kit for detecting whether HIV nucleic acid may be present in a sample comprising:
   a) said probe of claim 1; and
   b) one or more oligonucleotide primers, wherein the base sequence of each said primer consists of or is contained within the base sequence of a reference sequence selected from the group consisting of SEQ ID NO:2, SEQ ID NO:3, SEQ ID NO:5, SEQ ID NO:6, SEQ ID NO:8, SEQ ID NO:9; SEQ ID NO:11, SEQ ID NO:12, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and the RNA equivalents thereof.

10. The kit of claim 9, wherein said primers include first and second primers, and wherein:
    a) said reference sequence for said probe is SEQ ID NO:1;
    b) said reference sequence for said first primer is SEQ ID NO:2; and
    c) said reference sequence for said second primer is SEQ ID NO:3.

11. The kit of claim 9, wherein said primers include first and second primers, and wherein:
    a) said reference sequence for said probe is SEQ ID NO:4;
    b) said reference sequence for said first primer is SEQ ID NO:5; and
    c) said reference sequence for said second primer is SEQ ID NO:6.

12. The kit of claim 9, wherein said primers include first and second primers, and wherein:
    a) said reference sequence for said probe is SEQ ID NO:7;
    b) said reference sequence for said first primer is SEQ ID NO:8; and
    c) said reference sequence for said second primer is SEQ ID NO:9.

13. The kit of claim 9, wherein said primers include first and second primers, and wherein:
    a) said reference sequence for said probe is SEQ ID NO:10;
    b) said reference sequence for said first primer is SEQ ID NO:11; and
    c) said reference sequence for said second primer is SEQ ID NO:12.

14. The kit of claim 9, wherein said primers includes first and second primers, and wherein:
    a) said reference sequence for said probe is SEQ ID NO:13;
    b) said reference sequence for said first primer is SEQ ID NO:14; and
    c) said reference sequence for said second primer is SEQ ID NO:16.

15. A method of determining whether HIV nucleic acid may be present in a sample comprising the steps of:
    a) providing to a sample said probe of claim 1; and
    b) determining whether said probe hybridizes to nucleic acid present in said sample as an indication that HIV nucleic acid is present in said sample.

16. The method of claim 15, wherein said reference sequence is SEQ ID NO:1.

17. The method of claim 15, wherein said reference sequence is SEQ ID NO:4.

18. The method of claim 15, wherein said reference sequence is SEQ ID NO:7.

19. The method of claim 15, wherein said reference sequence is SEQ ID NO:10.

20. The method of claim 15, wherein said reference sequence is SEQ ID NO:13.

21. The method of claim 15, wherein the base sequence of said probe consists of the RNA equivalent of the base sequence of said reference sequence.

22. The method of claim 15, wherein said probe includes a detectable label.

23. The method of claim 15 further comprising the step of amplifying a target sequence contained in HIV nucleic acid.

24. The method of claim 23, wherein said amplifying step is an autocatalytic procedure performed under substantially isothermal conditions.

25. The method of claim 24, wherein said amplifying step is carried out in the presence of reverse transcriptase.

26. The method of claim 25, wherein said reverse transcriptase comprises RNase H activity.

27. An oligonucleotide, wherein the base sequence of said oligonucleotide consists of or is contained within the RNA equivalent of the base sequence of a reference sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, wherein said oligonucleotide hybridizes to HIV-derived nucleic acid in a sample to form an oligonucleotide:target duplex under hybridization conditions, and wherein said oligonucleotide does not hybridize to human nucleic acid in said sample to form an oligonucleotide:non-target duplex under said conditions.

28. The oligonucleotide of claim 27, wherein said reference sequence is SEQ ID NO:1.

29. The oligonucleotide of claim 27, wherein said reference sequence is SEQ ID NO:2.

30. The oligonucleotide of claim 27, wherein said reference sequence is SEQ ID NO:3.

31. The oligonucleotide of claim 27, wherein said reference sequence is SEQ ID NO:4.

32. The oligonucleotide of claim 27, wherein said reference sequence is SEQ ID NO:5.

33. The oligonucleotide of claim 27, wherein said reference sequence is SEQ ID NO:6.

34. The oligonucleotide of claim 27, wherein said reference sequence is SEQ ID NO:7.

35. The oligonucleotide of claim 27, wherein said reference sequence is SEQ ID NO:8.

36. The oligonucleotide of claim 27, wherein said reference sequence is SEQ ID NO:9.

37. The oligonucleotide of claim 27, wherein said reference sequence is SEQ ID NO:10.

38. The oligonucleotide of claim 27, wherein said reference sequence is SEQ ID NO:11.

39. The oligonucleotide of claim 27, wherein said reference sequence is SEQ ID NO:12.

40. The oligonucleotide of claim 27, wherein said reference sequence is SEQ ID NO:13.

41. The oligonucleotide of claim 27, wherein said reference sequence is SEQ ID NO:14.

42. The oligonucleotide of claim 27, wherein said reference sequence is SEQ ID NO:15.

43. The oligonucleotide of claim 27, wherein said reference sequence is SEQ ID NO:16.

44. The oligonucleotide of claim 27, wherein said reference sequence is SEQ ID NO:17.

45. The oligonucleotide of claim 27, wherein said reference sequence is SEQ ID NO:18.

46. The oligonucleotide of claim 27, wherein said reference sequence is SEQ ID NO:19.

47. The oligonucleotide of claim 27, wherein said reference sequence is SEQ ID NO:20.

48. The oligonucleotide of claim 27, wherein said reference sequence is SEQ ID NO:21.

49. The oligonucleotide of claim 27, wherein said reference sequence is SEQ ID NO:22.

50. The oligonucleotide of claim 27, wherein said oligonucleotide is a primer.

51. The oligonucleotide of claim 27, wherein said oligonucleotide is a probe.

52. The oligonucleotide of claim 27, wherein the base sequence of said oligonucleotide is at least 18 bases in length.

53. The oligonucleotide of claim 27, wherein the base sequence of said oligonucleotide is greater than 18 bases in length.

54. The oligonucleotide of claim 27, wherein the base sequence of said oligonucleotide consists of the RNA eqiuivalent of the base sequence of said reference sequence.

55. The oligonucleotide of claim 27, wherein said oligonucleotide includes a detectable label.

56. A method of detecting HIV nucleic acid which may be present in a sample comprising the steps of:
   a) providing to a sample one or more oligonucleotide primers under conditions such that one or more of said primers forms a complex with an HIV-derived target nucleic acid, thereby permitting DNA synthesis to be initiated, wherein the base sequence of each said primer consists of or is contained within the RNA equivalent of the base sequence of a reference sequence selected from the group consisting of SEQ ID NO:2, SEQ ID NO:3, SEQ ID NO:5, SEQ ID NO:6, SEQ ID NO:8, SEQ ID NO:9, SEQ ID NO:11, SEQ ID NO:12, SEQ ID NO:14, SEQ ID NO:15, SEQ ID NO:16, SEQ ID NO:17, SEQ ID NO:18, SEQ ID NO:19, SEQ ID NO:20, SEQ ID NO21, and SEQ ID NO:22;
   b) amplifying a second target sequence contained in said HIV-derived target nucleic acid; and
   c) detecting amplified product from step b) as an indication of the presence HIV nucleic acid in said sample.

57. The method of claim 56, wherein said reference sequence is SEQ ID NO:2.

58. The method of claim 56, wherein said reference sequence is SEQ ID NO:3.

59. The method of claim 56, wherein said reference sequence is SEQ ID NO:4.

60. The method of claim 56, wherein said reference sequence is SEQ ID NO:6.

61. The method of claim 56, wherein said reference sequence is SEQ ID NO:8.

62. The method of claim 56, wherein said reference sequence is SEQ ID NO:9.

63. The method of claim 56, wherein said reference sequence is SEQ ID NO:11.

64. The method of claim 56, wherein said reference sequence is SEQ ID NO:12.

65. The method of claim 56, wherein said reference sequence is SEQ ID NO:14.

66. The method of claim 56, wherein said reference sequence is SEQ ID NO:15.

67. The method of claim 56, wherein said reference sequence is SEQ ID NO:16.

68. The method of claim 56, wherein said reference sequence is SEQ ID NO:17.

69. The method of claim 56, wherein said reference sequence is SEQ ID NO:18.

70. The method of claim 56, wherein said reference sequence is SEQ ID NO:19.

71. The method of claim 56, wherein said reference sequence is SEQ ID NO:20.

72. The method of claim 56, wherein said reference sequence is SEQ ID NO:21.

73. The method of claim 56, wherein said reference sequence is SEQ ID NO:22.

74. The method of claim 56, wherein the base sequence of said primer is at least 18 bases in length.

75. The method of claim 56, wherein the base sequence of said primer is greater than 18 bases in length.

76. The method of claim 56, wherein said primers include a set of said primers.

77. The method of claim 56, wherein said amplifying step is an autocatalytic process which is performed under substantially isothermal condition and which is carried out in the presence of a reverse transcriptase comprising RNAse H activity, said reverse transcriptase being the only source of RNAse H activity present in said sample during said amplifying step.

78. The method of claim 56, wherein said detecting step comprises the step of adding an oligonucleotide probe to the sample, wherein the base sequence of said probe consists of or is contained within a base sequence of a reference sequence selected from the group consisting of SEQ ID NO:1, SEQ ID NO:4, SEQ ID NO:7, SEQ ID NO:10, SEQ ID NO:13, and the RNA equivalents thereof, wherein said probe hybridizes to said amplified product in said sample to a form a detectable probe:target complex which indicates the presence of said HIV nucleic acid under hybridization conditions, and wherein said probe does not hybridize to human nucleic acid in said sample to form a detectable probe:non-target complex under said conditions.

79. The probe of claim 78, wherein the base sequence of said probe consists of the base sequence of said reference sequence for said probe.

80. The method of claim 78, wherein said probe includes a detectable label.

* * * * *

SEQUENCE LISTING

<160> NUMBER OF SEQ ID NOS: 46

<210> SEQ ID NO 1
<211> LENGTH: 28
<212> TYPE: DNA
<213> ORGANISM: Artificial Sequence
<220> FEATURE:
<223> OTHER INFORMATION: Synthesized nucleic acid molecule

<400> SEQUENCE: 1
gcagctgctt atatgcagga tctgaggg                                    28

<210> SEQ ID NO 2
<211> LENGTH: 54
<212> TYPE: DNA
<213> ORGANISM: Artificial Sequence
<220> FEATURE:
<223> OTHER INFORMATION: Synthesized nucleic acid molecule

```
<400> SEQUENCE: 2
aatttaatac gactcactat agggagacaa gggactttcc gctggggact ttcc         54

<210> SEQ ID NO 3
<211> LENGTH: 27
<212> TYPE: DNA
<213> ORGANISM: Artificial Sequence
<220> FEATURE:
<223> OTHER INFORMATION: Synthesized nucleic acid molecule

<400> SEQUENCE: 3
gtctaaccag agagacccag tacaggc                                       27

<210> SEQ ID NO 4
<211> LENGTH: 29
<212> TYPE: DNA
<213> ORGANISM: Artificial Sequence
<220> FEATURE:
<223> OTHER INFORMATION: Synthesized nucleic acid molecule

<400> SEQUENCE: 4
ctactattct ttcccctgca ctgtacccc                                     29

<210> SEQ ID NO 5
<211> LENGTH: 49
<212> TYPE: DNA
<213> ORGANISM: Artificial Sequence
<220> FEATURE:
<223> OTHER INFORMATION: Synthesized nucleic acid molecule

<400> SEQUENCE: 5
aatttaatac gactcactat agggagacaa atggcagtat tcatccaca              49

<210> SEQ ID NO 6
<211> LENGTH: 18
<212> TYPE: DNA
<213> ORGANISM: Artificial Sequence
<220> FEATURE:
<223> OTHER INFORMATION: Synthesized nucleic acid molecule

<400> SEQUENCE: 6
cccttcacct ttccagag                                                 18

<210> SEQ ID NO 7
<211> LENGTH: 31
<212> TYPE: DNA
<213> ORGANISM: Artificial Sequence
<220> FEATURE:
<223> OTHER INFORMATION: Synthesized nucleic acid molecule

<400> SEQUENCE: 7
gactagcgga ggctagaagg agagagatgg g                                  31

<210> SEQ ID NO 8
<211> LENGTH: 24
<212> TYPE: DNA
<213> ORGANISM: Artificial Sequence
<220> FEATURE:
<223> OTHER INFORMATION: Synthesized nucleic acid molecule

<400> SEQUENCE: 8
ctcgacgcag gactcggctt gctg                                          24

<210> SEQ ID NO 9
```

```
<211> LENGTH: 50
<212> TYPE: DNA
<213> ORGANISM: Artificial Sequence
<220> FEATURE:
<223> OTHER INFORMATION: Synthesized nucleic acid molecule

<400> SEQUENCE: 9
aatttaatac gactcactat agggagactc ccccgcttaa tactgacgct          50

<210> SEQ ID NO 10
<211> LENGTH: 26
<212> TYPE: DNA
<213> ORGANISM: Artificial Sequence
<220> FEATURE:
<223> OTHER INFORMATION: Synthesized nucleic acid molecule

<400> SEQUENCE: 10
cttccccttg gttctctcat ctggcc                                    26

<210> SEQ ID NO 11
<211> LENGTH: 54
<212> TYPE: DNA
<213> ORGANISM: Artificial Sequence
<220> FEATURE:
<223> OTHER INFORMATION: Synthesized nucleic acid molecule

<400> SEQUENCE: 11
aatttaatac gactcactat agggagagac catcaatgag gaagctgcag aatg      54

<210> SEQ ID NO 12
<211> LENGTH: 26
<212> TYPE: DNA
<213> ORGANISM: Artificial Sequence
<220> FEATURE:
<223> OTHER INFORMATION: Synthesized nucleic acid molecule

<400> SEQUENCE: 12
ccatcctatt tgttcctgaa gggtac                                    26

<210> SEQ ID NO 13
<211> LENGTH: 31
<212> TYPE: DNA
<213> ORGANISM: Artificial Sequence
<220> FEATURE:
<223> OTHER INFORMATION: Synthesized nucleic acid molecule

<400> SEQUENCE: 13
gaaggctttc agcccagaag taatacccat g                              31

<210> SEQ ID NO 14
<211> LENGTH: 31
<212> TYPE: DNA
<213> ORGANISM: Artificial Sequence
<220> FEATURE:
<223> OTHER INFORMATION: Synthesized nucleic acid molecule

<400> SEQUENCE: 14
ggcaaatggt acatcaggcc atatcaccta g                              31

<210> SEQ ID NO 15
<211> LENGTH: 52
<212> TYPE: DNA
<213> ORGANISM: Artificial Sequence
<220> FEATURE:
<223> OTHER INFORMATION: Synthesized nucleic acid molecule

<400> SEQUENCE: 15
```
aatttaatac gactcactat agggagaggg gtggctcctt ctgataatgc tg            52

<210> SEQ ID NO 16
<211> LENGTH: 51
<212> TYPE: DNA
<213> ORGANISM: Artificial Sequence
<220> FEATURE:
<223> OTHER INFORMATION: Synthesized nucleic acid molecule

<400> SEQUENCE: 16
aattttaata cgactcacta tagggagaaa tcttgtgggg tggctccttc t              51

<210> SEQ ID NO 17
<211> LENGTH: 27
<212> TYPE: DNA
<213> ORGANISM: Artificial Sequence
<220> FEATURE:
<223> OTHER INFORMATION: Synthesized nucleic acid molecule

<400> SEQUENCE: 17
caagggactt tccgctgggg actttcc                                         27

<210> SEQ ID NO 18
<211> LENGTH: 22
<212> TYPE: DNA
<213> ORGANISM: Artificial Sequence
<220> FEATURE:
<223> OTHER INFORMATION: Synthesized nucleic acid molecule

<400> SEQUENCE: 18
caaatggcag tattcatcca ca                                              22

<210> SEQ ID NO 19
<211> LENGTH: 23
<212> TYPE: DNA
<213> ORGANISM: Artificial Sequence
<220> FEATURE:
<223> OTHER INFORMATION: Synthesized nucleic acid molecule

<400> SEQUENCE: 19
ctcccccgct taatactgac gct                                             23

<210> SEQ ID NO 20
<211> LENGTH: 25
<212> TYPE: DNA
<213> ORGANISM: Artificial Sequence
<220> FEATURE:
<223> OTHER INFORMATION: Synthesized nucleic acid molecule

<400> SEQUENCE: 20
ccatcaatga ggaagctgca gaatg                                           25

<210> SEQ ID NO 21
<211> LENGTH: 25
<212> TYPE: DNA
<213> ORGANISM: Artificial Sequence
<220> FEATURE:
<223> OTHER INFORMATION: Synthesized nucleic acid molecule

<400> SEQUENCE: 21
ggggtggctc cttctgataa tgctg                                           25

<210> SEQ ID NO 22
<211> LENGTH: 24
<212> TYPE: DNA

<213> ORGANISM: Artificial Sequence
<220> FEATURE:
<223> OTHER INFORMATION: Synthesized nucleic acid molecule

<400> SEQUENCE: 22
aaatcttgtg gggtggctcc ttct                                    24

<210> SEQ ID NO 23
<211> LENGTH: 26
<212> TYPE: DNA
<213> ORGANISM: Artificial Sequence
<220> FEATURE:
<223> OTHER INFORMATION: Synthesized nucleic acid molecule

<400> SEQUENCE: 23
ggtcccctag aagaagaact ccctcg                                  26

<210> SEQ ID NO 24
<211> LENGTH: 33
<212> TYPE: DNA
<213> ORGANISM: Artificial Sequence
<220> FEATURE:
<223> OTHER INFORMATION: Synthesized nucleic acid molecule

<400> SEQUENCE: 24
caccaaatgc ccctatctta tcaacacttc cgg                          33

<210> SEQ ID NO 25
<211> LENGTH: 51
<212> TYPE: DNA
<213> ORGANISM: Artificial Sequence
<220> FEATURE:
<223> OTHER INFORMATION: Synthesized nucleic acid molecule

<400> SEQUENCE: 25
aatttaatac gactcactat agggagaccc gagattgaga tcttctgcga c      51

<210> SEQ ID NO 26
<211> LENGTH: 54
<212> TYPE: DNA
<213> ORGANISM: Artificial Sequence
<220> FEATURE:
<223> OTHER INFORMATION: Synthesized nucleic acid molecule

<400> SEQUENCE: 26
aatttaatac gactcactat agggagaggt tatcgctgga tgtgtctgcg gcgt   54

<210> SEQ ID NO 27
<211> LENGTH: 25
<212> TYPE: DNA
<213> ORGANISM: Artificial Sequence
<220> FEATURE:
<223> OTHER INFORMATION: Synthesized nucleic acid molecule

<400> SEQUENCE: 27
gaggacaaac gggcaacata ccttg                                   25

<210> SEQ ID NO 28
<211> LENGTH: 52
<212> TYPE: DNA
<213> ORGANISM: Artificial Sequence
<220> FEATURE:
<223> OTHER INFORMATION: Synthesized nucleic acid molecule

<400> SEQUENCE: 28
aatttaatac gactcactat agggagatcc tggaattaga ggacaaacgg gc     52

<210> SEQ ID NO 29
<211> LENGTH: 25
<212> TYPE: DNA
<213> ORGANISM: Artificial Sequence
<220> FEATURE:
<223> OTHER INFORMATION: Synthesized nucleic acid molecule

<400> SEQUENCE: 29
cctcttcatc ctgctgctat gcctc                                  25

<210> SEQ ID NO 30
<211> LENGTH: 24
<212> TYPE: DNA
<213> ORGANISM: Artificial Sequence
<220> FEATURE:
<223> OTHER INFORMATION: Synthesized nucleic acid molecule

<400> SEQUENCE: 30
gagcatagca gcaggatgaa gagg                                   24

<210> SEQ ID NO 31
<211> LENGTH: 25
<212> TYPE: DNA
<213> ORGANISM: Artificial Sequence
<220> FEATURE:
<223> OTHER INFORMATION: Synthesized nucleic acid molecule

<400> SEQUENCE: 31
gcagagttca aaagcccttc agcgg                                  25

<210> SEQ ID NO 32
<211> LENGTH: 57
<212> TYPE: DNA
<213> ORGANISM: Artificial Sequence
<220> FEATURE:
<223> OTHER INFORMATION: Synthesized nucleic acid molecule

<400> SEQUENCE: 32
gggagagguu aucgcuggau gugucugcgg cguuuuauca uauuccucuu cauccug     57

<210> SEQ ID NO 33
<211> LENGTH: 25
<212> TYPE: DNA
<213> ORGANISM: Artificial Sequence
<220> FEATURE:
<223> OTHER INFORMATION: Synthesized nucleic acid molecule

<400> SEQUENCE: 33
tcctggaatt agaggacaaa cgggc                                  25

<210> SEQ ID NO 34
<211> LENGTH: 75
<212> TYPE: DNA
<213> ORGANISM: Artificial Sequence
<220> FEATURE:
<223> OTHER INFORMATION: Synthesized nucleic acid molecule

<400> SEQUENCE: 34
gggagagguu aucgcuggau gugucugcgg cguuuuauca uauuccucuu cauccugcug     60
cuaugccuca ucuuc                                             75

<210> SEQ ID NO 35
<211> LENGTH: 104
<212> TYPE: DNA

<213> ORGANISM: Artificial Sequence
<220> FEATURE:
<223> OTHER INFORMATION: Synthesized nucleic acid molecule

<400> SEQUENCE: 35
gggagacccg agauugagau cuucugcgac gcggcgauug agaucugcgu cugcgaggcg    60
agggaguucu ucuucuaggg gaccugccuc ggucccgucg ucua                    104

<210> SEQ ID NO 36
<211> LENGTH: 173
<212> TYPE: DNA
<213> ORGANISM: Artificial Sequence
<220> FEATURE:
<223> OTHER INFORMATION: Synthesized nucleic acid molecule

<400> SEQUENCE: 36
gggagacaaa uggcaguauu cauccacaau uuuaaaagaa aagggggau uggggggguac    60 agugcagggg aaagaauagu agacauaaua gcaacagaca uacaaacuaa agaauuacaa   120
aaacaaauua caaaaauuca aaauuuucgg guuuauuaca gggacagcag aaa          173

<210> SEQ ID NO 37
<211> LENGTH: 24
<212> TYPE: DNA
<213> ORGANISM: Artificial Sequence
<220> FEATURE:
<223> OTHER INFORMATION: Synthesized nucleic acid molecule

<400> SEQUENCE: 37
gaccaactcg tgtgtgaaac tcca                                          24

<210> SEQ ID NO 38
<211> LENGTH: 25
<212> TYPE: DNA
<213> ORGANISM: Artificial Sequence
<220> FEATURE:
<223> OTHER INFORMATION: Synthesized nucleic acid molecule

<400> SEQUENCE: 38
tcctggaatt agaggataaa cgggc                                         25

<210> SEQ ID NO 39
<211> LENGTH: 45
<212> TYPE: DNA
<213> ORGANISM: Artificial Sequence
<220> FEATURE:
<223> OTHER INFORMATION: Synthesized nucleic acid molecule

<400> SEQUENCE: 39
atttaatacg actcactata gggagacggt gaccgtggtc ccttg                   45

<210> SEQ ID NO 40
<211> LENGTH: 81
<212> TYPE: DNA
<213> ORGANISM: Artificial Sequence
<220> FEATURE:
<223> OTHER INFORMATION: Synthesized nucleic acid molecule

<400> SEQUENCE: 40
taaattaata cgactcacta tagggagatc agttacaatc gctggtatca acgctgagca    60
gacgctgacc gtggtccctt g                                             81

<210> SEQ ID NO 41
<211> LENGTH: 45

```
<212> TYPE: DNA
<213> ORGANISM: Artificial Sequence
<220> FEATURE:
<223> OTHER INFORMATION: Synthesized nucleic acid molecule

<400> SEQUENCE: 41
gaattaatac gactcactat agggagacct gaggagacgg tgacc            45

<210> SEQ ID NO 42
<211> LENGTH: 20
<212> TYPE: DNA
<213> ORGANISM: Artificial Sequence
<220> FEATURE:
<223> OTHER INFORMATION: Synthesized nucleic acid molecule

<400> SEQUENCE: 42
tatggtggtt tgacctttag                                         20

<210> SEQ ID NO 43
<211> LENGTH: 24
<212> TYPE: DNA
<213> ORGANISM: Artificial Sequence
<220> FEATURE:
<223> OTHER INFORMATION: Synthesized nucleic acid molecule

<400> SEQUENCE: 43
ggctttctca tggctgtcct tcag                                    24

<210> SEQ ID NO 44
<211> LENGTH: 24
<212> TYPE: DNA
<213> ORGANISM: Artificial Sequence
<220> FEATURE:
<223> OTHER INFORMATION: Synthesized nucleic acid molecule

<400> SEQUENCE: 44
ggtcttcctg aaatgcagtg gtcg                                    24

<210> SEQ ID NO 45
<211> LENGTH: 50
<212> TYPE: DNA
<213> ORGANISM: Artificial Sequence
<220> FEATURE:
<223> OTHER INFORMATION: Synthesized nucleic acid molecule

<400> SEQUENCE: 45
gaattaatac gactcactat agggagactc agaccctgag gctcaaagtc        50

<210> SEQ ID NO 46
<211> LENGTH: 22
<212> TYPE: DNA
<213> ORGANISM: Artificial Sequence
<220> FEATURE:
<223> OTHER INFORMATION: Synthesized nucleic acid molecule

<400> SEQUENCE: 46
ggagctgcag atgctgacca ac                                      22
```